(12) United States Patent
Levin et al.

(10) Patent No.: US 6,340,691 B1
(45) Date of Patent: Jan. 22, 2002

(54) ALKYNYL CONTAINING HYDROXAMIC ACID COMPOUNDS AS MATRIX METALLOPROTEINASE AND TACE INHIBITORS

(75) Inventors: Jeremy I. Levin, New City; Aranapakam M. Venkatesan, Rego Park; Derek C. Cole, New City, all of NY (US); James M. Chen, Bedminister, NJ (US); Jamie M. Davis, Nyack; George T. Grosu, Pearl River, both of NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/492,977

(22) Filed: Jan. 27, 2000

Related U.S. Application Data

(60) Provisional application No. 60/160,085, filed on Jan. 27, 1999.

(51) Int. Cl.$^7$ .................. C07D 211/40; C07D 209/44; C07D 333/56; C07D 321/00; A61K 31/47

(52) U.S. Cl. .............. 514/307; 514/327; 514/349; 514/311; 514/454; 514/443; 514/416; 514/423; 514/613; 514/617; 514/618; 514/619; 514/621; 546/216; 546/297; 546/170; 546/143; 546/147; 548/471; 548/472; 548/535; 549/57; 549/58; 549/388; 564/162; 564/163; 564/167; 564/169; 564/171

(58) Field of Search .................. 514/307, 311, 514/327, 349, 416, 423, 443, 454, 613, 617, 318, 619, 621; 546/143, 147, 170, 216, 297; 548/471, 472, 535; 549/57, 58, 388; 564/162, 163, 167, 169, 171

(56) References Cited

U.S. PATENT DOCUMENTS

| | | |
|---|---|---|
| 5,455,258 A | 10/1995 | MacPherson et al. |
| 5,506,242 A | 4/1996 | MacPherson et al. |
| 5,552,419 A | 9/1996 | MacPherson et al. |
| 5,753,653 A | 5/1998 | Bender et al. |
| 5,770,624 A | 6/1998 | Parker |
| 5,804,593 A | 9/1998 | Warpechoski et al. |
| 5,817,822 A | 10/1998 | Nantermet et al. |
| 5,929,097 A | 7/1999 | Levin et al. |
| 5,972,978 A | * 10/1999 | Andersen |

FOREIGN PATENT DOCUMENTS

| | | |
|---|---|---|
| DE | 19542189 | 5/1997 |
| EP | 606046 | 12/1993 |
| EP | 757037 | 7/1996 |
| EP | 757984 | 8/1996 |
| EP | 803505 | 4/1997 |
| WO | WO9535275 | 12/1995 |
| WO | WO9535276 | 12/1995 |
| WO | WO9600214 | 1/1996 |
| WO | WO9627583 | 9/1996 |
| WO | WO9633172 | 10/1996 |
| WO | WO9718194 | 5/1997 |
| WO | WO9719068 | 5/1997 |
| WO | WO9720824 | 6/1997 |
| WO | WO9722587 | 6/1997 |
| WO | WO9727174 | 7/1997 |
| WO | WO9745402 | 12/1997 |
| WO | WO9803166 | 1/1998 |
| WO | WO9807697 | 2/1998 |
| WO | WO9808815 | 3/1998 |
| WO | WO9808822 | 3/1998 |
| WO | WO9808823 | 3/1998 |
| WO | WO9808825 | 3/1998 |
| WO | WO9808827 | 3/1998 |
| WO | WO9808853 | 3/1998 |
| WO | WO9816503 | 4/1998 |
| WO | WO9816506 | 4/1998 |
| WO | WO9816514 | 4/1998 |
| WO | WO9816520 | 4/1998 |
| WO | WO9827069 | 6/1998 |
| WO | WO9831664 | 7/1998 |
| WO | WO9833768 | 8/1998 |
| WO | WO9834918 | 8/1998 |
| WO | WO9837877 | 9/1998 |
| WO | WO9839313 | 9/1998 |
| WO | WO9839329 | 9/1998 |
| WO | WO9842659 | 10/1998 |
| WO | WO9843963 | 10/1998 |

OTHER PUBLICATIONS

Venkatesan, CA 129:230641, 1998.*
Breault, CA 126:157515, 1997.*
Shire, M.G., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest., 81, 1925, (1988).
Miethke et al., J. Exp. Med., 175, 91 (1992).
Piquet, P.F., J. Exp. Med. 166, 1280 (1987).
Beuther, B., Ann. Rev., Biochem, 57, 505 (1988).
Ksontini, R., Arch. Surg., 133, 558, (1998).
Packer, M., Circulation, 92(6), 1379 (1995).

(List continued on next page.)

Primary Examiner—D. Margaret Seaman
(74) Attorney, Agent, or Firm—John W. Hogan, Jr.

(57) ABSTRACT

Compounds of the formula

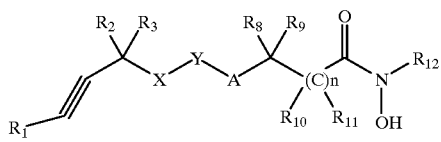

are useful in treating disease conditions mediated by TNF-α, such as rheumatoid arthritis, osteoarthritis, sepsis, AIDS, ulcerative colitis, multiple sclerosis, Crohn's disease and degenerative cartilage loss.

5 Claims, No Drawings

OTHER PUBLICATIONS

Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).
McGeehan et al, Current Pharmaceutical Design, 2, 662 (1996).
Script 20, 2349 (1998).
MacPherson et al., J. Med. Chem., 40, 2525 (1997).
Tamura et al., J. Med. Chem. 41, 640 (1998).
Levin et al., Bioorg. & Med. Chem. Letters, 8, 2657 (1998).
Pikul et al., J. Med. Chem., 41, 3568 (1998).

* cited by examiner

ALKYNYL CONTAINING HYDROXAMIC ACID COMPOUNDS AS MATRIX METALLOPROTEINASE AND TACE INHIBITORS

This application claims the benefit of U.S. Provisional Application No. 60/160,085, filed Jan. 27, 1999.

FIELD OF INVENTION

This invention relates to acetylenic hydroxamic acids which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

Matrix metalloproteinases (MMPs) are a group of enzymes that have been implicated in the pathological destruction of connective tissue and basement membranes. These zinc containing endopeptidases consist of several subsets of enzymes including collagenases, stromelysins and gelatinases. Of these classes, the gelatinases have been shown to be the MMPs most intimately involved with the growth and spread of tumors. It is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neo-vascularization and corneal graft rejection. For recent reviews, see: (1) Recent Advances in Matrix Metalloproteinase Inhibitor Research, R. P. Beckett, A. H. Davidson, A. H. Drummond, P. Huxley and M. Whittaker, Research Focus, Vol. 1, 16–26, (1996), (2) Curr. Opin. Ther. Patents (1994) 4(1): 7–16, (3) Curr. Medicinal Chem. (1995) 2: 743–762, (4) Exp. Opin. Ther. Patents (1995) 5(2): 1087–110, (5) Exp. Opin. Ther. Patents (1995) 5(12): 1287–1196: (6) Exp. Opin. Ther. Patents (1998) 8(3): 281–259.

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, *J. Ann. Med.* 1997, 29, 499; Camussi, G.; Lupia, E. *Drugs,* 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation,* 1995, 92(6), 1379; Ferrari, R.; Bachetti, T.; et. al. *Circulation,* 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science,* 1993, 259, 87.] and HIV infection (Peterson, P. K.; Gekker, G.; et. al. *J Clin. Invest.* 1992, 89, 574; Pallares-Trujillo, J.; Lopez-Soriano, F. J. Argiles, *J. M. Med Res. Reviews,* 1995, 15(6), 533.]], in addition to its well-documented antitumor properties [Old, L. *Science,* 1985, 230, 630.]. For example, research with anti-TNFα antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A; Panayi, G. S. *Br. J. Rheumatol.* 1995, 34, 334; *Pharmaprojects,* 1996, Therapeutic Updates 17 (Oct.), au97-M2Z.]. This observation has recently been extended to humans as well as described in "TNF-α in Human Diseases", *Current Pharmaceutical Design,* 1996, 2, 662.

It is expected that small molecule inhibitors of TACE will have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [Scrip, 1998, 2349, 20] Long acting, selective, orally bioavailable non-peptide inhibitors of TACE would thus be highly desirable for the treatment of the disease states discussed above.

Sulfone hydroxamic acid inhibitors of MMPs, of general structure I have been disclosed [Burgess, L. E.; Rizzi, J. P.; Rawson, D. J. Eur Patent Appl. 818442. Groneberg, R. D.; Neuenschwander, K. W.; Djuric, S. W.; McGeehan, G. M.; Burns, C. J.; Condon, S. M.; Morrissette, M. M.; Salvino, J. M.; Scotese, A. C.; Ullrich, J. W. PCT Int. Appl. WO 97/24117. Bender, S. L.; Broka, C. A.; Campbell, J. A.; Castelhano, A. L.; Fisher, L. E.; Hendricks, R. T.; Sarma, K. Eur. Patent Appl. 780386. Venkatesan, A. M.; Grosu, G. T.; Davis, J. M.; Hu, B.; O'Dell, M. J. PCT Int. Appl. WO 98/38163.]. An exemplification of this class of MMP inhibitor is RS-130830, shown below.

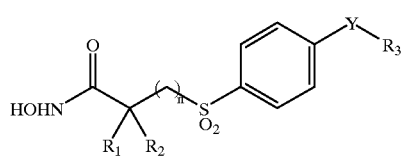

I

-continued

RS-130830

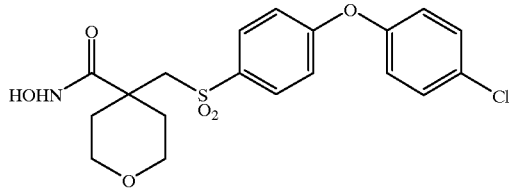

Within the sulfone-hydroxamic acid class of MMP inhibitor, the linker between the sulfone and hydroxamic acid moieties has been extended to three carbons I, n=2) without significant loss in potency [Barta, T. E.; Becker, D. P.; Villamil, C. I.; Freskos, J. N.; Mischke, B. V.; Mullins, P. B.; Heintz, R. M.; Getman, D. P.; McDonald, J. J. PCT Into Appl. WO 98/39316. McDonald, J. J.; Barta, T. E.; Becker, D. P.; Bedell, L. J.; Rao, S. N.; Freskos, J. N.; Mischke, B. V. PCT Int. Appl. WO 98/38859.].

Piperidine sulfone hydroxamic acids, II (n=1) have been reported [Becker, D. P.; Villamil, C. I.; Boehm, T. L.; Getman, D. P.; McDonald, J. J.; DeCrescenzo, G. A. PCT Int. Appl. WO 98/39315.]. Similar piperidine derivatives in which the methylene linking the piperidine ring to the sulfone has been deleted (II, n=0) have been reported [Venkatesan, A. M.; Grosu, G. T.; Davis, J. M.; Baker, J. L. PCT Int. Appl. WO 98/37877.].

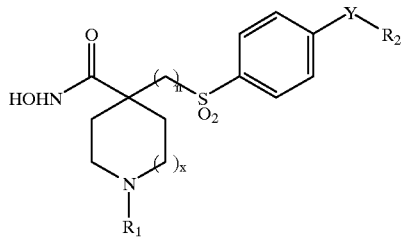

II

Sulfone-hydroxamic acids III, in which a hydroxyl group has been placed alpha to the hydroxamic acid, have been disclosed [Freskos, J. N.; Boehm, T. L.; Mischke, B. V.; Heintz, R. M.; McDonald, J. J.; DeCrescenzo, G. A.; Howard, S. C. PCT Int. Appl. WO 98/39326. Robinson, R. P. PCT Int. Appl. WO 98/34915.].

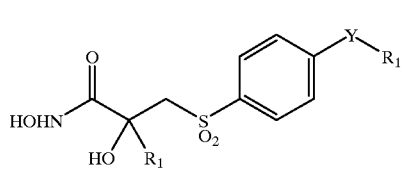

III

Sulfone-based MMP inhibitors of general structure IV, which utilize a thiol as the zinc chelator, have been reported [Freskos, J. N.; Abbas, Z. S.; DeCrescenzo, G. A.; Getman, D. P.; Heintz, R. M.; Mischke, B. V.; McDonald, J. J. PCT Int. Appl. WO 98/03164].

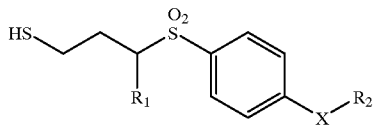

IV

Inhibitors of stromelysin with general structure V have been disclosed [Shuker, S. B.; Hajduk, P. J.; Meadows, R. P.; Fesik, S. W. Science, 1996, 274, 1531–1534. Hajduk, P. J.; Sheppard, G.; Nettesheim, D. G.; Olejniczak, E. T.; Shuker, S. B.; Meadows, R. P.; Steinman, D. H.; Carrera, Jr., G. M.; Marcotte, P. A.; Severin, J.; Walter, K.; Smith, H.; Gubbins, E.; Simmer, R.; Holzman, T. F.; Morgan, D. W.; Davidsen, S. K.; Summers, J. B.; Fesik, S. W. J. Am. Chem Soc. 1997, 119, 5818–5827. Olejniczak, E. T.; Hajduk, P. J.; Marcotte, P. A.; Nettesheim, D. G.; Meadows, R. P.; Edalji, R.; Holzman, T. F.; Fesik, S. W. J. Am. Chem. Soc. 1997, 119, 5828–5832. Fesik, S. W.; Summers, J. B.; Davidsen, S. K.; Sheppard, G. S.; Steinman, D. H.; Carrera, G. M.; Florjancic, A.; Holms, J. H. PCT Int. Appl. WO 97/18188.].

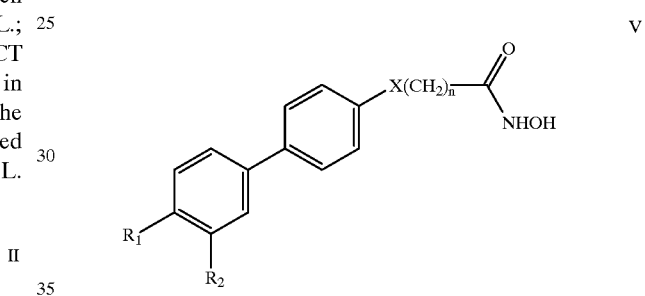

V

Salah et al., Liebigs Ann. Chem. 195, (1973) discloses some aryl substituted thio and aryl substituted sulfonyl acetohydroxamic acid derivatives of general formula 1. These compounds were prepared to study the Mannich reaction. Subsequently, they were tested for their fungicidal activity.

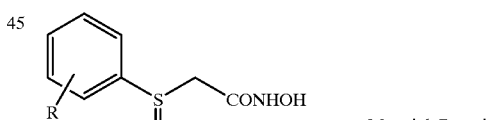

1

Mannich Reaction

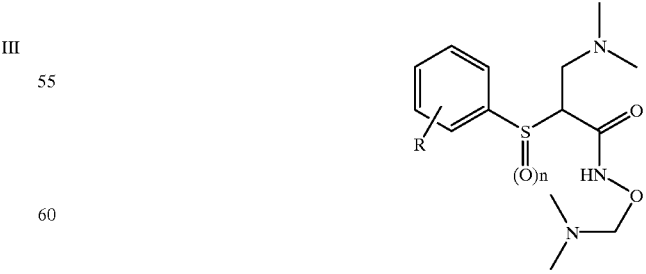

Some sulfone carboxylic acids are disclosed in U.S. Pat. No. 4,933,367. Those compounds were shown to exhibit hypoglycemic activity.

DETAILED DESCRIPTION OF THE INVENTION

The present invention relates to novel, low molecular weight, non-peptide inhibitors of matrix metalloproteinases (MMPs) and TNF-α converting enzyme (TACE) for the treatment of arthritis, tumor metastasis, tissue ulceration, abnormal wound healing, periodontal disease, bone disease, diabetes (insulin resistance) and HIV infection.

In accordance with this invention there is provided compounds of general formula I:

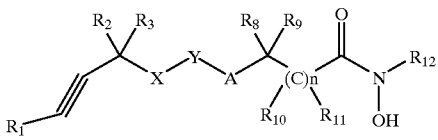

wherein:
- $R_1$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, or $C_5$–$C_8$-cycloheteroalkyl having from 1–2 heteroatoms selected from N, NR7, S and O;
- $R_2$ and $R_3$ are each independently, hydrogen, alkyl of 1–6 carbon atoms, —CN, or —CCH;
- R5 is hydrogen, alkyl of 1–8 carbon atoms, cycloalkyl of 3–6 carbon atoms, aryl, heteroaryl, or C4–C8-cycloheteralkyl;
- R7 is hydrogen, aryl, aralkyl, alkyl of 1–6 carbon atoms, or cycloalkyl of 3–6 carbon atoms, oxy, C1–C8 alkanoyl, COOR5, COR5, —SO$_2$—C1–C8 alkyl, —SO$_2$-aryl, —SO$_2$-heteroaryl,—CO—NHR;
- $R_8$, $R_9$, $R_{10}$, and $R_{11}$ are each, independently, hydrogen, aryl, aralkyl, 5–10 membered heteroaryl having from 1–3 heteroatoms selected from N, NR7, O and S, heteroaralkyl having from 1–3 heteroatoms selected from N, NR7, O and S, cycloalkyl of 3–6 carbon atoms, —C4–C8-cycloheteroalkyl having from 1–3 heteroatoms selected from N, NR7, O and S, alkyl of 1–18 carbon atoms, alkenyl of 2–18 carbon atoms, alkynyl of 2–18 carbon atoms;
- $R_{12}$ is hydrogen, aryl or 5–10 membered heteroaryl having from 1–3 heteroatoms selected from N, NR7, S and O, cycloalkyl of 3–6 carbon atoms, —C5–C8-cycloheteroalky having from 1 to 2 heteroatoms selected from N, NR7, S and O, or alkyl of 1–6 carbon atoms;
- A is O, S, SO, SO$_2$, NR$_7$, or CH;
- X is O, S, SO, SO$_2$, NR$_7$, or C,
- Y is aryl or heteroaryl, with the proviso that A and X are not bonded to adjacent atoms of Y; and
- n is 0–2; or a pharmaceutically acceptable salt thereof.

In some preferred embodiments of the present invention Y is phenyl, pyridyl, thienyl, furanyl, imidazolyl, triazolyl and thiadiazolyl.

Still more preferred compounds of the present invention are compounds of Formula I wherein $R_2$ and $R_3$ are each, independently, hydrogen or alkyl of 1–6 carbon atoms; $R_{12}$ is hydrogen; and Y is phenyl.

The most preferred matrix metalloproteinase and TACE inhibiting compounds of this invention are:
2-(4-But-2-ynyloxy-benzenesulfonyl)-N-hydroxy-2-methyl-3-pyridin-3-yl-propionamide;
2-(4-But-2-ynyloxy-phenylsulfanyl)-N-hydroxy-propionamide;
2-(4-But-2-ynyloxy-benzesulfonyl)-N-hydroxy-2-methyl-3-[4-(2-piperidin-1-yl-ethoxy)-phenyl]-propionamide;
3-Biphenyl-4-yl-2-(4-but-2-ynyloxy-benzenesulfonyl)-N-hydroxy-2-methyl-propionamide;
2-(4-But-2-ynyloxy-phenysulfanyl)-octanoic acid hydroxamide;
2-(But-2-ynyloxy-benzenesulfonyl)-octanoic acid hydroxamide;
2[(R)-(4-Butyl-2-ynyloxy)-sulfinyl-N-hydroxyoctanamide;
2[(S)-(4-Butyl-2-ynyloxy)-sulfinyl-N-hydroxyoctanamide;
3-(4-But-2-ynyloxy-phenoxy)-N-hydroxy-propionamide;
4-(4-But-2-ynyloxy-phenoxy)-N-hydroxy-butyramide;
2-(4-But-2-ynyloxy-phenoxy)-N-hydroxy-acetamide;
4-(4-But-2-ynyloxy-phenyl)-N-hydroxy-butyramide;
Quinoline-2-carboxylic acid [5-(4-but-2-ynyloxy-phenylsulfanyl)-5-hydroxycarbamoyl-pentyl]-amide;
2-(4-But-2-ynyloxy-phenylsulfanyl)-6-[2-(1,3-dioxo-1,3-dihydro-isoindol-2-yl)-acetylamino]-hexanoic acid hydroxyamide;
N-[5-(4-But-2-ynyloxy-phenylsulfanyl)-5-hydroxycarbamoyl-pentyl]-2-phenethyl-benzamide;
2-(4-But-2-ynyloxy-phenylsulfanyl)-6-[2-(3,4-dichloro-phenyl)-acetylamino]-hexanoic acid hydroxyamide;
Quinoline-3-carboxylic acid [5-(4-but-2-ynyloxy-phenylsulfanyl)-5-hydroxycarbamoyl-pentyl]-amide;
2-(4-But-2-ynyloxy-phenylsulfanyl)-6-(4-thiophen-2-yl-butyrylamino)-hexanoic acid hydroxyamide;
9H-Xanthene-9-carboxylic acid [5-(4-but-2-ynyloxy-phenylsulfanyl)-5-hydroxycarbamoyl-pentyl]-amide;
2-(4-But-2-ynyloxy-phenylsulfanyl)-6-diphenylacetylamino-hexanoic acid hydroxyamide;
Isoquinoline-1-carboxylic acid [5-(4but-2-ynyloxy-phenylsulfanyl)-5-hydroxycarbamoyl-pentyl]-amide;
6-(2-Benzo[b]thiophen-3-yl-acetylamino)-2-(4but-2-ynyloxy-phenyl-sulfanyl)-hexanoic acid hydroxyamide;
Quinoline-2-carboxylic acid [5-(4-but-2-ynyloxy-benzenesulfinyl)-5-hydroxycarbamoyl-pentyl]-amide;
2-(4-But-2-ynyloxy-benzenesulfinyl)-6-[2-(1,3-dioxo-1,3-dihydro-isoindol-2-yl)-acetylamino]-hexanoic acid hydroxyamide;
N-[5-(4-But-2-ynyloxy-benzenesulfinyl)-5-hydroxycarbamoyl-pentyl]-2-phenethyl-benzamide;
2-(4-But-2-ynyloxy-benzenesulfinyl)-6-[2-(3,4-dichloro-phenyl)-acetylamino]-hexanoic acid hydroxyamide;
Quinoline-3-carboxylic acid [5-(4-but-2-ynyloxy-benzenesulfinyl)-5-hydroxycarbamoyl-pentyl]-amide;
2-(4-But-2-ynyloxy-benzenesulfinyl)-6-(4-thiophen-2-yl-butyrylamino)-hexanoic acid hydroxyamide;
9H-Xanthene-9-carboxylic acid [5-(4-but-2-ynyloxy-benzenesulfinyl)-5-hydroxycarbamoyl-pentyl]-amide;
2-(4-But-2-ynyloxy-benzenesulfinyl)-6-diphenylacetylamino-hexanoic acid hydroxyamide;
Isoquinoline-1-carboxylic acid [5-(4-but-2-ynyloxy-benzenesulfinyl)-5-hydroxycarbamoyl-pentyl]-amide;
6-(2-Benzo[b]thiophen-3-yl-acetylamino)-2-(4-but-2-ynyloxy-benzene-sulfinyl)-hexanoic acid hydroxyamide;
2-(4-But-2-ynyloxy-benzenesulfinyl)-6-(2-1H-indol-3-yl-acetylamino)-hexanoic acid hydroxyamide;
Quinoline-2-carboxylic acid [5-(4-but-2-ynyloxy-benzenesulfonyl)-5-hydroxycarbamoyl-pentyl]-amide;
2-(4-But-2-ynyloxy-benzenesulfonyl)-6-[2-(1,3-dioxo-1,3-dihydro-isoindol-2-yl)-acetylamino]-hexanoic acid hydroxyamide;
N-[5-(4-But-2-ynyloxy-benzenesulfonyl)-5-hydroxycarbamoyl-pentyl]-2-phenethyl-benzamide;

2-(4-But-2-ynyloxy-benzenesulfonyl)-6-[2-(3,4-dichloro-phenyl)-acetylamino]-hexanoic acid hydroxyamide;

Quinoline-3-carboxylic acid [5-(4-but-2-ynyloxy-benzenesulfonyl)-5-5-hydroxycarbamoyl-pentyl]-amide;

9H-Xanthene-9-carboxylic acid [5-(4-but-2-ynyloxy-benzenesulfonyl)-5-hydroxycarbamoyl-pentyl]-amide;

2-(4-But-2-ynyloxy-benzenesulfonyl)-6-diphenylacetylaminohexanoic acid hydroxyamide;

Isoquinoline-1-carboxylic acid [5-(4-but-2-ynyloxy-benzenesulfonyl)-5-hydroxycarbamoyl-pentyl]-amide;

6-(2-Benzo[b]thiophen-3-yl-acetylamino)-2-(4-but-2-ynyloxy-benzenesulfonyl)-hexanoic acid hydroxyamide;

Quinoline-2-carboxylic acid ([5-(4-but-2-ynyloxy-phenylsulfanyl)-5-hydroxycarbamoyl-pentylcarbamoyl]-methyl)-amide;

2-(4-But-2-ynyloxy-phenylsulfanyl)-6-{2-[2-(1,3-dioxo-1,3-dihydroisoindol-2-yl)-acetylamino]-acetylamino}hexanoic acid hydroxyamide;

N-{[5-(4-But-2-ynyloxy-phenylsulfanyl)-5-hydroxycarbamoyl-pentylcarbamoyl]-methyl}-2-phenethyl-benzamide;

2-(4-But-2-ynyloxy-phenylsulfanyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-phenylsulfanyl)-5-hydroxycarbamoyl-pentylcarbamoyl]-methyl}-amide;

9H-Xanthene-9-carboxylic acid {[5-(4-but-2-ynyloxy-phenylsulfanyl)-5-hydroxycarbamoyl-pentylcarbamoyl]-methyl}-amide;

2-(4But-2-ynyloxy-phenylsulfanyl)-6-(2-diphenylacetylamino-acetylamino)-hexanoic acid hydroxyamide;

Isoquinoline-1-carboxylic acid {[5-(4-but-2-ynyloxy-phenylsulfanyl)-5-hydroxycarbamoyl-pentylcarbamoyl]-methyl}-amide;

1-Methyl-1H-pyrrole-2-carboxylic acid {[5-(4-but-2-ynyloxy-phenylsulfanyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy-phenylsulfanyl hexanoic acid hydroxyamide;

Quinoline-2-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-{2-[2-(1,3-dioxo-1,3-dihydroisoindol-2-yl)-acetylamino]-acetylamino}-hexanoic acid hydroxyamide;

N-{[5-(4-But-2-ynyloxy-benzenesulfinyl)-5-hydroxycarbamoyl-pentylcarbamoyl]-methyl}-2-phenethyl-benzamide;

2-(4-But-2-ynyloxy-benzenesulfinyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-benzenesulfinyl)-5-hydroxycarbamoyl-pentylcarbamoyl]-methyl}amide;

2-(4-But-2-ynyloxy-benzenesulfinyl)-6-[2-(4-thiophen-2-yl-butyrylamino)-acetylamino]-hexanoic acid hydroxyamide;

9H-Xanthene-9-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-(2-diphenylacetylamino-acetylamino)-hexanoic acid hydroxyamide;

1-Methyl-1H-pyrrole-2-carboxylic acid {[5-(4-but-2-ynyloxy-benzenesulfinyl)-5-hydroxycarbamoyl-pentylcarbamoyl]-methyl)-amide;

2-(4-But-2-ynyloxy-benzenesulfonyl)-6-52-[2-(1,3-dioxo-1,3-dihydroisoindol-2-yl)-acetylamino]-acetylamino)-hexanoic acid hydroxyamide;

N-{[5-(4-But-2-ynyloxy-benzenesulfonyl)-5-hydroxycarbamoyl-pentylcarbamoyl]-methyl}-2-phenethyl-benzamide;

2-(4-But-2-ynyloxy-benzenesulfonyl)-6-1 2-[2-(3,4-dichloro-phenyl)-acetylamino)-acetylamino}-hexanoic acid hydroxyamide;

Quinoline-3-carboxylic acid {[5-(4-but-2-ynyloxy-benzenesulfonyl)-5-hydroxycarbamoyl-pentylcarbamoyl]-methyl}amide;

9H-Xanthene-9-carboxylic acid {[5-(4but-2-ynyloxy-benzenesulfonyl)-5-hydroxycarbamoyl-pentylcarbamoyl]-methyl}-amide;

2-(4-But-2-ynyloxy-benzenesulfonyl)-6-(2-diphenylacetylamino-acetylamino)-hexanoic acid hydroxyamide;

Isoquinoline-1-carboxylic acid {[5-(4-but-2-ynyloxy-benzenesulfonyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy benzenesulfonyl hexanoic acid hydroxyamide;

2-(4-But-2-ynyloxy-benzenesulfonyl)-6-[2-(2-1H-indol-3-yl-acetylamino)-acetylamino]-hexanoic acid hydroxyamide;

2-{[4-(2-butynyloxy)phenyl]sulfonyl}-N-hydroxy-4-{4-[2-(1-piperidinyl)ethoxy phenyl}butanamide;

2-{[4-(2-butynyloxy)phenyl]sulfonyl}-7-cyano-N-hydroxy heptanamide;

2-{[4-(2-butynyloxy)phenyl]sulfanyl}-2-cyclohexyl-N-hydroxyacetamide;

2-{[4-(2-butynyloxy)phenyl]sulfinyl}-2-cyclohexyl-N-hydroxyacetamide;

2-{[4-(2-butynyloxy)phenyl]sulfonyl}-2-cyclohexyl-N-hydroxyacetamide;

2-{[4-(2-butynyloxy)phenyl]sulfanyl}-N-hydroxy-2-(4-methoxyphenyl) acetamide;

(2R)-2-{[4-(2-butynyloxy)phenyl]sulfinyl}-N-hydroxy-2-(4-methoxyphenyl)ethanamide;

(2S)-2-{[4-(2-butynyloxy)phenyl]sulfinyl}-N-hydroxy-2-(4-methoxyphenyl)ethanamide;

2-{[4-(2-butynyloxy)phenyl]sulfonyl}-N-hydroxy-2-(4-methoxyphenyl)acetamide;

2-{[4-(2-butynyloxy)phenyl]sulfanyl}-2-(4-chlorophenyl)-N-hydroxyacetamide;

2-{[4-(2-butynyloxy)phenyl]sulfanyl}-2-(4-chlorophenyl)-N-hydroxyacetamide;

2-{[4-(2-butynyloxy)phenyl]sulfonyl-2-(4-chlorophenyl)-N-hydroxy-acetamide;

2-{[4-(2-butynyloxy)phenyl]sulfanyl}-2-(3-chlorophenyl)-N-hydroxyacetamide;

2-{[4-(2-butynyloxy)phenyl]sulfonyl}-2-(3-chlorophenyl)-N-hydroxyacetamide;

2-(4-bromophenyl)-2-{[4-(2-butynyloxy)phenyl]sulfanyl-N-hydroxyacetamide;

(2S)-2-(4-bromophenyl)-2-{[4-(2-butynyloxy)phenyl]sulfinyl-N-hydroxyacetamide;

(2R)-2-(4-bromophenyl)-2-{[4-(2-butynyloxy)phenyl]sulfinyl-N-hydroxyacetamide;

2-(4-bromophenyl)-2-{[4-(2-butynyloxy)phenyl]sulfonyl-N-hydroxy-acetamide;

2-{[4-(2-butynyloxy)phenyl]sulfanyl}-N-hydroxy-2-(4-(2-thienyl)phenyl]-acetamide;

(2R)-2-{[4-(2-butynyloxy)phenyl]sulfinyl}-N-hydroxy-2-[4-(2-thienyl)-phenyl]ethanamide;

2-{[4-(2-butynyloxy)phenyl]sulfonyl}-N-hydroxy-2-[4-(2-thienyl)-phenyl]acetamide;
2-{[4-(2-Butynyloxy)phenyl]sulfanyl}-N-hydroxy-2-(1-napthyl)acetamide;
2-{[4-(2-Butynyloxy)phenyl]sulfinyl}-N-hydroxy-2-(1-napthyl)acetamide;
2-{[4-(2-Butynyloxy)phenyl]sulfonyl}-N-hydroxy-2-(1-napthyl)acetamide;
2-{[4-(2-Butynyloxy)phenyl]sulfanyl}-2-(4-fluorophenyl)-N-hydroxy-2-(1-napthyl)acetamide;
2-{[4-(2-butynyloxy)phenyl]sulfinyl-2-(4-fluorophenyl)-N-hydroxyacetamide;
2-{[4-(2-butynyloxy)phenyl]sulfonyl-2-(4-fluorophenyl)-N-hydroxyacetamide;
2-(2-methoxyphenyl)-2-{[4-(2-butynyloxy)phenyl]sulfanyl-N-hydroxy-acetamide;
2-(2-methoxyphenyl)-2-{[4-(2-butynyloxy)phenyl]sulfinyl}-N-hydroxyacetamide;
2-{[4-(2-butynyloxy)phenyl]sulfanyl-N-hydroxy-2-(4-ethoxyphenyl)acetamide;
2-{[4-(2-Butynyloxy)phenyl]sulfinyl-N-hydroxy-2-(4-ethoxyphenyl)acetamide;
2-{[4-(2-butynyloxy)phenyl]sulfonyl-2-(4-chlorophenyl)-N-hydroxyacetamide;
2-{[4-(2-Butynyloxy)phenyl]sulfanyl-N-hydroxy-2-(3-bromophenyl)acetamide;
(2R)-2-{[4-(2-butynyloxy)phenyl]sulfinyl-N-hydroxy-2-(3-bromophenyl)acetamide;
(2S)-2-{[4-(2-butynyloxy)phenyl]sulfinyl-N-hydroxy-2-(3-bromophenyl)acetamide;
2-{[4-(2-Butynyloxy)phenyl]sulfonyl}-2-(3-bromophenyl)-N-hydroxyacetamide;
2-{[4-(2-Butynyloxy)phenyl]sulfanyl}-2-isopropyl-N-hydroxyacetamide;
R-2-{[4-(2-butynyloxy)phenyl]sulfinyl}-2-isopropyl-N-hydroxyacetamide;
S-2-{[4-(2-butynyloxy)phenyl]sulfinyl}-2-isopropyl-N-hydroxyacetamide;
2-{[4-(2-butynyloxy)phenyl]sulfonyl}-2-isopropyl-N-hydroxyacetamide;
2-{[4-(2-Butynyloxy)phenyl]sulfanyl}-2-phenyl-N-hydroxyacetamide;
R-2-{[4-(2-butynyloxy)phenyl]sulfinyl}-2-phenyl-N-hydroxyacetamide;
S-2-{[4-(2-butynyloxy)phenyl]sulfinyl}-2-phenyl-N-hydroxyacetamide;
2-{[4-(2-Butynyloxy)phenyl]sulfanyl}-2-(2-naphthyl)-N-hydroxyacetamide;
2-{[4-(2-butynyloxy)phenyl]sulfinyl}-2-(2-naphthyl)-N-hydroxyacetamide;
2-{[4-(2-butynyloxy)phenyl]sulfonyl}-2-(2-naphthyl)-N-hydroxyacetamide;
Tert-butyl-4-[1-{[4-(2-butynyloxy)phenyl]sulfonyl}-2-(hydroxyamino)-2-oxyethyl]-1-piperidine carboxylate;
2-{[4-(2-butynyloxy)phenyl]sulfonyl}-N-hydroxy-2-(4-piperidinyl)acetamide;
2-{[4-(2-butynyloxy)phenyl]sulfonyl}-N-hydroxy-2-[2-(4-methoxybenzyl)-4-piperidinyl]acetamide;
2-(1-benzoyl-4-piperidinyl)-2-{[4-(2-butynyloxy)phenyl]sulfonyl}-N-hydroxyacetamide;
2-(1-acetyl-4-piperidinyl)-2-{[4-(2-butynyloxy)phenyl]sulfonyl-N-hydroxyacetamide;
2-{[4-(2-Butynyloxy)phenyl]sulfonyl}-N-hydroxy-2-tetrahydro-2H-pyran-4yl-acetamide;
2-{[4-(2-Butynyloxy)phenyl]sulfonyl}-N-hydroxy-2-tetrahydro-2H-thiopyran-4yl-acetamide;
2-{[4-(2-Butynyloxy)phenyl]sulfonyl}-N-hydroxy-2-(1-oxidotetrahydro-2H-thiopyran-4yl)acetamide; and
2-{[4-(2-Butynyloxy)phenyl]sulfonyl)-N-hydroxy-2-(1,1-dioxidotetrahydro-2H-thiopyran-4yl)acetamide.

Heteroaryl, as used throughout, is a 5–10 membered mono- or bicyclic ring having from 1–3 heteroatoms selected from N, NR7, S and O. Heteroaryl is preferably

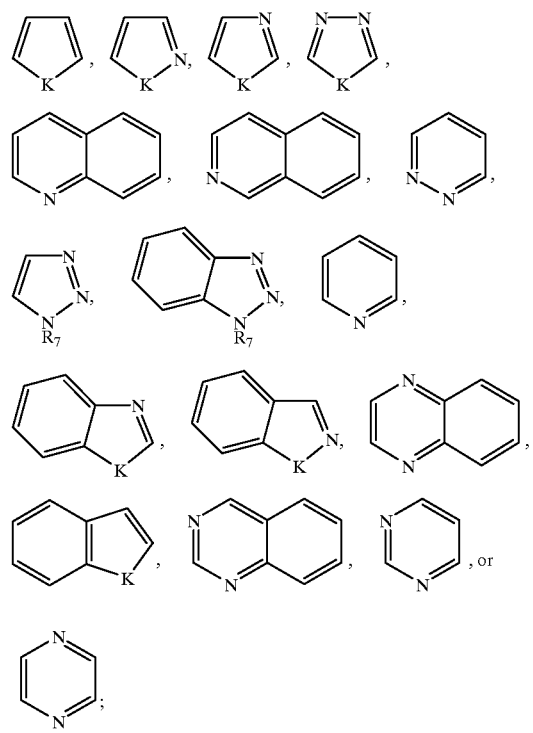

wherein K is defined as O, S or —NR₇ and R7 is as defined before. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups of the present invention may be mono or disubstituted.

—$C_4$–$C_8$-cycloheteroalkyl is defined as

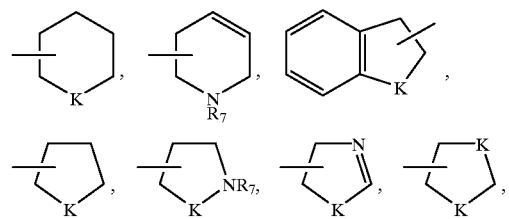

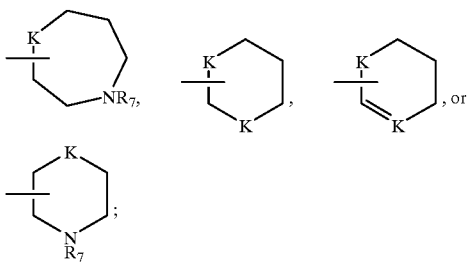

wherein K is O, S or NR7 and R7 is as defined before. Preferred heterocycloalkyl rings include piperidine, piperazine, morpholine, tetrahydropyran, tetrahydrofuran or pyrrolidine. Heterocycloalkyl groups of the present invention may optionally be mono- or di-substituted.

Aryl, as used herein refers to phenyl or naphthyl aromatic rings which may, optionally be mono- or di-substituted.

Alkyl, alkenyl, alkynyl, and perfluoroalkyl include both straight chain as well as branched moieties. Alkyl, alkenyl, alkynyl, and cycloalkyl groups may be unsubstituted unsubstituted (carbons bonded to hydrogen, or other carbons in the chain or ring) or may be mono- or poly-substituted. Lower alkyl is C1–C6 alkyl.

Aralkyl as used herein refers to substituted alkyl group, -alkyl-aryl, wherein alkyl is lower alkyl and preferably C1–C3, and aryl is as previously defined.

Heteroaralkyl as used herein refers to substituted alkyl group, -alkyl-heteroaryl, wherein alkyl is lower alkyl and preferably C1–C3, and heteroaryl is as previously defined.

Halogen means bromine, chlorine, fluorine, and iodine. Suitable substituents of aryl, aralkyl, heteroaryl, heteroaralkyl, alkyl, alkenyl, alkynyl, cycloalkyl and include, but are not limited to halogen, alkyl of 1–6 carbon atoms; alkenyl of 2–6 carbon atoms; alkynyl of 2–6 carbon atoms, cycloalkyl of 3–6 carbon atoms, —OR$_5$, —CN, —COR$_5$, perfluoroalkyl of 1–4 carbon atoms, —O-perfluoroalkyl of 1–4 carbon atoms, —CONR$_5$R$_6$, —S(O)nR$_5$, —OPO(OR$_5$)OR$_6$, —PO(OR)R$_6$, —OC(O)OR$_5$, —OR$_5$NR$_5$R$_6$, —OC(O)NR$_5$R$_6$, —C(O)NR$_5$OR$_6$, —COOR$_5$, —SO$_3$H, —NR$_5$R$_6$, —N[(CH$_2$)$_2$]$_2$NR$_5$, —NR$_5$COR$_6$, —NR$_5$COOR$_6$, —SO$_2$NR$_5$R$_6$, —NO$_2$, —N(R$_5$)SO$_2$R$_6$, —NR$_5$CONR$_5$R$_6$, —NR$_5$C(=NR$_6$)NR$_5$R$_5$, —NR$_5$C(=NR)N(SO2)R$_5$R$_6$, —NR$_5$C(=NR)N(C=OR$_5$)R$_6$, —tetrazol-5-yl, —SO$_2$NHCN, —SO$_2$NHCONR$_5$R$_6$, phenyl, heteroaryl or —C$_5$–C$_8$-cycloheteroalkyl;

wherein

—NR$_5$R$_6$ may form a pyrrolidine, piperidine, morpholine, thiomorpholine, oxazolidine, thiazolidine, pyrazolidine, piperazine, or azetidine ring;

R$_5$ and R$_6$ are each, independently, hydrogen, alkyl of 1–6 carbon atoms, cycloalkyl of 3–6 carbon atoms, aryl, heteroaryl or —C$_5$–C$_8$-cycloheteroalkyl;

R$_7$ is hydrogen, aryl, heteroaryl, alkyl of 1–6 carbon atoms or cycloalkyl of 3–6 carbon atoms; and n is 0–2. and n is 0–2.

When a moiety contains more than substituent with the same designation, each of those substituents may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

Also according to the present invention, there are provided processes for producing the compounds of the present invention.

The compounds of the present invention, where n=0, X=O, S or NHR$^7$ and A=S, SO or SO$_2$ may be prepared according to one of the general processes out lined below.

As outlined in scheme 1, the appropriately substituted mercaptan derivative was alkylated using either substituted or unsubstituted a-bromo acetic acid ester derivative in refluxing chloroform using N,N-diisopropylethylamine as base. The sulfide derivative thus obtained was reacted with appropriately substituted propargyl bromide derivative in refluxing acetone using K$_2$CO$_3$ as base. In the case of X=—N—R$^7$ the N-alkylation can be carried out in DMF/NaH at room temperature. The sulfide derivative thus obtained was oxidized using m-chloroperbenzoic acid in CH$_2$Cl$_2$ or by using Oxone in methanol/water. The sulfone obtained from the above mentioned process can be either further alkylated using variety of alkyl halides to obtain the disubstituted derivative or it can be hydrolyzed using NaOH/MeOH at room temp. However instead of using the ethyl ester, if the tertiary butyl ester is present, the hydrolysis can be carried out with TFA/CH$_2$C$_2$ at room temperature. Subsequently, the carboxylic acid obtained was converted to the hydroxamic acid derivative by reaction with oxalyl chloride/DMF (catalytic) and hydroxyl amine/triethyl amine.

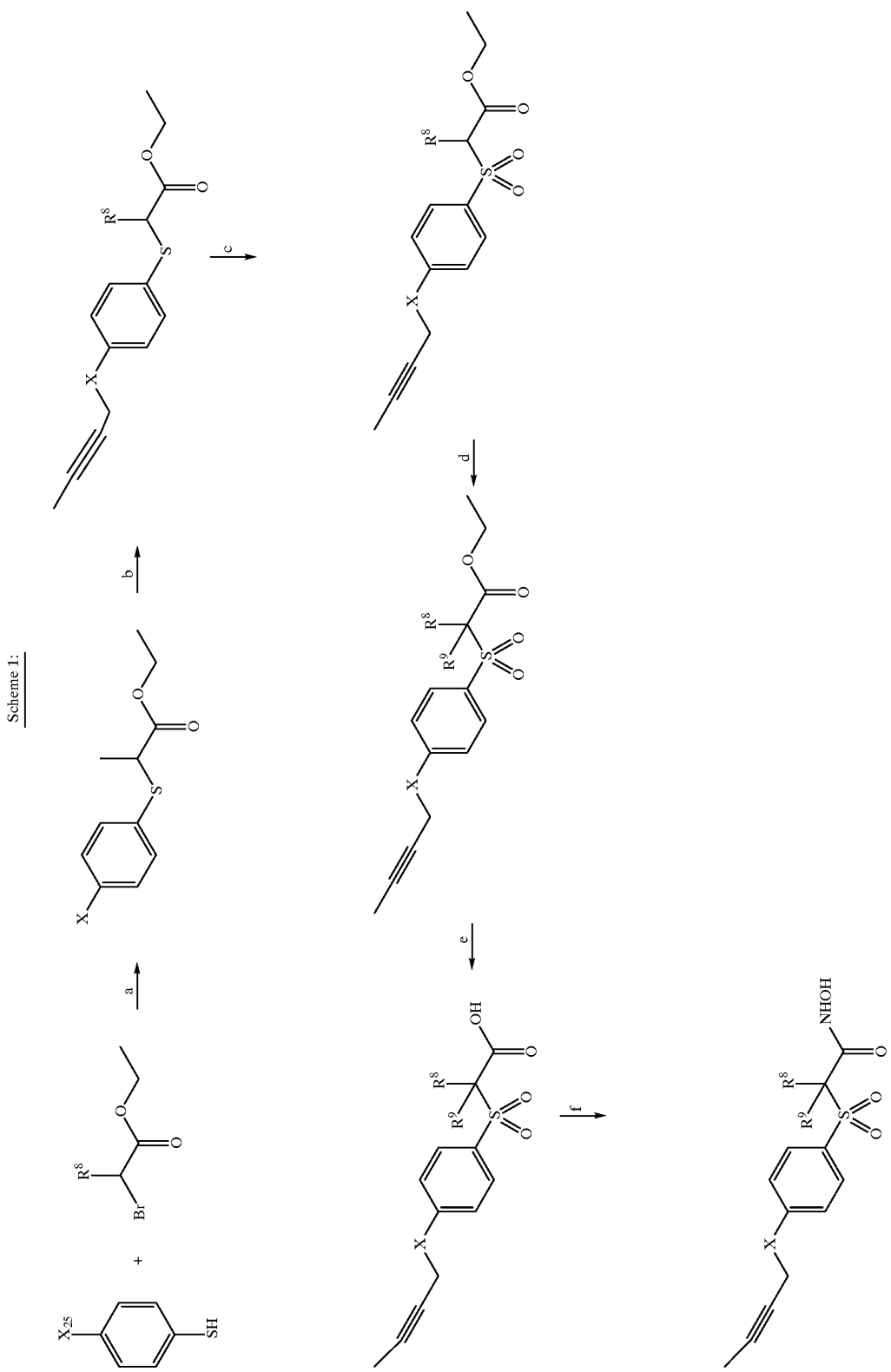
Scheme 1:

a: Et$_3$N/CHCl$_3$/RT; b: Propargyl bromide derivative/ K$_2$CO$_3$/Acetone/Reflux;

c: Oxone/THF:MeOR/RT; d: R$_9$Br/K$_2$CO$_3$/18-Crown-6/ Acetone/Reflux;

e: NaOH/THF:MeOH/RT; f: (COCl)2/DMF/ NH$_2$OH.HCl/Et3N.

As outlined in Scheme 2, the sulfide derivative can be hydrolyzed to carboxylic acid using NaOH/MeOH at room temperature and subsequently converted to the hydroxamic acid derivative as outlined in scheme 1. The mono substituted sulfide derivatives can be further alkylated using potassium bis(trimethylsilyl)amide and the appropriately substituted alkyl halides to form the disubstituted sulfide derivatives. These can be subsequently hydrolyzed and converted to the hydroxamic acid derivative as outlined in scheme 1. The sulfinyl derivatives were prepared by oxidizing the sulfide hydroxamic acid derivatives with 30% H$_2$O$_2$ in methanol at room temperature Scheme 2:

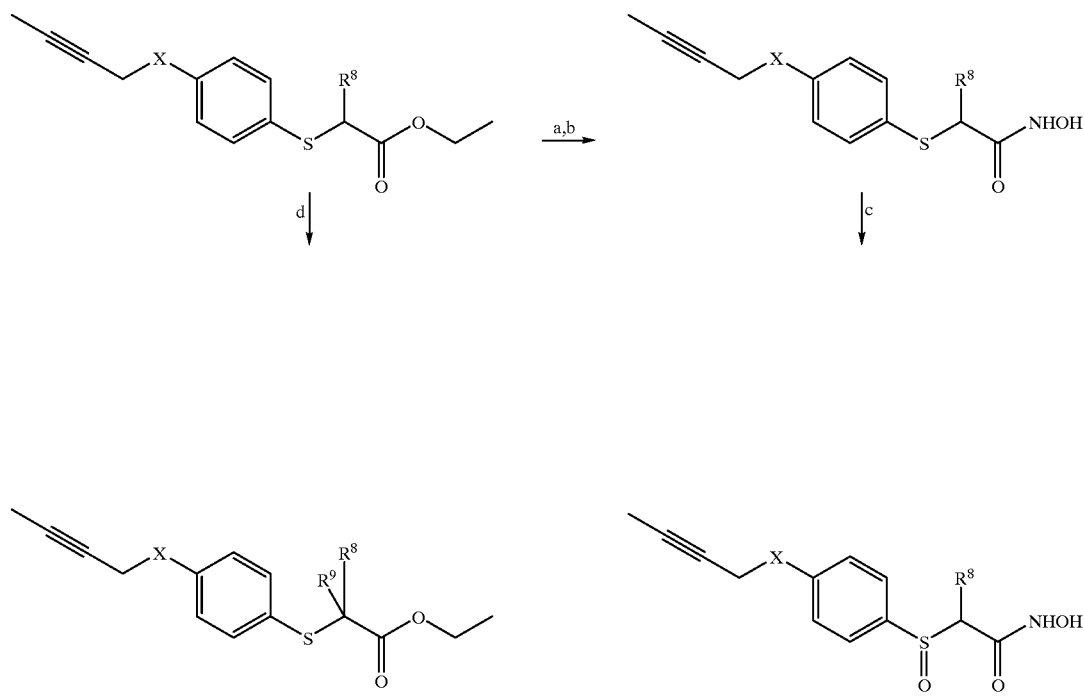

a: NaOH/THF:MeOH/RT; b: (COCl)2/NH$_2$OH.HCl/ Et$_3$N; c: H$_2$O$_2$/MeOH/RT;

d: KN[Si(CH$_3$)$_3$]$_2$/THF/R$^9$Br

The thiols used as intermediates for the synthesis of compounds of the invention can be made according to Scheme 3. Thus, sulfonic acid salts 1, where XR$_{50}$ is a hydroxy, thiol or substituted amino moiety may be alkylated with acetylenes 2, where J is a suitable leaving group such as halogen mesylate, tosylate, or triflate to give 3. Acetylenes 2 are commercially available or known compounds, or they may be synthesized by known methods by those skilled in the art. The sulfonic acid salts 3 may be converted into the corresponding sulfonyl chloride or other sulfonylating agent 4 by known methods, such as reaction with oxalyl chloride, phosphorus oxychloride or other reagent compatible with substituents R1, R2 and R3, and the acetylene. The sulfonyl chloride 4 can then be reduced to the corresponding thiol 5 using triphenylphosphine in a suitable solvent mixture such as dichloromethane/DMF at a temperature of between −20° C. and 30° C.

Alternatively, disulfide 6 may be converted into di-acetylene 7 by reaction with compounds 2, followed by reduction of the disulfide bond to provide the desired thiols 5. Bisacetylenes 7 may also be converted into thiols 5 via sulfonyl chlorides 4. Alkylation of the phenol, thiophenol, aniline or protected aniline 8 with 2 to give 9, followed by reaction with chlorosulfonic acid provides sulfonic acids 10 which are readily converted into 4 with oxalyl chloride or similar reagents and subsequently reduced to thiols 5. Thiophenols 11 are also precursors to 5 via protection of the thiol with a triphenylmethyl or other suitable protecting group, alkylation of XH, where X is O, N or S, and deprotection of the sulfur.

Scheme 3

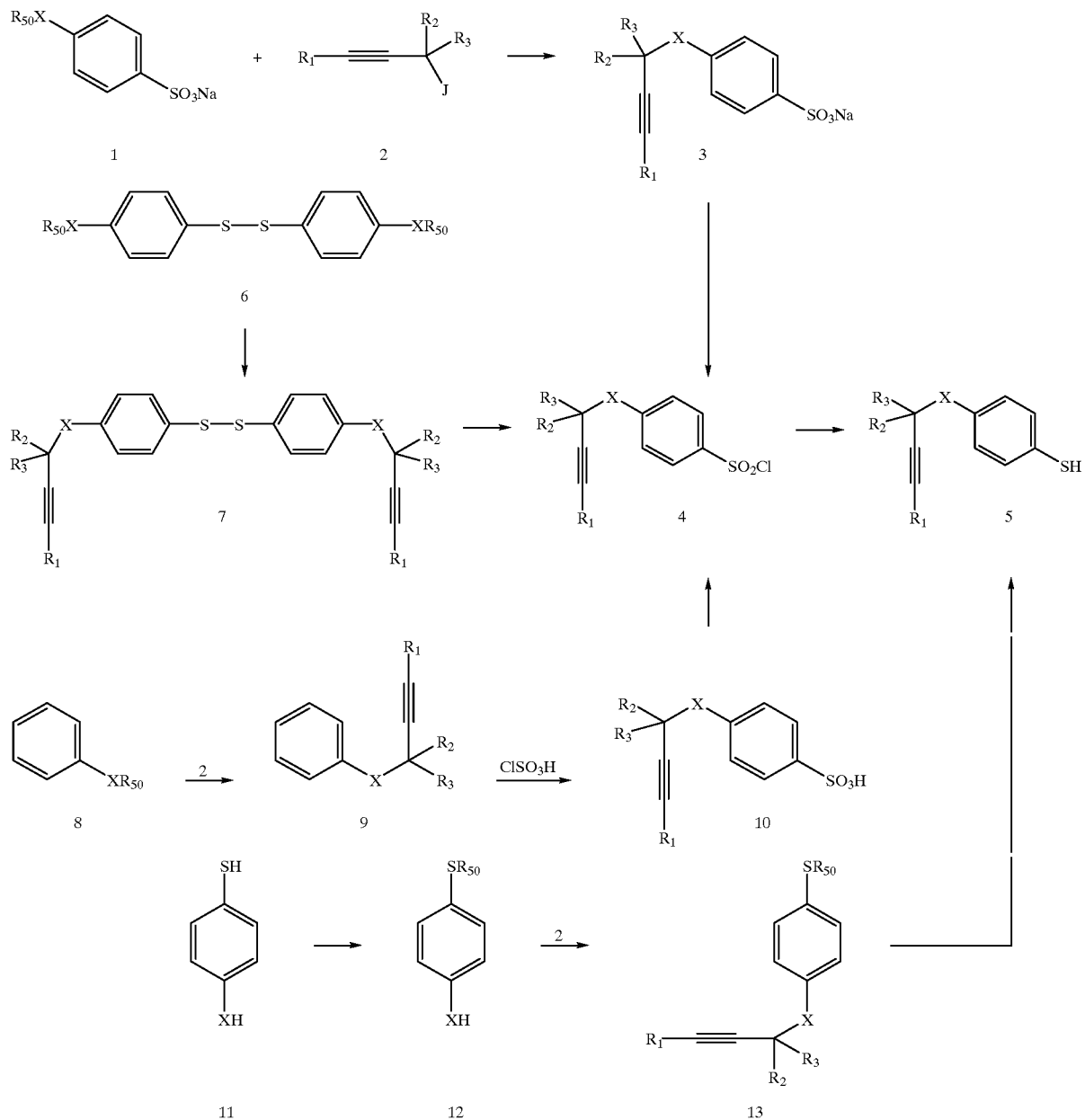

Compounds of the invention wherein X is N, O, S, SO or $SO_2$, can be synthesized according to Scheme 4 and Scheme 5. Alkylation of the para-disubstituted aryl 14, or its protected equivalent, with acetylene 2 in the presence of a base such as potassium carbonate in a polar aprotic solvent such as acetone or DMF at a temperature of between 20° C. and 120° C. provides the mono-propargylic ether 15. Those skilled in the art will recognize that protecting groups may be required to avoid undesirable side reactions and increase the yield of the reaction. The need and choice of protecting group for a particular reaction is known to those skilled in the art. Reaction of this compound with .-propiolactone, or a substituted propiolactone derivative (wherein the substituents have been omitted from the Scheme for clarity), in the presence of a base such as potassium t-butoxide in a polar solvent, or solvent mixture, such as THF or DMF affords the carboxylic acid 16. Conversion of carboxylic acid 16 into the corresponding hydroxamic acid, 17, is accomplished via formation of an activated ester derivative such as an acid chloride or acid anhydride followed by reaction with hydroxylamine. It is understood by those skilled in the art that when A is sulfur, in Scheme 4 and all relevant subsequent Schemes, the sulfur can be oxidized to the corresponding sulfoxide or sulfone at any stage after formation of the thioether, using a suitable oxidant such as oxone, air, m-chloroperbenzoic acid or hydrogen peroxide.

Compounds 17 are also accessible from the Michael addition of compound 15 to an acrylate ester, or substituted acrylate ester (substituents have been omitted from the Scheme for clarity), to provide 18, in which $R_{,,}$ is hydrogen or a suitable carboxylic acid protecting group. Deprotection of the ester moiety then provides carboxylic acid 16 which can be converted into the analogous hydroxamic acid, 17. Similarly, Michael addition of mono-protected 1,4-disubstituted aryl 19, where $ZR_{25}$ is hydroxy or protected hydroxy, thiol or amine, gives compound 20. Unmasking of the protecting group gives thiol, aniline or phenol 21 which can be alkylated with propargyl derivative 2 to provide 18. Mono-protected compound 19 can also be reacted with b-propiolactone to provide 22. Esterification of 22 gives 20, which can then be converted into compounds 17 of the invention. Alternatively, 22 can be deprotected followed by alkylation to give 16 or 18.

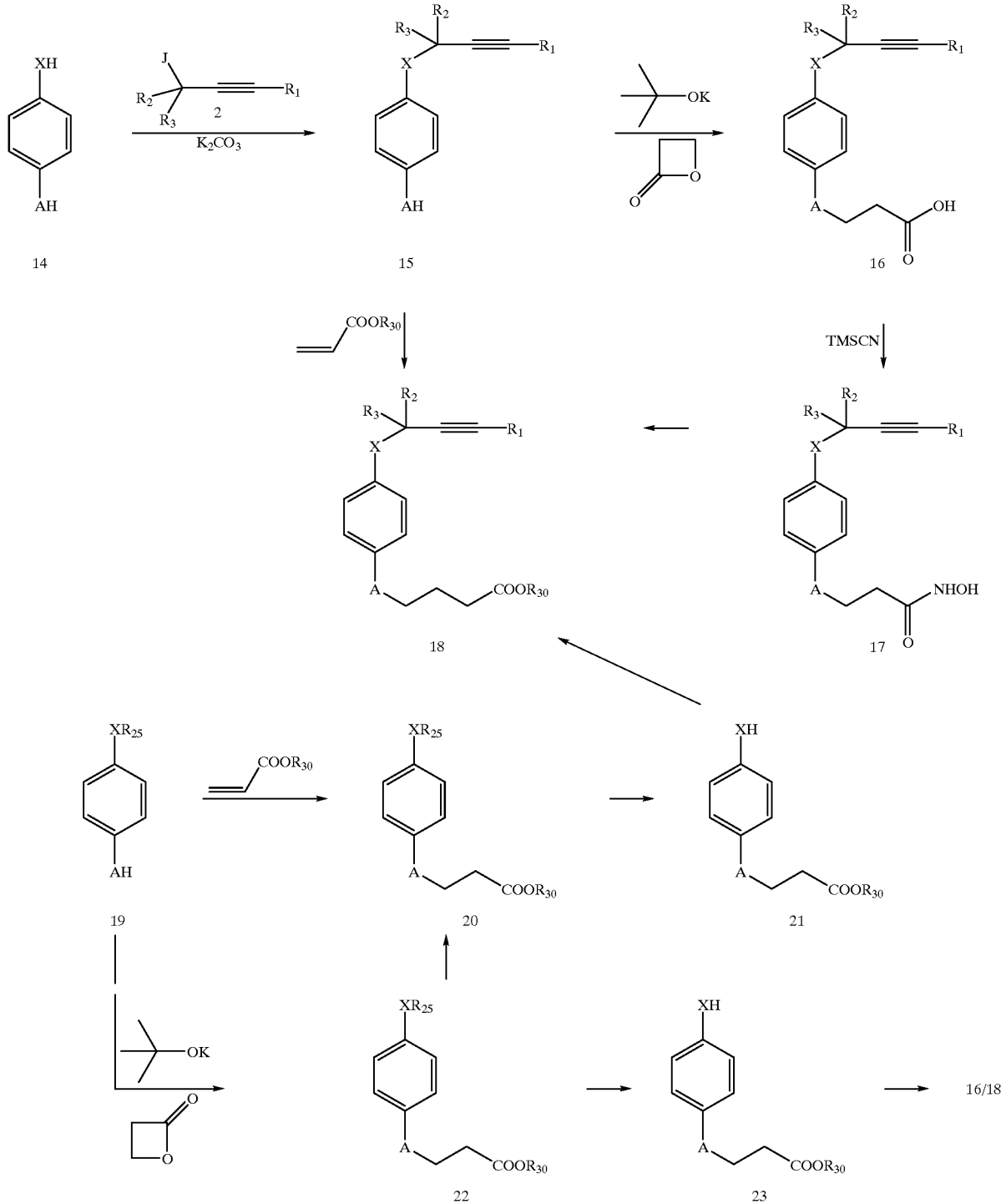

Scheme 4

Synthesis of compounds of the invention wherein X is N, O, S, SO or $SO_2$, and the linker between the proximal heteroatom and the hydroxamic acid is a one or three carbon chain can be synthesized according to Scheme 5. Compound 19, where $XR_{25}$ is hydroxy or protected hydroxy, thiol or amine, can react with ester 24 or lactone 24a, in which $R_{30}$ is hydrogen or a suitable carboxylic acid protecting group, with an appropriately substituted leaving group such as halogen, tosylate, mesylate or triflate, to provide 25. Unmasking of the heteroatom X of compound 25 then provides 26, which may next be alkylated with propargylic derivative 2 to give acetylene-ester 27. Ester 27 can be converted into the corresponding hydroxamic acid 28 through conversion of the ester into the carboxylic acid by acid or base hydrolysis, followed by conversion into the hydroxamic acid as described in Scheme 4. Alternatively, 5compound 15, prepared as shown in Scheme 2, can be alkylated directly with ester 24 or lactone 24a to give 27 and then 28. Substituents on the carbon alpha to the hydroxamic, though omitted from the Scheme for clarity, may be appended through deprotonation and quenching of compounds 25 or 27 with an appropriate electrophile.

Scheme 5

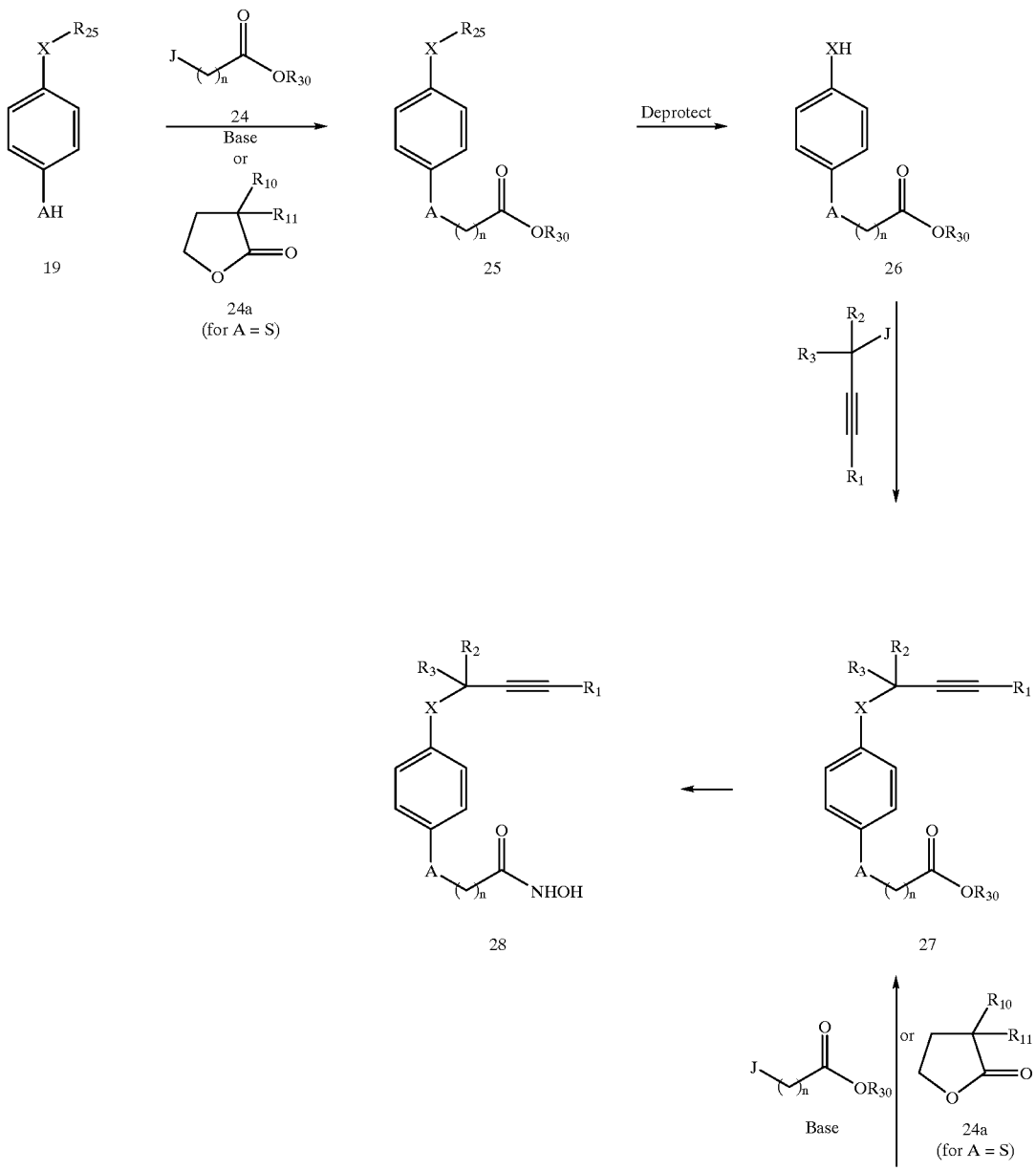

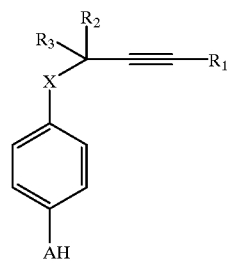

15

Compounds of the invention wherein A is a methylene or substituted methylene group, and X is oxygen, can be obtained according to Scheme 6. Esters or carboxylic acids 29, commercially available or known in the literature, can be converted into the corresponding phenols, 30. Alkylation of the phenol with acetylene 2 gives the propargylic ethers, 31, which can be converted into the corresponding carboxylic acids and thence the hydroxamic acids, 33, as described in Scheme 4. Substituents on the carbon alpha to the hydroxamic, though omitted from the Scheme for clarity, may be appended through deprotonation and quenching of compounds 29 or 31 with an appropriate electrophile.

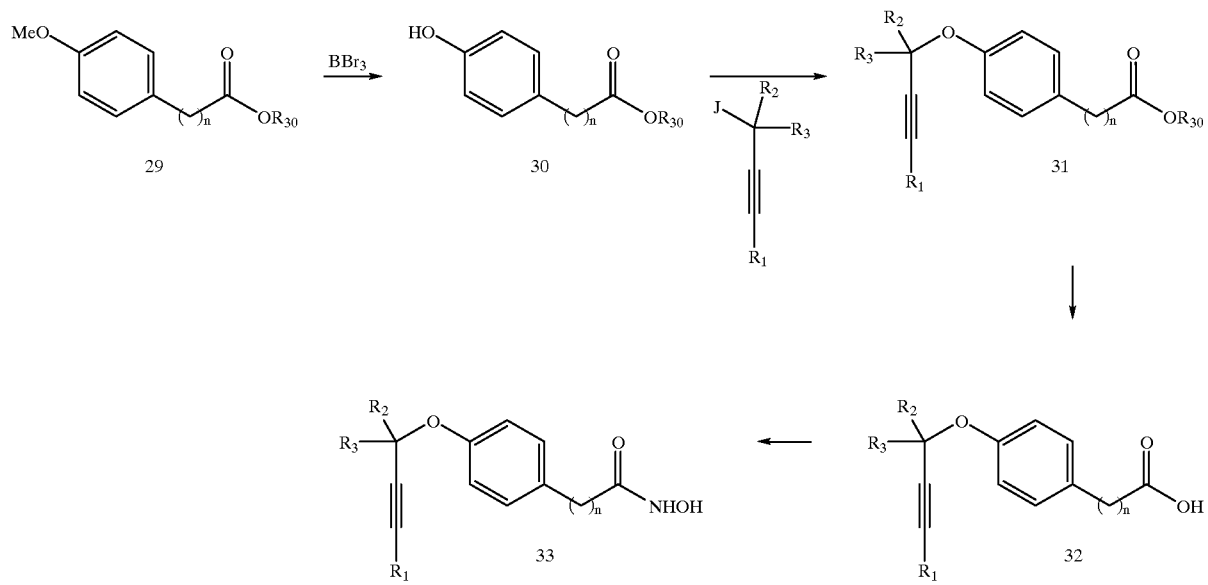

Scheme 6

Compounds of the invention wherein A is —SO$_2$—, and R$_8$ and R$_9$ are not hydrogen, are available stating from 4-fluorobenzenethiol 34 as shown in Scheme 7. Deprotonation of the thiol followed by reaction with p-propiolactone, or an acrylate ester, or ester deriavtive 24, and subsequent oxidation of the resulting thioether provides sulfone-acid 35. Displacement of the 4-fluoro substituent of 35, or its corresponding ester, with propargyl derivative 36, wherein X is N, O or S, then provides sulfone 16. Compound 16 can be converted into the compounds of the invention according to Scheme 4. Fluoroaryl 35 can also react with a masked hydroxyl, thiol or amino group (HXR$_{40}$, wherein R$_{40}$ is a suitable protecting group) in the presence of a base such as sodium hydride in a polar aprotic solvent such as DMF to provide 36. Deprotection of 36 followed by alkylation with acetylenic derivative 2 then gives 16.

Scheme 7

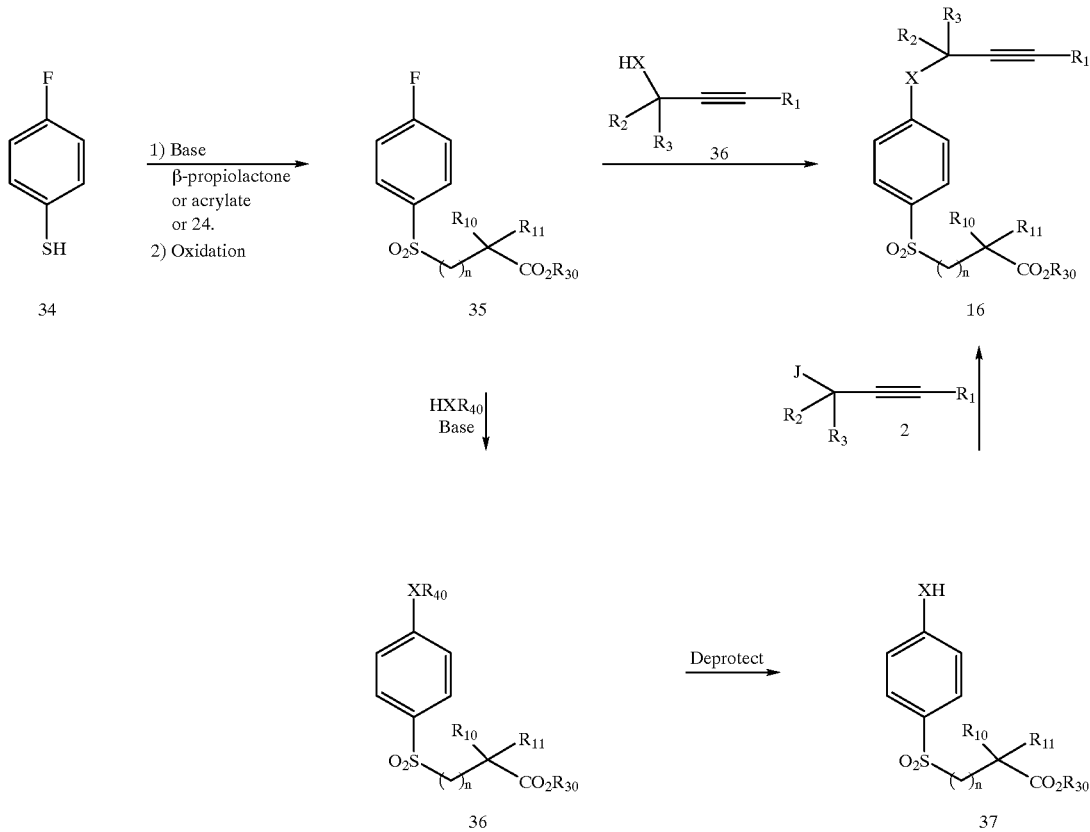

Compounds of the invention wherein X is NH are also available starting from the appropriate commercially available nitro aryl compound 38. Thus, the anion of compound 38 can be used to alkylate.-propiolactone, or a substituted derivative, or an acrylate ester to provide 39. Reduction of the nitro group followed by alkylation of the resulting aniline then gives 16. Compound 38 can also be alkylated with ester derivative 24 to afford nitro-ester 40, followed by reduction to give the corresponding aniline, analogous to compound 26 of Scheme 5.

Scheme 8

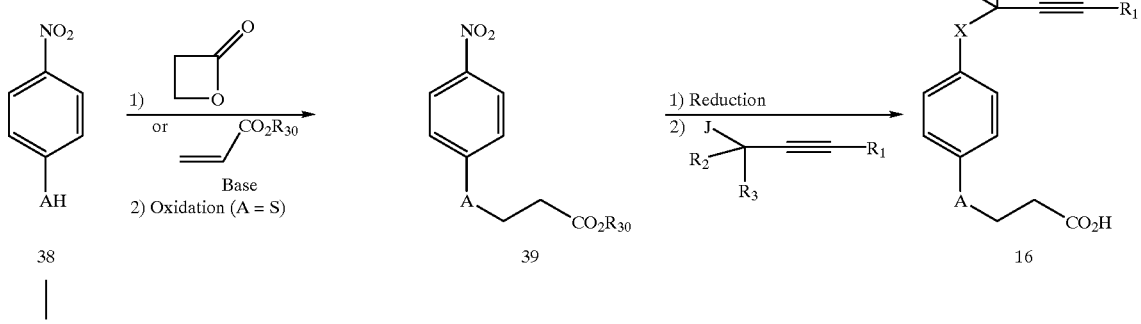

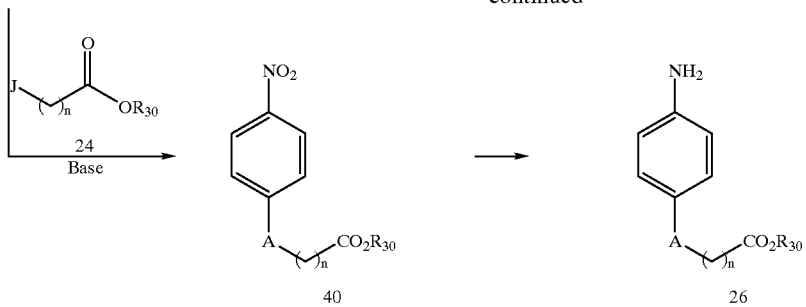

Compounds of the invention wherein $R_{11}$, alpha to the hydroxamic acid, is a hydroxy group can be obtained via epoxides 41, as shown in Scheme 9. These epoxides are available through the oxidation of the corresponding acrylate esters or by the Darzens reaction of an alpha-halo ester with an aldehyde or ketone. Reaction of the epoxide with thiol, phenol or aniline 19 in the presence of base provides alpha-hydroxy ester 42. Deprotection of 42 followed by alkylation with propargyl derivative 2 gives 44. Conversion of the ester of 44 into the analogous hydroxamic acid as described in Scheme 4 then provides 45. Compounds 45, wherein A is sulfur, may be converted into the analogous sulfoxides or sulfones through oxidation with hydrogen peroxide, air, Oxone or other suitable reagent at this point. Similarly, thiol, phenol or aniline 15 can be reacted with 41 to give 44. The hydroxyl group of compound 43 can also be manipulated through its conversion into a suitable leaving group, such as halide or sulfonate ester, followed by displacement with various nucleophiles including amines to provide 44.

Scheme 9

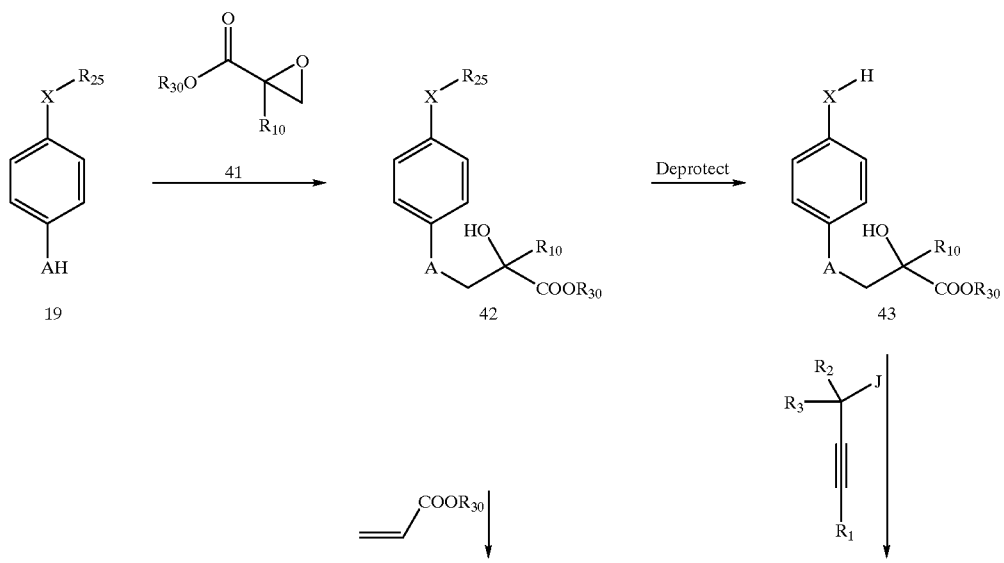

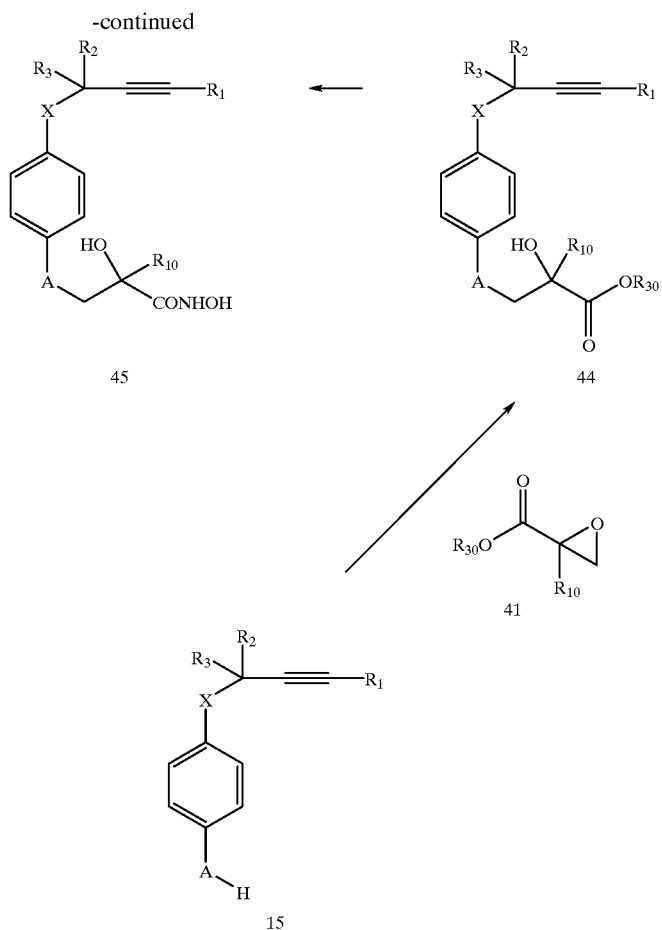

Another route to alpha-hydroxy hydroxamic acids of the invention is shown in Scheme 10. Compound 15 can be alkylated with alcohol 46 to give 47. Oxidation of the alcohol, with or without concomitant oxidation of the thioether (for A=S), gives the aldehyde 48. Reaction of aldehyde 48 with trimethylsilyl cyanide or other suitable reagent then provides the cyanohydrin 49. Hydrolysis of the nitrile of 49 into the corresponding carboxylic acid followed by conversion into the hydroxamic acid as described in Scheme 4 gives 50.

Scheme 10

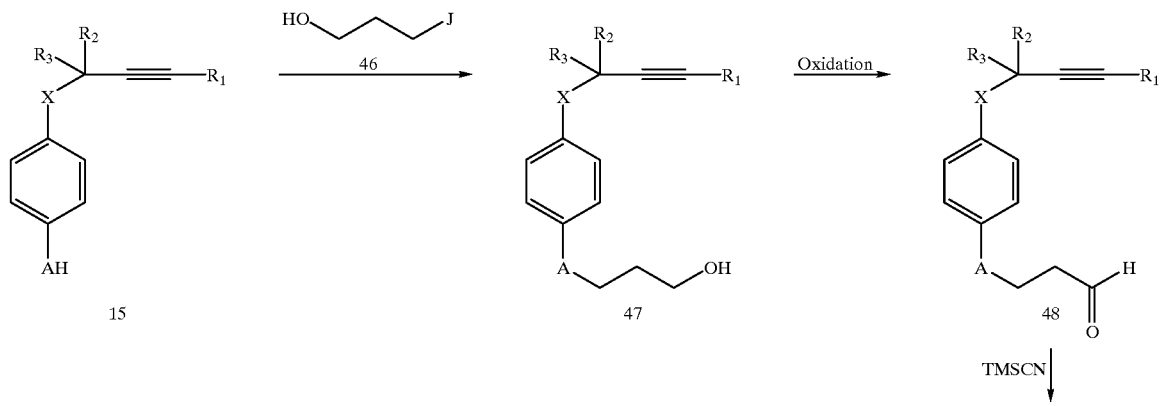

-continued

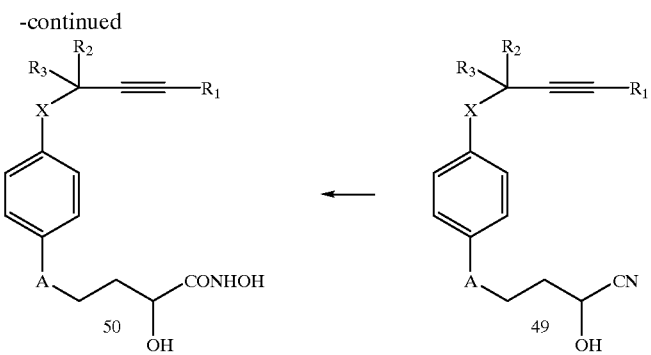

Scheme 11 shows alternative methods for the preparation of hydroxamic acid compounds using a solid phase support.

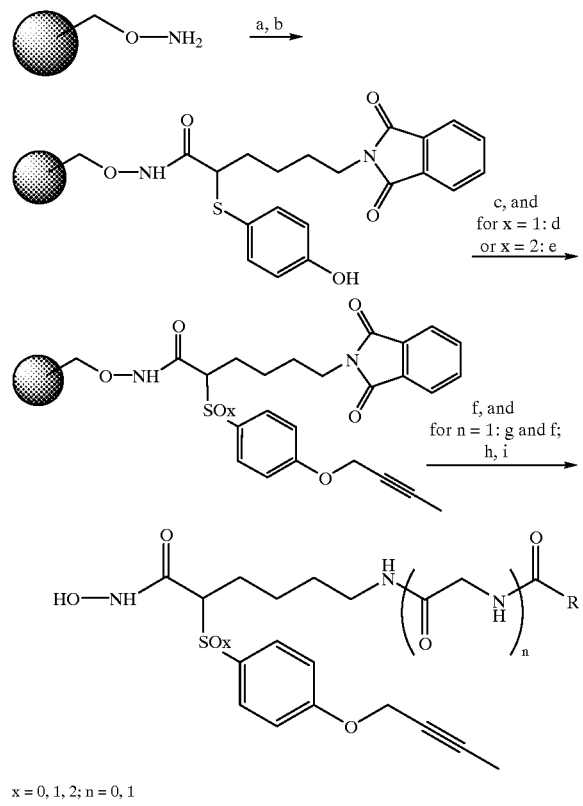

x = 0, 1, 2; n = 0, 1

Scheme 11
Reagents and Conditions: a) 2-bromo-6-phthaloyl caproic acid, DIC, HOBt, DMF; b) p-hydroxybenzenethiol, DBU, NaI, THF; c) 2-bromobutyne, NaH, THF; d) 70% t-butyl hydroperoxide, benzenesulfonic acid, DCM; e) mCPBA, DCM; f) Hydrazine, THF, EtOH; g) N-phthaloyl glycine, DIC, HOBt, DMF; h) RCOOH, DIC, HOBt, DMF; i) TFA, DCM.

The 4-O-methylhydroxylamine-phenoxymethyl-copoly(styrene-1%-divinylbenzene)-resin (hydroxylamine resin) may be coupled with 2-bromo-6-phthaloyl caproic acid to give the hydroxyamide resin. The coupling reaction may be carried out in the presence of carbodiimide, such as DIC, in an inert solvent such as DMF at room temperature. The bromide group may be displaced with hydroxybenzene thiol in the presence of a base, such as DBU, in an inert solvent such as THF at room temperature. The sulfide may be oxidized to the sulfoxide by reaction with an oxidizing agent such as tert-butylhydroperoxide in the presence of an acid catalyst such as benzenesulfonic acid, in an inert solvent such as DCM at room temperature. Alternatively, the sulfide may be oxidized to the sulfone by reaction with an oxidizing agent such as meta-chloroperoxybenzoic acid, in an inert solvent such as DCM at room temperature. The phthaloyl protection group may be removed by reaction with hydrazine in a solvent such as ethanol or THF. The free amine may then be extended by a glycine spacer by reaction with N-phthaloyl glycine in the presence of carbodiimide, such as DIC, in an inert solvent such as DMF at room temperature. Once again the phthaloyl protecting group may be removed by reaction with hydrazine in a solvent such as ethanol or THF. The free amine may be acylated by reaction with an acid in the presence of carbodiimide, such as DIC, in an inert solvent such as DMF at room temperature. The sulfide, sulfoxide, or sulfone may be treated with and acid, such as trifluoroacetic acid, in an inert solvent such as DCM to liberate the free hydroxamic acid.

Scheme 12

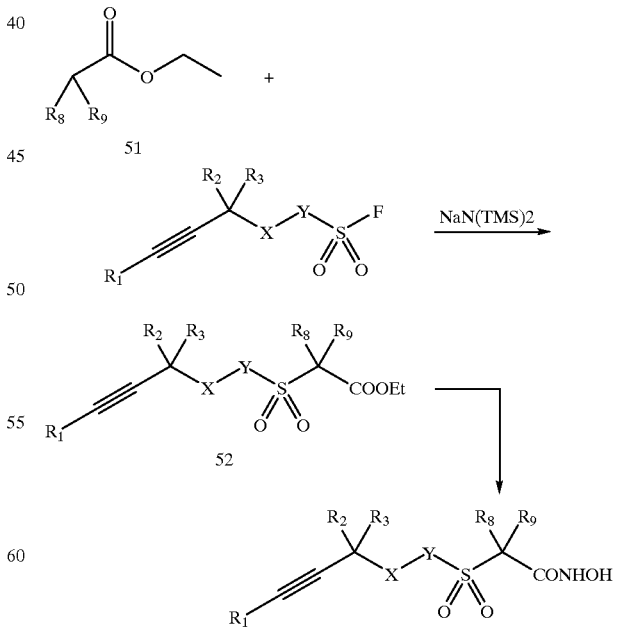

Scheme 12 illustrate an alternate route to alpha-substituted, (where $A=SO_2$ and n=0) hydroxamic acid derivatives. Reaction of 51 with substituted sulfonyl fluorides can give α-sulfonyl ester derivatives 52 and subsequently they can be converted to their respective hydroxamic acid derivatives.

The following examples are presented to illustrate rather than limit the scope of the invention.

EXAMPLE 1

Preparation of 2-(4-But-2-ynyloxy-benzenesulfonyl)-N-hydroxy-2-methyl-3-[4 (2-piperidin-1-yl-ethoxy)-phenyl]-propionamide Step 1

To a stirred solution of 4-mercaptophenol (12.6 g. 100 mmol) and diisopropylethylamine (13.0 g, 101 mmol) in chloroform (200 ml) ethyl 2-bromopropionate (18.2 g, 100 mmol) was added slowly in chloroform (50 ml) solution. The reaction mixture was kept at gentle reflux during the addition. After the addition of ethyl 2-bromo-propionate, reaction mixture was refluxed for two hours and cooled to room temperature. The reaction mixture was washed with water and extracted with chloroform. It was dried over $NA_2SO_4$; filtered and concentrated. The product, 2-(4-hydroxy-phenylsulfanyl)-propionic acid ethyl ester was taken to next step with out purification. Colorless oil; Yield 22.0 g (97%); MS: 227 $(M+H)^+$.

Step 2

A mixture of 2-(4-hydroxy-phenylsulfanyl)-propionic acid ethyl ester(22.6 g, 100 mmol), 1-bromo-2-butyne (13.2 g, 100 mmol) and anhydrous $K_2CO_3$ (50 g, excess) was refluxed in acetone (300 ml) for 8 hrs. After there action was complete, it was cooled to room temperature and filtered. Acetone layer was removed by distillation and the residue was extracted with chloroform, washed well with water; dried and concentrated. 2-(4buty-2-ynyloxy-phenylsulfanyl)-propionic acid ethyl ester was isolated as colorless oil; Yield 26.0 g 93%; MS: 279 $(M+H)^+$.

Step 3

To a stirred solution of 2-(4buty-2-ynyloxy-phenylsulfanyl)-propionic acid ethyl ester (2.78 g, 10 mmol) in methanol: THF (3:1) (100 ml) oxone(10 g, excess) was added in water (25 ml) at room temperature. The reaction mixture was stirred at room temperature for 8 hrs and filtered. Organic layer was removed under reduced pressure and the 2-(4buty-2-ynyloxy-phenylsulfonyl)-propionic acid ethyl ester was isolated as colorless oil. Yield 3.0 g (96%); MS: 311 $(M+H)^+$.

Step 4

A mixture of 2-(4-buty-2-ynyloxy-phenylsulfonyl)-propionic acid ethyl ester (3.1 g, 10 mmol), 4-(2-piperdin-1-yl-ethoxy)-benzyl chloride, hydrochloride (2.9 g, 10 mmol), 18-crown-6 (500 mg), tetrabutylammonium bromide (500 mg) and $K_2CO_3$ (10 g, excess) was refluxed in acetone (200 ml) for 8 hrs. At the end, reaction mixture was cooled to room temperature, filtered and concentrated. The residue was extracted with chloroform, washed well with water; dried and concentrated. The crude product was purified by column chromatography by eluting it with 70% ethyl acetate; hexane. 2-(4-Buty-2-ynyloxy-phenylsulfonyl)-2-methyl-3-[4-(2-piperidin-1-yl-ethoxy)-phenyl]propionic acid ethyl ester was isolated as red oil. Yield 3.2 g, (60%); MS: 528 $(M+H)^+$ Step 5

To stirred solution of 2-(4-Buty-2-ynyloxy-phenylsulfonyl)-2-methyl-3-[4-(2-piperidin-1-yl-ethoxy)-phenyl]propionic acid ethyl ester (3.0 g, 5.4 mmol) in THF:MeOH (1:1) (100 ml), 10 N. NaOH (10 ml) was added at room temperature. The reaction mixture was heated to 60° C. for 24 hours. The reaction mixture was concentrated and carefully neutralized with 5N HCl and extracted with chloroform. The product, was washed well with water and dried over anhydrous $Na_2SO_4$ and concentrated. 2-(4-Buty-2-ynyloxy-phenylsulfonyl)-2-methyl-3-[4-(2-piperidin-1-yl-ethoxy)-phenyl]propionic acid was isolated as yellow solid. Mp. 84° C.; Yield 2.0 g (74%); MS: 500 $(M^+H)$.

Step 6

To a stirred solution of 2-(4-Buty-2-ynyloxy-phenylsulfonyl)-2-methyl-3-[4-(2-piperidin-1-yl-ethoxy)-phenyl]propionic acid (4.99 g, 10 mmol) and DMF (4 ml) in methylene chloride (100 ml), oxalyl chloride (6.3 g, 50 mmol) was added slowly at 0° C. in methylene chloride solution. After the addition was complete, reaction mixture was stirred at room temperature for 1 hour. In a separate flask, $NH_2OH$. HCl (3.5 g, 50 mmol) was dissolved in DMF (20 ml) and $Et_3N$ (10 g, 100 mmol) was added. The reaction mixture was diluted with acetonitrile (25 ml) and cooled to 0° C. The acid chloride prepared in the separate flask was concentrated to remove the excess oxalyl chloride and redissolved in 100 ml methylene chloride added slowly to $NH_2OH$. Reaction mixture was stirred at room temperature for 24 hours and concentrated under reduced pressure. The residue obtained was extracted with chloroform; washed well with water; dried over anhydrous $Na_2SO_4$. Chloroform layer was filtered and concentrated. The product obtained was purified by silica-gel column chromatography by eluting it with 10% methanol; chloroform. 2-(4-Buty-2-ynyloxy-phenylsulfonyl)-N-hydroxy-2-methyl-3-[4-(2-piperidin-1-yl-ethoxy)-phenyl]-propionamide thus isolated was converted to its hydrochloride salt by reacting it with methanolic hydrogenchloride. Colorless solid, Mp. 114–116° C.; Yield 4.5 (87%); MS: 515 $(M^+H)$.

EXAMPLE 2

3-Biphenyl-4-yl-2-(4-Buty-2-ynyloxy-phenylsulfonyl)-N-hydroxy-2-methyl-propionamide 3-Biphenyl-4-yl-2-(4-Buty-2-ynyloxy-phenylsulfonyl)-2-methyl-propionic acid ethyl ester was prepared following the procedure of Example 1 (Step 4). Starting from 2-(4-buty-2-ynyloxy-phenylsulfonyl)-propionic acid ethyl ester (3.1 g, 10 mmol) and 4-phenylbenzyl chloride (20.2 g, 10 mmol), 4.2 g of the product was isolated as yellow oil. Yield (88%); MS: 477 $(M+H)^+$.

3-Biphenyl-4-yl-2-(4-Buty-2-ynyloxy-phenylsulfonyl)-2-methyl-propionic acid was prepared starting from 3-Biphenyl-4-yl-2-(4-Buty-2-ynyloxy-phenylsulfonyl)-2-methyl-propionic acid ethyl ester (4.0 g, 8.4 mmol) dissolved in MeOH (100 ml) and 10 N NaOH (20 ml). The resulting reaction mixture was worked up as outlined in Example 1 (Step 5). Yield 3.2 g (85%); MS: 449 $(M+H)^+$.

Starting from 3-Biphenyl-4-yl-2-(4-Buty-2-ynyloxy-phenylsulfonyl)-2-methyl-propionic acid (3.0 g, 6.7 mmol) and following the procedure as outlined in Example 1 (Step 6) 2.8 g of 3-biphenyl-4-yl-2-(4-Buty-2-ynyloxy-phenylsulfonyl)-N-hydroxy-2-methyl-propionamide was isolated as a colorless solid. Mp. 92–4° C.; Yield 90%; MS: 464 $(M+H)^+$.

EXAMPLE 3

2-(4-Buty-2-ynyloxy-phenylsulfonyl)-N-hydroxy-2-methyl-3-pyridin-3-ylpropionamide 2-(4-Buty-2-ynyloxy-phenylsulfonyl)-2-methyl-3-pyridin-3-yl propionic acid ethyl ester was prepared following the procedure of Example 1 (Step 4). Starting from 2-(4-buty-2-ynyloxy-phenylsulfonyl)-propionic acid ethyl ester (7.0 g, 22.5 mmol) and 3-picolyl chloride hydrochloride (4.5 g, 27.4 mmol), 9.0 g of the product was isolated as yellow oil. Yield (98%); MS: 402 (M+H)$^+$.

2-(4-Buty-2-ynyloxy-phenylsulfonyl)-2-methyl-3-pyridin-3-yl propionic acid was prepared starting from 2-(4-Buty-2-ynyloxy-phenylsulfonyl)-2-methyl-3-pyridin-3-yl propionic acid ethyl ester (8.0 g, 19.9 mmol) dissolved in MeOH (100 ml) and 10 N NaOH (20 ml). The resulting reaction mixture was worked up as outlined in Example 1 (Step 5). Yield 5.1 g (69%); MS: 374 (M+H)$^+$.

Starting from 2-(4-Buty-2-ynyloxy-phenylsulfonyl)-2-methyl-3-pyridin-3-yl propionic acid (6.0 g, 16 mmol) and following the procedure as outlined in Example 1 (Step 6) 4.8 g of 2-(4-Buty-2-ynyloxy-phenylsulfonyl)-N-hydroxy-2-methyl-3-pyridin-3-ylpropionamide was isolated as a colorless solid. The hydrochloride salt was prepared as outlined in example 1. Mp. 154–56° C.; Yield 89%; MS: 389 (M+H)$^+$.

EXAMPLE 4

2-(4-Buty-2-ynyloxy-phenylsulfanyl)-N-hydroxy-propionamide 2-(4-Buty-2-ynyloxy-phenylsulfanyl)-propionic acid was prepared starting from 2-(4-Buty-2-ynyloxy-phenylsulfanyl)-propionic acid ethyl ester (5.56 g, 20 mmol) dissolved in MeOH (100 ml) and 10 N NaOH. The resulting reaction mixture was worked up as outlined in Example 1 (Step 5). Yield 4.8 g (96%); MS: 249 (M–H)$^-$.

Starting from 2-(4-Buty-2-ynyloxy-Phenylsulfanyl)-propionic acid (6.0 g, 24 mmol) and following the procedure as outlined in Example 1 (Step 6) 500 mg of 2-(4-Buty-2-ynyloxy-phenylsulfanyl)-N-hydroxy-propionamide was isolated as a colorless solid. Mp. 102–4° C.; Yield 8%; MS: 266 (M+H)$^+$.

EXAMPLE 5

2-(4-But-2-ynyloxy-benzenelsulfonyl)-octanoic acid hydroxamide 2-(4-Hydroxy-phenylsulfanyl)-octanoic acid ethyl ester was prepared according to the general method as outlined in Example 1 (Step 1). Starting from 4-mercapto phenol(12.6 g 100 mmol) and 2-bromo ethyl octonoate (25.2 g 100 mmol), 25 gms of 2-(4-hydroxy-phenylsulfanyl)-octanoic acid ethyl ester was isolated as colorless liquid. Yield 84%; MS: 297 (M+H)$^+$.

2-(4-But-2-ynyloxy-phenylsulfanyl)-octanoic acid ethyl ester was prepared according to the general method as outlined in Example 1 (Step 2). Starting from 2-(4-hydroxy-phenylsulfanyl)-octanoic acid ethyl ester 13.6 g, 46 mmol) and 1-bromo-2-butyne(6.23 g, 47mmol). Yield 13.78 g (86%); amber oil; MS: 349.0 (M+H)$^+$ 2-(4-But-2-ynyloxy-phenylsulfanyl)-octanoic acid was prepared according to the general method as outlined in Example 1 (Step 5). Starting from 2-(4-but-2-ynyloxy-phenylsulfanyl)-octanoic acid ethyl ester 4.77 g, 13.7 mmol), 4.16 g of product was isolated. Yield 96%; MS: 321.0 (M+H)$^+$ 2-(4-But-2-ynyloxy-benzenesulfonyl)-octanoic acid ethyl ester was prepared according to the general method as outlined in Example 1 (Step 3). Starting from 2-(4-but-2-ynyloxy-phenylsulfanyl)-octanoic acid ethyl ester(7.26 g, 21 mmol) 6.78 g of product was isolated. Yield (85%); Yellow oil; MS 381.2 (M+H)$^+$ 2-(4-But-2-ynyloxy-benzenesulfonyl)-octanoic acid was prepared starting from 2-(4-But-2-ynyloxy-benzenesulfonyl)-octanoic acid ethyl ester (6.52 g, 17mmol) dissolved in THF:Methanol (100: 50 ml) and 10 N NaOH (10 ml). The resulting reaction mixture was worked up as outlined in Example 1 (Step 5). Yield 2.42 g (42%); colorless gum; MS: 352.9 (M+H)$^+$ Starting from 2-(4-but-2-ynyloxy-benzenelsulfonyl)-octanoic acid (2.21 g, 6 mmol) and following the procedure as outlined in Example 1 (Step 6) 270 mg of 2-(4-but-2-ynyloxy-benzenelsulfonyl)-octanoic acid hydroxamide was isolated as a amber gum. Yield 42%; MS: 369.7 (M+H)$^+$; $^1$H NMR (300 MHz, DMSO-d$_6$): δ0.826 (m, 3H), 1.33 (m, 9H), 1.77(s, 3H), 1.89 (d, J=2.2, 1H), 3.03 (d, J=4 Hz, 1(m, 2H), 5.78 (s, 1H) 6.56 (s, 1H), 7.1 (d, 2H), 7.92 (m, 2H).

EXAMPLE 6

2-(4-But-2-ynyloxy-phenylsulfanyl)-octanoic acid hydroxamide 2-(4-But-2-ynyloxy-phenylsulfanyl)-octanoic acid was prepared according to the general method as outlined in Example 1 (Step 5) Starting from 2-(4-but-2-ynyloxy-phenylsulfanyl)-octanoic acid ethyl ester 4.77 g, 13.7 mmol), 4.16 g of product was isolated. Yield 96%; MS: 321.0 (M+H)$^+$ Starting from 2-(4-but-2-ynyloxy-phenylsulfanyl)-octanoic acid (4.12 g, 12.9 mmol) and following the procedure as outlined in Example 1 (Step 6), 2.23 g of 2-(4-but-2-ynyloxy-phenylsulfanyl)-octanoic acid hydroxamide was isolated as a white solid, mp 125° C.; Yield 73%; MS: 335.9 (M+H)$^+$; $^1$H NMR (300 MHz, DMSO-d$_6$): δ0.856 (m, 3H), 1.24 (m, 6H), 1.57(m, 2H), 1.71 (m, 2H), 1.83 (t, 3H), 2.55 (m, 2H), 4.78 (d, 2H) 6.95 (d, 2H), 7.36 (d, 2H), 8.96 (s, 1H), 10.62 (s, 1H).

EXAMPLE 7

(S)-2-{(R)-[4-(2-Butynyloxy)phenylsulfinyl)]}-N-hydroxyoctanamide &

EXAMPLE 8

(S)-2-{(S)-[4-(2-Butynyloxy)phenylsulfinyl)]}-N-hydroxyoctanamide 2-(4-But-2-ynyloxy-phenylsulfanyl)-octanoic acid hydroxamide (prepared in Example 6) (1.78 g, 5 mmol) was dissolved in methanol (50 ml) and H$_2$O$_2$ (30%, 10 ml) was added. The reaction mixture was stirred at room temperature for 96 hours and quenched with ice cold solution of NaHSO$_3$ solution. The reaction mixture was concentrated under reduced pressure and the residue was extracted with chloroform. Examination of the reaction mixture showed the formation of two diastereo isomers and they were separated by silica-gel column chromatography by eluting it with 50% ethyl acetate; hexane. 411 g of (S)-2-[(R)-4-but-2-ynyloxy-phenylsulfinyl)-octanoic acid hydroxamide was isolated as a white solid, mp 132.3° C.; Yield 24%; MS: 352.0 (M+H)$^+$; $^1$H NMR (300 MHz, DMSO-d$_6$): δ0.834 (m, 3H), 1.19 (m, 9H), 1.76 (m, 1H), 1.84(t, 3H), 3.11–3.17 (dd, 2H), 3.33 (t, 3H), 4.81 (d, 2H) 7.15 (d, J=2.8, 2H), 7.36 (d, J=2.3, 2H), 9.00 (s, 1H), 10.56 (s, 1H).

Starting from 2-(4-but-2-ynyloxy-phenylsulfanyl)-octanoic acid hydroxamide (1.78 g, 5.0 mmol) and following the procedure as outlined in Example 7, 0.411 g of (S)-2-[(S)-4-but-2-ynyloxy-phenylsulfinyl)-octanoic acid hydroxamide was isolated as a white solid, mp 112.2° C.; Yield 12%; MS: 352.0 (M+H)$^+$; $^1$H NMR (300 MHz, DMSO-d$_6$): δ0.804 (m, 3H), 1.01 (m, 9H), 1.59(m, 1H), 1.84 (t, 3H), 3.33 (s, 3H), 4.84 (d, 2H) 7.16 (d, J=2.5, 2H), 7.61 (d, J=2.7, 211), 9.21 (s, 1H), 10.82 (s, 1H).

EXAMPLE 9

3-(4-But-2-ynyloxy-phenoxy)-N-hydroxy-propionamide

Step 1
4-But-2-ynyloxy-phenol

To a solution of 4.13 g (0.038 mol) of hydroquinone in 80 mL of acetone was added 5.19 g (0.375 mol) of potassium carbonate and 5.0 g (0.038 mol) of 1-bromo-2-butyne. The resulting mixture was heated at 55–60° C. for 8 h and then stirred overnight at room temperature. The reaction mixture was then poured onto ice and extracted with ether. The combined organics were washed with 1N sodium hydroxide solution. The combined aqueous layers were acidified with 1N HCl solution and extracted with dichloromethane. The dichloromethane layers were washed with water and brine, dried over Na2SO4, filtered through Magnesol® and concentrated in vacuo to provide 2.0 g of the phenol as a brown oil.

Step 2
3-(4-But-2-ynyloxy-phenoxy)-propionic add

To a 0° C. solution of 1.015 g (8.60 mmol) of potassium t-butoxide suspended in 10 mL of dry THF was added a solution of 1.40 g (8.60 mmol) of 4-but-2-ynyloxy-phenol, dissolved in 30 mL of THF/DMF (5:1). The reaction was stirred at room temperature for 10 minutes and then recooled to 0° C. followed by the addition of 0.66 mL (9.46 mmol) of neat .-propiolactone. The resulting mixture was stirred overnight at room temperature and then concentrated in vacuo. The residue was diluted with ethyl acetate and extracted with saturated sodium bicarbonate solution. The alkaline aqueous extracts were acidified to pH2 with concentrated HCl solution and the precipitated solid was collected by filtration, washed with water and dried in vacuo to provide 0.089 g of the carboxylic acid as a black solid; m.p. 88–92° C. Electrospray Mass Spec: 232.9 (M–H)$^-$ Step 3
3-(4-But-2-ynyloxy-phenoxy)-N-hydroxy-propionamide To a 0° C. solution of 0.089 g (0.379 mmol) of 3-(4-but-2-ynyloxy-phenoxy)-propionic acid, dissolved in 1 mL of dichloromethane and 0.059 mL of DMF was added 0.379 mL (0.758 mmol) of a 2M solution of oxalyl chloride. The reaction was warmed to room temperature and stirred for 2 h and then recooled to 0° C. A mixture of 0.139 mL (2.27 mmol) of a 50% hydroxylamine solution, 0.73 mL of THF and 0.21 mL of triethylamine were then added to the reaction. The reaction was stirred at room temperature for 12 h and then concentrated in vacuo. The residue was extracted with dichloromethane and the combined organics were washed with water, 2N citric acid solution and brine, dried over Na$_2$SO$_4$, filtered and concentrated in vacuo. The residue was triturated with ethyl acetate/hexanes to give the hydroxamic acid as a white solid; m.p. 116–118° C. Electrospray Mass Spec: 249.9 (M+H)$^+$

EXAMPLE 10

4-(4-But-2-ynyloxy-phenoxy)-N-hydroxy-butyramide

Step 1
4-(4-Benzyloxy-phenoxy)-butyric acid ethyl ester

To a suspension of 1.2 g (0.030 mol) of 60% sodium hydride in 100 mL of toluene was added 6.12 g (0.030 mol) of 4(benzyloxy)phenol and the reaction was stirred at room temperature for 30 minutes followed by the addition of 5.85 g (0.030 mol) of ethyl 3-bromobutyrate. The resulting mixture was heated to reflux overnight and then filtered. The filtrate was washed with 0.5N sodium hydroxide solution, 3% sodium carbonate solution, water and brine, dried over Na2SO4, filtered and concentrated in vacuo to provide 5.45 g of the bis-ether as a white solid. Electrospray Mass Spec: 314.8 (M+H)$^+$ Step 2
4-(4-Hydroxy-phenoxy)-butyric add ethyl ester To a solution of 3.58 g (0.011 mol) of 4-(4-Benzyloxy-phenoxy)-butyric acid ethyl ester in 200 mL of ethanol was added 0.81 g of 5% palladium on carbon and the resulting mixture was shaken under 35 psi of hydrogen for 4 h. The resulting mixture was filtered through Magnesol® and concentrated in vacuo to provide 1.97 g of the phenol as a grey solid. Electrospray Mass Spec: 225 (M+H)$^+$ Step 3
4-(4-But-2-ynyloxy-phenoxy)-butyric acid ethyl ester To a solution of 524 mg (2 mmol) of triphenylphosphine dissolved in 20 mL of benzene and 50 mL of THF was added 0.175 mL (2.3 mmol) of 2-butyn-1-ol. After five minutes 0.39 g (21.28 mmol) of the 4-(4-hydroxy-phenoxy)-butyric acid ethyl ester, dissolved in 10 mL of THF, was added to the reaction followed by 0.369 mL (2.34 mmol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 0.28 g (58%) of the desired 4-(4-But-2-ynyloxy-phenoxy)-butyric acid ethyl ester as a clear liquid. EI Mass Spec: 276.9 M$^+$ Step 4
4-(4-But-2-ynyloxy-phenoxy)-butyric add To a solution of 0.37 g (1.34 mmol) of 4-(4-But-2-ynyloxy-phenoxy)-butyric acid ethyl ester in 6 mL of THF/methanol (5:1) was added 1.6 mL of 1N sodium hydroxide solution and the resulting mixture was stirred for 1.5 h at 70° C. The reaction mixture was then concentrated in vacuo, triturated with ether, filtered and dried in vacuo to provide 0.36 g of the carboxylate salt as a white solid. Electrospray Mass Spec: 247 (M–H)$^-$ Step 5
4-(4-But-2-ynyloxy-phenoxy)-N-hydroxy-butyramide- According to the procedure of Example 9 (Step 3) 0.36 g (1.33 mmol) of 4-(4-But-2-ynyloxy-phenoxy)-butyric acid provided 0.237 g (68%) of the hydroxamic acid as a white solid; m.p. 123–125° C. Electrospray Mass Spec: 263.9 (M–H)$^-$

EXAMPLE 11

2-(4-But-2-ynyloxy-phenoxy)-N-hydroxy-acetamide (4-But-2-ynyloxy-phenoxy)-acetic add ethyl ester To a suspension of 600 mg (0.015 mol) of 60% sodium hydride in 100 mL of toluene was added 3.0 g (0.015 mol) of 4-(benzyloxy)phenol and the reaction was stirred at room temperature for 30 minutes followed by the addition of 1.61 ml (0.015 mol) of ethyl chloroacetate. The resulting mixture was heated to reflux overnight and then filtered. The filtrate was washed with 0.5N sodium hydroxide solution, 3% sodium carbonate solution, water and brine, dried over Na2SO4, filtered and concentrated in vacuo to provide 2.62 g of the bis-ether as a white solid. M.p. 65–67° C.

To a solution of 2.58 g (8.74 mmol) of the above mentioned product in 200 mL of ethanol was added 0.81 g of 5% palladium on carbon and the resulting mixture was shaken under 35 psi of hydrogen for 4 h. The resulting mixture was filtered through Magnesol® and concentrated in vacuo to provide 1.7 g of the phenol as a grey solid. M.p. 100–105° C.

According to the procedure of Example 10 (Step 3), 1.65 g (8.41 mmol) of the phenol and 0.63 mL of 2-butyn-1-ol provided 1.2 g (60%) of the butynyl ether as a yellow oil. Electrospray Mass Spec: 248.8 (M+H)+
(4-But-2-ynyloxy-phenoxy)-acetic acid According to the procedure of Example 10 (Step 4), 1.0 g (4.00 mmol) of (4-but-2-ynyloxy-phenoxy)-acetic acid ethyl ester provided 0.47 g of the carboxylic acid as a white solid; m.p. 114–116° C. Electrospray Mass Spec: 218.9 (M–H)−
2(4-But-2-ynyloxy-phenoxy)-N-hydroxy-acetamide According to the procedure of Example 9 (Step 3), 0.40 g (1.82 mmol) of (4-But-2-ynyloxy-phenoxy)-acetic acid provided 0.20 g of the hydroxamic acid as a white solid; m.p. 130–132° C. Electrospray Mass Spec: 235.9 (M+H)+

EXAMPLE 12

4-(4-But-2-ynyloxy-phenyl)-N-hydroxy-butyramide
4-(4-But-2-ynyloxy-phenyl)-butyric acid To a solution of 1.00 g (5.15 mmol) of 4-(4-methoxyphenyl)butyric acid in 100 mL of dichloromethane at 0° C. was added 15.5 mL (15.5 mmol) of boron tribromide and the reaction was then allowed to warm to room temperature and stirred for 2 h. The reaction mixture was then poured into 200 mL of saturated sodium bicarbonate solution and the organic layer was separated. The aqueous layer was acidified with concentrated HCl solution and then extracted with dichloromethane. The combined organics were dried over $MgSO_4$, filtered and concentrated in vacuo to provide 0.696 g of impure 4-(4-hydroxyphenyl)butyric acid.

To a solution of 0.69 g of 4-(4-hydroxyphenyl)butyric acid in 10 mL of DMF was added 0.956 g of sodium bicarbonate followed by 0.36 mL of iodomethane and the resulting mixture was stirred at room temperature for 5 h. The reaction was then diluted with water, extracted with ether, dried over $MgSO_4$, filtered and concentrated in vacuo to provide 0.553 g of methyl 4(4-hydroxyphenyl)butyrate.

According to the procedure of Example 10 (Step 3), 0.553 g (2.851 mmol) of methyl 4-(4-hydroxyphenyl)butyrate and 0.256 mL of 2-butyn-1-ol provided 0.294 g of the butynyl ether-methyl ester after chromatography on silica gel eluting with ethyl acetate/hexanes (1:10).

To a solution of 0.294 g (1.195 mmol) of the butynyl ether-methyl ester in 12 mL of THF/methanol (1:1) was added 6.0 mL of 1N sodium hydroxide solution and the resulting mixture was stirred at room temperature for 6 h. The reaction mixture was then acidified with 5% HCl solution, extracted with ethyl acetate, dried over $MgSO_4$ and concentrated in vacuo to provide 0.223 g of the carboxylic acid as a tan solid. Electrospray Mass Spec: 231 (M–H)−
4(4-But-2-ynyloxy-phenyl)-N-hydroxy-butyramide To a solution of 0.189 g (0.815 mmol) 4-(4-but-2-ynyloxy-phenyl)-butyric acid in 4.3 mL of DMF was added 0.132 g (0.978 mmol) of 1-hydroxy benzotriazole followed by 0.208 g (1.083 mmol) of 1-[3-(dimethylamino)propyl]-3-ethylcarbodiimide hydrochloride and the resulting mixture was stirred at room temperature for 1 h. To the reaction mixture was then added 0.23 mL of 50% aqueous hydroxylamine solution and the reaction was stirred overnight at room temperature. The reaction was then diluted with water and extracted with ethyl acetate. The combined organics were washed with water and saturated sodium bicarbonate, dried over $Na_2SO_2$, filtered and concentrated in vacuo to provide 0.156 g of the hydroxamic acid as a tan solid. Electrospray Mass Spec: 248.0 (M+H)+

EXAMPLE 13

2-(4-But-2-ynyloxy-phenylsulfanyl)-6-12-(1,3dioxo-1,3-dihydroisoindol-2 -yl)-acetylamino]-hexanoic acid hydroxyamide Step A: Coupling of 2-bromo-6-phthaloyl caproic acid to hydroxylamine resin 4-O-Methylhydroxylamine-phenoxymethyl-copoly (styrene-1%-divinylbenzene)-resin[1] (20 g, 1.1 meq/g) was placed in a peptide synthesis vessel (Chemglass Inc. Part Number CG-1866) and suspended in DMF (60 mL). 2-Bromo-N-phthaloyl caproic acid (15 g, 2.0 eq.) 1-hydroxybenzotriazole hydrate (HOBt, 18 g, 6.0 eq.) and 1,3-diisopropyl-carbodiimide (DIC, 14 mL, 4.0 eq.) were added. The reaction was shaken on an orbital shaker at room temperature for 2–16 hours. The reaction was filtered and washed with DMF (3×50 mL). A sample of resin was removed and subjected to the Kaiser test. If the test showed the presence of free amine (resin turned blue) the coupling described above was repeated, otherwise the resin was washed with DCM (3×50 mL), MeOH (2×50 mL), and DCM (2×50 mL). (A wash consisted of addition of the solvent and agitation either by nitrogen bubbling or shaking on the orbital shaker for 1–5 minutes, then filtration under vacuum). The resin was dried in vacuo at room temperature.
Step B: Displacement of bromide with 4-hydroxybenzenethiol The 2-bromo-6-phthaloyl hexanoic acid hydroxyamide resin prepared in Step A (20 g, 1.1 meq/g) was suspended in THF (50 mL). 4-Hydroxybenzenethiol (12 g, 5.0 eq.), sodium iodide (13 g, 5.0 eq.) and 1,8-diazabicyclo[5.4.0] undec-7-ene (DBU, 8.9 mL, 3.0 eq.) were added. The reaction was shaken at room temperature for 12–16 hours. The reaction mixture was filtered and washed with DMF (2×20 mL), DMF:water 9:1 (2×20 mL), DMF (20 mL), MeOH (2×20 ML), and DCM (2×20 mL). The resin was dried in vacuo at room temperature.
Step C: Alkylation with 2-bromobutyne The 2-(4-hydroxy-phenylsulfanyl)-6-phthaloyl hexanoic acid hydroxyamide resin prepared in Step B (20 g, 1.1 meq/g) was suspended in THF (50 mL) and cooled to 0° C. 2-Bromobutyne (8.0 mL, 2.0 eq.) and sodium hydride (2.4 g, 3.0 eq.) were added and the mixture shaken at room temperature overnight. The reaction mixture was filtered and washed with DMF (2×20 mL), MeOH (2×20 mL), and DCM (2×20 mL). The resin was dried in vacuo at room temperature.
Step D: Removal of Phthaloyl Group 2-(4-but-2-ynoxy-phenylsulfanyl)-6-phthaloyl hexanoic acid hydroxyamide resin prepared in Step C (3.4 g, 1.1 meq/g) was suspended in THF (150 mL) and ethanol (150 mL) and hydrazine (30 mL) was added. The reaction mixture was shaken on an orbital shaker at room temperature for 12–24 hours. The reaction was filtered and washed with DCM (2×50 mL), DMF (2×50 mL), MeOH (2×50 mL), and DCM (2×50 mL). The resin was dried in vacuo at room temperature.
Step E: Acylation of the Primary Amine 6-Amino-2-(4but-2-ynoxy-phenylsulfanyl)-hexanoic acid hydroxyamide resin prepared in Step D (0.33 g, 1.1 meq/g) was suspended in DMF (60 mL). N-Phthaloyl glycine (1.5 g, 4.0 eq.) 1-hydroxybenzotriazole hydrate (HOBt, 1.43 g, 6.0 eq.) and 1,3-diisopropyl-carbodiimide (DIC, 0.18 mL, 4.0 eq.) were added. The reaction was shaken on an orbital shaker at room temperature for 2–16 hours. The reaction was filtered and washed with DMF (3×5 mL). A sample of resin was removed and subjected to the Kaiser test. If the test showed the presence of free amine (resin turned blue) the coupling described above was repeated, otherwise the resin was washed with DCM (3×5 mL), MeOH (2×5 mL), and DCM (2×5 mL). The resin was dried in vacuo at room temperature.

Step F: Cleavage of 2-(4-but-2-ynyloxy-phenylsulfanyl)-6-[2-(1,3-dioxo-1,3-dihydro-isoindol-2-yl)-acetylamino]-hexanoic acid hydroxyamide from the resin The 2-(4-but-2-ynyloxy-phenylsulfanyl)-6-[2-(1,3-dioxo-1,3-dihydro-isoindol-2-yl)-acetylamino]-hexanoic acid hydroxyamide resin prepared in Step E (0.33 g, 1.1 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. The crude product was purified by reverse phase HPLC under the following conditions:

Column: ODS-AM, 20mm×50 mm, 5·m particle size (YMC, Inc. Wilmington, N.C.)

| Solvent Gradient | Time | Water | Acetonitrile |
| --- | --- | --- | --- |
| | 0.0 | 95 | 5 |
| | 16 min. | 5 | 95 |

Flow Rate: 22.5 mL/min.

EXAMPLE 13

2(4-But-2-ynyloxy-phenylsulfanyl)-6-[2-(1,3dioxo-1,3-dihydro-isoindol-2-yl)-acetylamino]-hexanoic add hydroxyamide had HPLC retention time$^2$ 4.5 min. and MS$^3$ 510 (M+H).

The following hydroxamic acids compounds are synthesized following the steps in Example 13, and using quinaldic acid, 2-bibenzylcarboxylic acid, 3,4-dichlorophenylacetic acid, 3-quinoline carboxylic acid, 4-(2-thienyl)butyric acid, xanthene-9-carboxylic acid, diphenyl acetic acid, 1-isoquinoline carboxylic acid, N-methylpyrrole-2-carboxylic acid, thianaphthalene-3-acetic acid, or indole-3-acetic acid.

| Example # | Compound name | HPLC retention time$^2$ (min.) | MS$^3$ (M + H) |
| --- | --- | --- | --- |
| 14 | Quinoline-2-carboxylic acid [5-(4-but-2-ynyloxy-phenylsulfanyl)-5-hydroxycarbamoyl-pentyl]-amide | 5.0 | 478 |
| 15 | N-[5-(4-But-2-ynyloxy-phenylsulfanyl)-5-hydroxycarbamoyl-pentyl]-2-phenethyl-benzamide | 5.4 | 529 |
| 16 | 2-(4-But-2-ynyloxy-phenylsulfanyl)-6-[2-(3,4-dichloro-phenyl)-acetylamino]-hexanoic acid hydroxyamide | 5.1 | 511 |
| 17 | Quinoline-3-carboxylic acid [5-(4-but-2-ynyloxy-phenylsulfanyl)-5-hydroxycarbamoyl-pentyl]-amide | 4.1 | 478 |
| 18 | 2-(4-But-2-ynyloxy-phenylsulfanyl)-6-(4-thiophen-2-yl-butyrylamino)-hexanoic acid hydroxyamide | 5.0 | 475 |
| 19 | 9H-Xanthene-9-carboxylic acid [5-(4-but-2-ynyloxy-phenylsulfanyl)-5-hydroxycarbamoyl-pentyl]-amide | 5.3 | 531 |
| 20 | 2-(4-But-2-ynyloxy-phenylsulfanyl)-6-diphenylacetylamino-hexanoic acid hydroxyamide | 5.4 | 517 |
| 21 | Isoquinoline-1-carboxylic acid [5-(4-but-2-ynyloxy-phenylsulfanyl)-5-hydroxycarbamoyl-pentyl]-amide | 4.8 | 478 |
| 22 | 6-(2-Benzo [b]thiophen-3-yl-acetylamino)-2-(4-but-2-ynyloxy-phenylsulfanyl)-hexanoic acid hydroxyamide | 5.0 | 497 |

EXAMPLE 23

Quinoline-2-carboxylic acid {5-(4but-2-ynyloxy-benzenesulfinyl)-5-hydroxycarbamoyl-pentyl]-amide Oxidation of Sulfide to Sulfoxide The 2-(4-but-2-ynoxy-phenylsulfanyl)-6-phthaloyl hexanoic acid hydroxyamide resin prepared in Example 13, Step C (6.7 g, 1.1 meq/g) was suspended in DCM (200 mL) and 70% tert-butylhydroperoxide (45 mL) and benzenesulfonic acid (2 g) were added. The reaction mixture was shaken on an orbital shaker at room temperature for 12–24 hours. The reaction was filtered and washed with DCM (2×50 mL), DMF (2×50 mL), MeOH (2×50 mL), and DCM (2×50 mL). The resin was dried in vacuo at room temperature.

Step B: Removal of the Phthaloyl Group 2-(4-But-2-ynoxy-benzenesulfinyl)-6-phthaloyl hexanoic acid hydroxyamide resin prepared in Step A was deprotected to give 6-amino-2-(4-but-2-ynoxy-benzenesulfinyl)-hexanoic acid hydroxyamide resin according to the procedure in Example 13, Step D.

Step C: Acylation of the Primary Amine

6-Amino-2-(4-but-2-ynoxy-benzenesulfinyl)-hexanoic acid hydroxyamide resin (0.33 g, 1.1 meq/g) prepared in step B was acylated with quinaldic acid (1.2 g, 4.0 eq) according to the procedure in Example 13, Step E to give quinoline-2-carboxylic acid [5-(4-but-2-ynyloxy-benzenesulfinyl)-5-hydroxycarbamoyl-pentyl]-amide resin.

Step D: Cleavage of quinoline-2-carboxylic acid [5-(4-but-2-ynyloxy-benzene-sulfinyl)-5-hydroxycarbamoyl-pentyl]-amide from the resin Quinoline-2-carboxylic acid [5-(4-but-2-ynyloxy-benzenesulfinyl)-5-hydroxy-carbamoyl-pentyl]-amide resin prepared in Step C (0.33 g, 1.1 meq/g) was cleaved according to the procedure in Example 13, Step F to give Example 23: quinoline-2-carboxylic acid [5-(4-but-2-ynyloxy-benzenesulfinyl)-5-hydroxy-carbamoyl-pentyl]-amide as a mixture of diastereomers which had HPLC retention time$^2$ 4.35/4.5 min. and MS$^3$ 494 (M+H).

The following hydroxamic acids compounds are synthesized following the steps in Example 23, and using N-phthaloyl glycine, 2-bibenzylcarboxylic acid, 3,4-dichlorophenylacetic acid, 3-quinoline carboxylic acid, 4(2-thienyl)butyric acid, xanthene-9-carboxylic acid, diphenyl acetic acid, 1-isoquinoline carboxylic acid, N-methylpyrrole-2-carboxylic acid, thianaphthalene-3-acetic acid, or indole-3-acetic

| Example # | Compound name | HPLC retention time[2] (min.) | MS[3] (M + H) |
|---|---|---|---|
| 24 | 2-(4-But-2-ynyloxy-benzenesulfinyl)-6-[2-(1,3-dioxo-1,3-dihydro-isoindol-2-yl)-acetylamino]-hexanoic acid hydroxyamide | 3.97/4.08 | 526 |
| 25 | N-[5-(4-But-2-ynyloxy-benzenesulfinyl)-5-hydroxycarbamoyl-pentyl]-2-phenethyl-benzamide | 4.96/5.02 | 547 |
| 26 | 2-(4-But-2-ynyloxy-benzenesulfinyl)-6-[2-(3,4-dichloro-phenyl)-acetylamino]-hexanoic acid hydroxyamide | 4.6/4.7 | 527 |
| 27 | Quinoline-3-carboxylic acid [5-(4-but-2-ynyloxy-benzenesulfinyl)-5-hydroxycarbamoyl-pentyl]-amide | 3.57/3.68 | 494 |
| 28 | 2-(4-But-2-ynyloxy-benzenesulfinyl)-6-(4-thiophen-2-yl-butyrylamino)-hexanoic acid hydroxyamide | 4.31/4.42 | 491 |
| 29 | 9H-Xanthene-9-carboxylic acid [5-(4-but-2-ynyloxy-benzenesulfinyl)-5-hydroxycarbamoyl-pentyl]-amide | 4.71/4.8 | 547 |
| 30 | 2-(4-But-2-ynyloxy-benzenesulfinyl)-6-diphenylacetylamino-hexanoic acid hydroxyamide | 4.78/4.82 | 533 |
| 31 | Isoquinoline-1-carboxylic acid [5-(4-but-2-ynyloxy-benzenesulfinyl)-5-hydroxycarbamoyl-pentyl]-amide | 4.06/4.23 | 495 |
| 32 | 6-(2-Benzo[b]thiophen-3-yl-acetylamino)-2-(4-but-2-ynyloxy-benzenesulfinyl)-hexanoic acid hydroxyamide | 4.44/4.50 | 513 |
| 33 | 2-(4-But-2-ynyloxy-benzenesulfinyl)-6-(2-1H-indol-3-yl-acetylamino)-hexanoic acid hydroxyamide | 4.0/4.1 | 496 |

EXAMPLE 34

N-[5-(4-But-2-ynyloxy-benzenesulfonyl)-5-hydroxycarbamoyl-pentyl]-2-phenethyl-benzamide Step A: Oxidation of Sulfide to Sulfone The 2-(4-but-2-ynoxy-phenylsulfanyl)-6-phthaloyl hexanoic acid hydroxyamide resin prepared in Example 13, Step C (6.7 g, 1.1 meq/g) was suspended in DCM (200 mL) and mCPBA (8 g) was added. The reaction mixture was shaken on an orbital shaker at room temperature for 12–24 hours. The reaction was filtered and washed with DCM (2×50 mL), DMF (2×50 mL), MeOH (2×50 mL), and DCM (2×50 mL). The resin was dried in vacuo at room temperature.

Step B: Removal of the Phthaloyl Group 2-(4-But-2-ynoxy-benzenesulfonyl)-6-phthaloyl hexanoic acid hydroxyamide resin prepared in Step A was deprotected to give 6-amino-2-(4-but-2-ynoxy-benzenesulfinyl)-hexanoic acid hydroxyamide resin according to the procedure in Example 13, Step D.

Step C: Acylation of the Primary Amine

6-Amino-2-(4-but-2-ynoxy-benzenesulfonyl)-hexanoic acid hydroxyamide resin (0.33 g, 1.1 meq/g) prepared in step B was acylated with 2-bibenzylcarboxylic acid (1.6 g, 4.0 eq) according to the procedure in Example 13, Step E to give N-[5-(4-but-2-ynyloxy-benzenesulfonyl)-5-hydroxycarbamoyl-pentyl]-2-phenethyl-benzamide resin.

Step D: Cleavage of N-[5-(4-but-2-ynyloxy-benzenesulfonyl)-5-hydroxycarbamoyl-pentyl]-2-phenethyl-benzamide from the resin N-[5-(4-But-2-ynyloxy-benzenesulfonyl)-5-hydroxycarbamoyl-pentyl]-2-phenethyl-benzamide resin prepared in Step C (0.33 g, 1.1 meq/g) was cleaved according to the procedure in Example 13, Step F to give Example 34: N-[5-(4-but-2-ynyloxy-benzenesulfonyl)-5-hydroxycarbamoyl-pentyl]-2-phenethyl-benzamide d HPLC retention time[2] 5.0 min. and MS[3] 541 (M+H).

The following hydroxamic acids compounds are synthesized following the steps in Example 34, and using quinaldic acid, N-phthaloyl glycine, 3,4-dichlorophenylacetic acid, 3-quinoline carboxylic acid, xanthene-9-carboxylic acid, diphenyl acetic acid, 1-isoquinoline carboxylic acid, or thianaphthalene-3-acetic acid.

| Example # | Compound name | HPLC retention time[2] (min.) | MS[3] (M + H) |
|---|---|---|---|
| 35 | Quinoline-2-carboxylic acid [5-(4-but-2-ynyloxy-benzenesulfonyl)-5-hydroxycarbamoyl-pentyl]-amide | 4.82 | 510 |
| 36 | 2-(4-But-2-ynyloxy-benzenesulfonyl)-6-[2-(1,3-dioxo-1,3-dihydro-isoindol-2-yl)-acetylamino]-hexanoic acid hydroxyamide | 4.35 | 542 |
| 37 | 2-(4-But-2-ynyloxy-benzenesulfonyl)-6-[2-(3,4-dichloro-phenyl)-acetylamino]-hexanoic acid hydroxyamide | 5.00 | 542 |
| 38 | Quinoline-3-carboxylic acid [5-(4-but-2-ynyloxy-benzenesulfonyl)-5-hydroxycarbamoyl-pentyl]-amide | 3.91 | 510 |
| 39 | 9H-Xanthene-9-carboxylic acid [5-(4-but-2-ynyloxy-benzenesulfonyl)-5-hydroxycarbamoyl-pentyl]-amide | 5.12 | 563 |
| 40 | 2-(4-But-2-ynyloxy-benzenesulfonyl)-6-diphenylacetylamino-hexanoic acid hydroxyamide | 5.16 | 549 |
| 41 | Isoquinoline-1-carboxylic acid [5-(4-but-2-ynyloxy-benzenesulfonyl)-5-hydroxycarbamoyl-pentyl]-amide | 4.49 | 510 |
| 42 | 6-(2-Benzo[b]thiophen-3-yl-acetylamino)-2-(4-but-2-ynyloxy-benzenesulfonyl)-hexanoic acid hydroxyamide | 4.7 | 529 |

EXAMPLE 43

2-(4-But-2-ynyloxy-phenylsulfanyl)-6-{2-[2-(3,4dichloro-phenyl)-acetylamino]-acetylamino}-hexanoic add hydroxyamide.

Step A: Removal of the Phthaloyl Group 2-(4-But-2-ynyloxy-phenylsulfanyl)-6-[2-(1,3-dioxo-1,3-dihydro-isoindol-2-yl)-acetylamino]-hexanoic acid hydroxyamide resin prepared in Example 13, Step E was deprotected to give 6-(amino-acetylamino)-2-(4-but-2-ynoxy-benzenesulfinyl)-hexanoic acid hydroxyamide resin according to the procedure in Example 13, Step D.

Step B: Acylation of the Primary Amine 6-(Amino-acetylamino)-2-(4-but-2-ynoxy-benzenesulfinyl)-hexanoic acid hydroxyamide resin (0.33 g, 1.1 meq/g) prepared in step A was acylated with 3,4 dichlorophenylacetic acid (1.5 g, 4.0 eq) according to the procedure in Example 13, Step E to give 2-(4-But-2-ynyloxy-phenylsulfanyl)-6-{2-[2-(3,4-dichloro-phenyl)-acetylamino]-acetylamino}-hexanoic acid hydroxyamide resin.

Step C: Cleavage of 2-(4-but-2-ynyloxy-phenylsulfanyl)-6-{2-[2-(3,4-dichloro-phenyl)-acetylamino]-acetylamino)-hexanoic acid hydroxyamide from the resin 2-(4-But-2-ynyloxy-phenylsulfanyl)-6-{ 2-[2-(3,4-dichloro-phenyl)-acetylamino]-acetylamino)-hexanoic acid hydroxyamide resin prepared in Step B (0.33 g, 1.1 meq/g) was cleaved according to the procedure in Example 13, Step F to give Example 43: 2-(4-but-2-ynyloxy-phenylsulfanyl)-6-{2-[2-(3,4-dichloro-phenyl)-acetylamino]-acetylamino)- hexanoic acid hydroxyamide which had HPLC retention time[2] 4.94 min. and MS[3] 567 (M+H).

The following hydroxamic acids compounds are synthesized following the steps in Example 43, and using quinaldic acid, N-phthaloyl glycine, 2-bibenzylcarboxylic acid, 3-quinoline carboxylic acid, xanthene-9-carboxylic acid, diphenyl acetic acid, 1-isoquinoline carboxylic acid, N-methylpyrrole-2-carboxylic acid or thianaphthalene-3-acetic acid

| Example # | Compound name | HPLC retention time[2] (min.) | MS[3] (M + H) |
|---|---|---|---|
| 44 | Quinoline-2-carboxylic acid {[5-(4-but-2-ynyloxy-phenylsulfanyl)-5-hydroxycarbamoyl-pentylcarbamoyl]-methyl}-amide | 4.7 | 535 |
| 45 | 2-(4-But-2-ynyloxy-phenylsulfanyl)-60{2-[2-(1,3-dioxo-1,3-dihydro-isoindol-2-yl)-acetylamino]-acetylamino}-hexanoic acid hydroxyamide | 4.36 | 567 |
| 46 | N-{[5-(4-But-2-ynyloxy-phenylsulfanyl)-5-hydroxycarbamoyl-pentylcarbamoyl]-methyl}-2-phenethyl-benzamide | 5.27 | 588 |
| 47 | Quinoline-3-carboxylic acid {[5-(4-but-2-ynyloxy-phenylsulfanyl)-5-hydroxycarbamoyl pentylcarbamoyl]-methyl}-amide | 3.96 | 535 |
| 48 | 9H-Xanthene-9-carboxylic acid {[5-(4-but-2-ynyloxy-phenylsulfanyl)-5-hydroxycarbamoyl-pentylcarbamoyl]-methyl}-amide | 4.94 | 588 |
| 49 | 2-(4-But-2-ynyloxy-phenylsulfanyl)-6-(2-diphenylacetylamino-acetylamino)-hexanoic acid hydroxyamide | 5.09 | 574 |
| 50 | Isoquinoline-1-carboxylic acid {[5-(4-but-2-ynyloxy-phenylsulfanyl)-5-hydroxycarbamoyl-pentylcarbamoyl]-methyl}-amide | 4.52 | 535 |
| 51 | 1-Methyl-1H-pyrrole-2-carboxylic acid {[5-(4-but-2-ynyloxy-phenylsulfanyl)-5-hydroxycarbamoyl-pentylcarbamoyl]-methyl}-amide | 4.33 | 487 |
| 52 | 6-[2-(2-Benzo[b]thiophen-3-yl-acetylamino)-acetylamino]-2-(4-but-2-ynyloxy-phenylsulfanyl hexanoic acid hydroxyamide | 4.80 | 554 |

EXAMPLE 53

Quinoline-3-carboxylic acid [5-(4-but-2-ynyloxy-benzenesulfinyl)-5-hydroxycarbamoyl-pentyl]-amide.

Step A: Oxidation of Sulfide to Sulfoxide 2-(4But-2-ynyloxy-phenylsulfanyl)-6-[2-(1,3-dioxo-1,3-dihydro-isoindol-2-yl)-acetylamino]-hexanoic acid hydroxyamide resin prepared in Example 13, Step E was oxidized to 2-(4-but-2-ynyloxy-benzenesulfinyl)-6-[2-(1,3-dioxo-1,3-dihydro-isoindol-2-yl)-acetylamino]-hexanoic acid hydroxyamide resin according to the procedure in Example 23, Step A.

Step B: Removal of the Phthaloyl Group 2-(4-But-2-ynyloxy-benzenesulfinyl)-6-[2-(1,3-dioxo-1,3-dihydro-isoindol-2-yl)-acetylamino]-hexanoic acid hydroxyamide resin prepared in Step A was deprotected to give 6-(amino-acetylamino)-2-(4but-2-ynoxy-benzenesulfinyl)-hexanoic acid hydroxy-amide resin according to the procedure in Example 13, Step D.

Step C: Acylation of the Primary Amine 6-(Amino-acetylamino)-2-(4but-2-ynoxy-benzenesulfinyl)-hexanoic acid hydroxyamide resin (0.33 g, 1.1 meq/g) prepared in step B was acylated with 3-quinolinecarboxylic acid (1.2 g, 4.0 eq) according to the procedure in Example 13, Step E to give quinoline-3-carboxylic acid [5-(4-but-2-ynyloxy-benzenesulfinyl)-5-hydroxycarbamoyl-pentyl]-amide resin.

Step D: Cleavage of quinoline-3-carboxylic acid [5-(4-but-2-ynyloxy-benzenesulfinyl)-5-hydroxycarbamoyl-pentyl]-amide from the resin Quinoline-3-carboxylic acid [5-(4but-2-ynyloxy-benzenesulfinyl)-5-hydroxycarbamoyl-pentyl]-amide resin prepared in Step C (0.33 g, 1.1 meq/g) was cleaved according to the procedure in Example 13, Step F to give Example 53: quinoline-3-carboxylic acid [5-(4-but-2-ynyloxy-benzenesulfinyl)-5-hydroxy-carbamoyl-pentyl]-amide as a mixture of diastereomers which had HPLC retention 9 min. and MS[3] 551 (M+H).

The following hydroxamic acids compounds are synthesized following the steps in Example 53, and using quinaldic acid, N-phthaloyl glycine, 2-bibenzylcarboxylic acid, 3,4-dichlorophenylacetic acid, 4-(2-thienyl)butyric acid, xanthene-9-carboxylic acid, diphenyl acetic acid, or N-methylpyrrole-2-carboxylic acid.

| Example # | Compound name | HPLC retention time[2] (min.) | MS[3] (M + H) |
|---|---|---|---|
| 54 | Quinoline-2-carboxylic acid [5-(4-but-2-ynyloxy-benzenesulfinyl)-5-hydroxycarbamoyl-pentyl]-amide | 4.19/4.27 | 551 |
| 55 | 2-(4-But-2-ynyloxy-benzenesulfinyl)-6-[2-(1,3-dioxo-1,3-dihydro-isoindo-2-yl)-acetylamino] hexanoic acid hydroxyamide | 3.85/3.90 | 583 |
| 56 | N-[5-(4-But-2-ynyloxy-benzenesulfinyl)-5 hydroxycarbamoyl-pentyl]-2-phenethyl-benzamide | 4.8 | 604 |
| 57 | 2-(4-But-2-ynyloxy-benzenesulfinyl)-6-[2-(3,4-dichloro-phenyl)-acetylamino]-hexanoic acid hydroxyamide | 4.48 | 583 |
| 58 | 2-(4-But-2-ynyloxy-benzenesulfinyl)-6-(4-thiophen-2-yl-butyrylamino)-hexanoic acid hydroxyamide | 3.49/3.56 | 548 |
| 59 | 9H-Xanthene-9-carboxylic acid [5-(4-but-2-ynyloxy-benzenesulfinyl)-5-hydroxycarbamoyl pentyl]-amide | 4.58 | 604 |
| 60 | 2-(4-But-2-ynyloxy-benzenesulfinyl)-6-diphenylacetylamino-hexanoic acid hydroxyamide | 4.65 | 590 |
| 61 | 1-Methyl-1H-pyrrole-2-carboxylic acid {[5-(4-but-2-ynyloxy-benzenesulfinyl)-5-hydroxy carbamoylpentyl-carbamoyl]-methyl}-amide | 3.76/3.85 | 503 |

EXAMPLE 62

2-(4-But-2-ynyloxy-benzenesulfonyl)-6-(2-diphenylacetylamino-acetylamino)-hexanoic add hydroxyamide.

Step A: Oxidation of Sulfide to Sulfone 2-(4-But-2-ynyloxy-phenylsulfanyl)-6-[2-(1,3-dioxo-1,3-dihydro-isoindol-2-yl)-acetylamino]-hexanoic acid hydroxyamide resin prepared in Example 13, Step E was oxidized to 2-(4-but-2-ynyloxy-benzenesulfonyl)-6-[2-(1,3-dioxo-1,3-dihydro-isoindol-2-yl)-acetylamino]-hexanoic acid hydroxyamide resin according to the procedure in Example 34, Step A.

Step B: Removal of the Phthaloyl Group 2-(4-But-2-ynyloxy-benzenesulfonyl)-6-[2-(1,3-dioxo-1,3-dihydro-isoindol-2-yl)-acetylamino]-hexanoic acid hydroxyamide resin prepared in Step A was deprotected to give 6-(amino-acetylamino)-2-(4-but-2-ynoxy-benzenesulfinyl)-hexanoic acid hydroxy-amide resin according to the procedure in Example 13, Step D.

Step C: Acylation of the Primary Amine 6-(Amino-acetylamino)-2-(4-but-2-ynoxy-benzenesulfonyl)-hexanoic acid hydroxyamide resin (0.33 g, 1.1 meq/g) prepared in step B was acylated with diphenylacetic acid (1.5 g, 4.0 eq) according to the procedure in Example 13, Step E to give 2-(4-but-2-ynyloxy-benzenesulfonyl)-6-(2-diphenylacetylamino-acetylamino)-hexanoic acid hydroxyamide resin.

Step D: Cleavage of 2-(4-but-2-ynyloxy-benzenesulfonyl)-6-(2-diphenylacetylamino-acetylamino)-hexanoic acid hydroxyamide from the resin 2-(4-But-2-ynyloxy-benzenesulfonyl)-6-(2-diphenylacetylamino-acetylamino)-hexanoic acid hydroxyamide resin prepared in Step C (0.33 g, 1.1 meq/g was cleaved according to the procedure in Example 13, Step F to give Example 62: 2-(4-But-2-ynyloxy-benzenesulfonyl)-6-(2-diphenylacetylamino-acetylamino)-hexanoic acid hydroxyamide which had HPLC retention time[2] 4.90 min. and MS[3] 606 (M+H).

The following hydroxamic acids compounds are synthesized following the steps in Example 62, and using N-phthaloyl glycine, 2-bibenzylcarboxylic acid, 3,4-dichlorophenylacetic acid, 3-quinolinecarboxylic acid, xanthene-9-carboxylic acid, 1-isoquinoline carboxylic acid, thianaphthene-3-acetic acid, or indole-3-acetic acid.

| Example # | Compound name | HPLC retention time[2] (min.) | MS[3] (M + H) |
|---|---|---|---|
| 63 | 2-(4-But-2-ynyloxy-benzenesulfonyl)-6-{2-[2-(1,3-dioxo-1,3-dihydro-isoindol-2-yl)-acetyl-amino]-acetylamino}-hexanoic acid hydroxyamide | 4.49 | 599 |
| 64 | N-{[5-(4-But-2-ynyloxy-benzenesulfonyl)-5-hydroxycarbamoyl-pentylcarbamoyl]-methyl}-2-phenethyl-benzamide | 4.18 | 620 |
| 65 | 2-(4-But-2-ynyloxy-benzenesulfonyl)-6-{2-[2-(3,4-dichloro-phenyl)-acetylamino]-acetylamino}-hexanoic acid hydroxyamide | 5.08 | 599 |
| 66 | Quinoline-3-carboxylic acid {[5-(4-but-2-ynyloxy-benzenesulfonyl)-5-hydroxy-carbamoyl-pentylcarbamoyl]-methyl}-amide | 4.77 | 567 |
| 67 | 9H-Xanthene-9-carboxylic acid {[5-(4-but-2-ynyloxy-benzenesulfonyl)-5-hydroxy-carbamoyl-pentylcarbamoyl]-methyl}-amide | 3.80 | 620 |
| 68 | Isoquinoline-1-carboxylic acid {[5-(4-but-2-ynyloxy-benzenesulfonyl)-5-hydroxy-carbamoyl-pentylcarbamoyl]-methyl}-amide | 4.90 | 567 |
| 69 | 6-[2-(2-Benzo[b]thiophen-3-yl-acetylamino)-acetylamino]-2-(4-but-2-ynyloxy benzenesulfonyl hexanoic acid hydroxyamide | 4.33 | 586 |
| 70 | 2-(4-But-2-ynyloxy-benzenesulfonyl)-6-[2-(2-1H-indol-3-yl-acetylamino)-acetylamino]-hexanoic acid hydroxyamide | 4.61 | 570 |

References

1. Rickter, L. S.; Desai, M. C. *Tetrahedron Letters*, 1997, 38, 321–322.
2. LC conditions: Hewlett Packard 1100; YMC ODS-A 4.6 mm×50 mm 5 u column at 23° C.; 10 uL injection; Solvent A: 0.05% TFA/water; Solvent B:0.05% TFA/acetonitrile; Gradient: Time 0: 98% A; 1 min: 98% A; 7 min: 10% A, 8 min: 10% A; 8.9 min: 98%A; Post time 1 min. Flow rate 2.5 mL/min; Detection: 220 and 254 nm DAD.
3. MS conditions: API-electrospray

EXAMPLE 71

2-{14-(2-butynyloxy)phenyl]sulfonyl}-N-hydroxy-4-{4-12-(1-piperidinyl)ethoxy phenyl}butanamide Step 1

2-[4-(2-Piperidin-1-yl-ethoxy)-phenyl]-ethanol

To a solution of 4-hydroxyphenethyl alcohol (5.02 g, 36.3 mmol) and chloroethyl piperidine (7.36 g, 39.96 mmol) in 30 ml of DMF, 5 g of $K_2CO_3$ was added. The reaction was stirred at 80° C. overnight. After cooling the mixture was quenched with water then extracted in $CHCl_3$. The organic layer was separated, dried over $Na_2SO_4$, filtered and concentrated. 2-[4-(2-Piperidin-1-yl-ethoxy)-phenyl]-ethanol (4.58 g, 18.4 mmol) was isolated as a brown oil; Yield 51%; MS: 250.3 (M+H)$^+$ Step 2

1-{2-[4-(Chloro-ethyl)-phenoxy]-ethyl}-piperidine

2-[4-(2-Piperidin-1-yl-ethoxy)-phenyl]-ethanol (4.23 g, 16.98 mmol) was dissolved in 200 ml of THF. HCl gas was bubbled through the solution at 0° C. for 5 minutes. Still at 0° C. the thionyl chloride (2.48 ml, 33.9 mmol) was added dropwise. The reaction mixture was heated at reflux for 2 hours before it was concentrated. 1-{2-[4-(Chloro-ethyl)-phenoxy]-ethyl}-piperidine (4.74 g, 15.6 mmol) was isolated as a brown semisolid; Yield 92%; MS: 268.3 (M+H)$^+$ Step 3

Ethyl 2-{[4-(2-butynyloxy)phenyl]sulfonyl}-4-{4-[2-(1-piperdinyl) ethoxyphenyl}butanoate was prepared according to the general method as outlined in Example 1 (Step 4) starting from 1-{2-[4-(Chloro-ethyl)-phenoxy]-ethyl}-piperidine (4.74 g, 15.64 mmol) and (4-but-2-ynyloxy-benzenesulfonyl)-acetic acid ethyl ester (3.56 g, 12 mmol); 1.21 g of crude product. Yield 19%; brown oil; MS: 528.1 (M+H)$^+$ Step 4

2-{[4-(2-butynyloxy)phenyl]sulfonyl}-4-{4-[2-(1-piperidinyl) ethoxy]phenyl}butanoic acid was prepared according to the general method as outlined in Example 1 (Step 5). Starting from ethyl 2-{[4-(2-butynyloxy)phenyl]sulfonyl}-4-{4-[2-(1 -piperdinyl) ethoxyphenyl}butanoate (1.21 g, 2.29 mmol), 750 mg off white solid was isolated. Yield 65%; MS: 500.3 (M+H)$^+$ Step 5

Starting from 2-{[4-(2-butynyloxy)phenyl]sulfonyl}-4-{4-[2-(1-piperidinyl) ethoxy]phenyl}butanoic acid (660 mg, 1.32 mmol) and following the procedure as outlined in Example 1 (step 6) 50 mg of 2-{[4-(2-butynyloxy)phenyl] sulfonyl}-N-hydroxy-4-{4-[2-(1-piperidinyl) ethoxyphenyl}butanamide was isolated as a pale yellow solid. mp: 68° C.; Yield 7%; MS: 515.2 (M+H)$^+$; $^1$H NMR (300 MHz, DMSO-d$_6$): δ0.853 (m, 2H), 1.36 (s, 2H), 1.67–1.82 (band, 4H), 1.84 (s, 3H), 1.95 (q, 2H), 2.94 (m, 2H), 3.45 (m, 4H), 3.73 (t, 1H), 4.33 (t, J=4.41 Hz, 2H), 4.88 (d, 2.25 Hz, 2H), 6.91 (m, 2H), 7.05 (d, 2H), 7.16 (m, 2H), 7.69, (m, 2H), 9.28 (s, 1H), 9.88 (s, 1H).

EXAMPLE 72

2-{[4-(2-butynyloxy)phenyl]sulfonyl}-7-cyano-N-hydroxy heptanamide

Ethyl 2-{[4-(2-butynyloxy)phenyl]sulfonyl}-7-cyanoheptanoate was prepared according to the general method as outlined in example 1 (step 4), starting from (4-but-2-ynyloxy-benzenesulfonyl)-acetic acid ethyl ester (10 g, 33.8 mmol) and 6-bromohexanenitrile (4.48 ml, 33.8 mmol); 7.9 g white solid. mp 63° C.; Yield 60%; MS (EI): 391.4 (M+H)$^+$ 2-{[4-(2-butynyloxy)phenyl]sulfonyl}-7-cyanoheptanoic acid was prepared according to the general method as outlined in example 1 (step 5), starting from ethyl 2-{[4-(2-butynyloxy)phenyl]sulfonyl}-7-cyanoheptanoate (300 mg, 0.77 mmol); 230 mg yellow gel. Yield 82%; MS: 362.4 (M–H)⁻

Starting from 2-{[4-(2-butynyloxy)phenyl]sulfonyl}-7-cyanoheptanoic acid (3.78 g, 10.4 mmol) and following the procedure as outlined in Example 1 (step 6), 1.11 g of 2-{[4-(2-butynyloxy)phenyl]sulfonyl}-7-cyano-N-hydroxy heptanamide was isolated as a white powder. mp: 120° C.; Yield: 28%; MS: 379.3 (M+H)⁺; $^1$H NMR (300 MHz, DMSO-d$_6$): δ1.16–1.31 (band, 4H), 1.44 (m, 2H), 1.69 (m, 2H), 1.85 (s, 3H), 2.42 (t, J=7 Hz, 2H), 3.71 (t, j=7.3 Hz 1H), 4.89 (d, 2.19 Hz, 21), 7.18 (d, J=8.9 Hz, 2H), 7.72 (d, J=8.9 Hz, 2H), 9.24 (s, 1H), 10.88 (s, 1H).

EXAMPLE 73

2-{[4-(2-butynyloxy)phenyl]sulfanyl}-2-cyclohexyl-N-hydroxyacetamide

Step 1
2-bromo cyclohexyl acetic acid

To a solution of cyclohexylacetic acid (10 g, 70 mmol), in 100 ml of CCl4 was added red phosphorus (6.32 g, 204 mmol). The mixture was heated to reflux and bromine (70.7 ml, 1.38 mmol) was added over 3 hours dropwise through the condenser via addition funnel. The reaction was heated at reflux for 5 hours before it was quenched slowly with water then washed with 10% Na$_2$SO$_4$, water, then into NaHCO$_3$. The sodium bicarbonate solution was brought to acidic pH using 1 N HCl. The solid was collected and the aqueous filtrate was extracted into CHCl$_3$, washed with saturated Na$_2$HSO$_4$ solution then with water. The organic layer was dried over Na$_2$SO$_4$, filtered and concentrated and combined with solid collected earlier to provide 3.22 g 2-bromo cyclohexyl acetic acid as a white solid. Yield 21%; MS: 219.1 (M–H)⁻

Step 2
Ethyl cyclohexyl [4-(hydroxyphenyl)sulfanyl]-acetic acid was prepared according to the general method as outlined in example 1 (step 1), starting from 2-bromo cyclohexyl acetic acid (3.08 g, 13.9 mmol) and 4-mercaptophenol (2 g, 14.2 mmol); 3.10 g yellow oil. The product was pure enough and taken for further transformations. Yield 84%; MS: 265 (M+H⁺.

Step 3
Ethyl cyclohexyl [4-(hydroxyphenyl)sulfanyl]acetate

To a solution of ethyl cyclohexyl [4-(hydroxyphenyl)sulfanyl]-acetic acid (3.1 g, 11.65 mmol) in 100 ml ethanol, 1 ml of sulfuric acid was added. The mixture was heated at reflux overnight then concentrated, extracted in methylene chloride, washed first with saturated NaHCO$_3$ solution then with water. The organic layer was dried over Na$_2$SO$_4$, filtered over magnesol and concentrated to provide 1.22 g ethyl cyclohexyl [4-(hydroxyphenyl)sulfanyl]acetate as a yellow oil. Yield 35%; MS: 295.4 (M+H)⁺

Step 4
Ethyl-{[4-(2-butynyloxy)phenyl]sulfanyl}(cyclohexyl) acetate was prepared according to the general method as outlined in example 1 (step 2), starting from ethyl cyclohexyl [4-(hydroxyphenyl)sulfanyl]acetate (1 g, 3.4 mmol) and 4-bromo-2-butyne (0.32 ml, 3.7 mmol); 1.25 g yellow oil. Yield 100%; MS(EI): 346.1 (M+H)⁺

Step 5
{[4-(2-butynyloxy)phenyl]sulfanyl}(cyclohexyl) acetic acid was prepared according to the general method as outlined in example 1 (step 5), starting from ethyl-{[4-(2-butynyloxy)phenyl]sulfanyl}(cyclohexyl) acetate (1.2 g, 3.47 mmol); 1.19 g yellow oil. Yield 100%; MS: 317.4 (M–H)⁻

Step 6
Starting from {[4-(2-butynyloxy)phenyl]sulfanyl}(cyclohexyl)acetic acid and following the procedure as outlined in Example 1 (step 6), 672 mg of 2-{[4-(2-butynyloxy)phenyl]sulfanyl}-2-cyclohexyl-N-hydroxyacetamide was isolated as a white powder. mp: 163° C.; Yield: 75%; MS: 334.1 (M+H)⁺; $^1$H NMR (300 MHz, DMSO-d$_6$): δ0.86–1.12 (band, 5H), 1.62 (m, 51), 1.83 (t, J=2.25 Hz, 3H), 2.05 (d, J=11.9 Hz, 1H), 3.12 (d, J=9.1 Hz, 1H), 4.73 (d, J=2.34 Hz, 2H), 6.92 (d, J=8.7 Hz, 2H), 7.36 (d, J=8.7 Hz, 2H), 8.92 (s, 1H), 10.5 (s, 1H).

EXAMPLE 74

2-{[1(2-butynyloxy)phenyl]sulfinyl}-2-cyclohexyl-N-hydroxyacetamide

Starting from 2-{[4-(2-butynyloxy)phenyl]sulfanyl}-2-cyclohexyl-N-hydroxyacetamide (580 mg, 1.74 mmol), and following the procedure as outlined in Example 7, 230 mg of 2-{[4-(2-butynyloxy)phenyl]sulfinyl}-2-cyclohexyl-N-hydroxyacetamide was isolated as a white solid. mp: 188° C.; Yield: 38%; MS: 350.2 (M+H)⁺; $^1$H NMR (300 MHz, DMSO-d$_6$): δ1.05 (m, 3H), 1.24 (m, 2H), 1.41–1.72 (band, 5H), 1.84 (t, J=2.22 Hz, 3H), 2.5 (m, 1H), 3.14 (d, J=7.23 Hz, 1H), 4.89 (m, 2H), 7.16 (d, J=9 Hz, 2H), 7.61 (d, J=8.7 Hz, 2H), 9.0 (d, 1H), 10.4 (d, 1H).

EXAMPLE 75

2-{[4-(2-butynyloxy)phenyl]sulfonyl}-2-cyclohexyl-N-hydroxyacetamide

To a stirred solution of 2-{[4-(2-butynyl oxy)phenyl]sulfinyl}-2-cyclohexyl-N-hydroxyacetamide (180 mg, 0.52 mmol) in MeOH/THF at room, oxone (5.0 g, excess) was added in water (20 ml). Reaction mixture was stirred at room temperature for 6 hrs and filtered. Methanol-THF layer was concentrated and extracted with chloroform. The organic layer was washed well with water, dried, filtered and concentrated. The product was purified by silica gel column chromatography by eluting it with 4:1 ethyl acetate; hexane and 2-{[4-(2-butynyloxy) phenyl]sulfonyl}-2-cyclohexyl-N-hydroxyacetamide was isolated as a white solid. mp: 191° C.; Yield: 45 mg (24%); MS: 366.3 (M+H)⁺; $^1$H NMR (300 MHz, DMSO-d$_6$): δ0.95–1.12 (band, 5H), 1.58 (m, 5H), 1.85 (t, J=2.22 Hz, 3H), 2.05 (m, 1H), 3.63 (d, J=9.1 Hz, 1H), 4.87 (d, J=2.34 Hz, 2H), 7.16 (d, J=9 Hz, 2H), 7.76 (d, J=9 Hz, 2H), 9.01 (s, 11H), 10.7 (s, 1H).

EXAMPLE 76

2-{14-(2-butynyloxy)phenyl]sulfanyl}-N-hydroxy-2-(4-methoxyphenyl)acetamide

Step 1
Ethyl [(4-hydroxyphenyl)sulfanyl](4-methoxyphenyl) acetate

Ethyl bromo (4-methoxyphenyl) acetate (16.5 g, 60.4 mmol) was added to a stirring solution of triethylamine (10 ml), and 4-mercaptophenol (7.63 g, 60.4 mmol) in Chloroform (200 ml). The mixture was heated at reflux overnight before it was concentrated and the residue was extracted in ethyl acetate and washed with water. The organic layer was dried over Na$_2$SO$_4$, filtered and concentrated. The compound was isolated using silica-gel column chromatography by eluting it with 20% ethyl acetate: hexane solution. Ethyl [(4-hydroxyphenyl)sulfanyl](4-methoxyphenyl) acetate was isolated as a yellow oil (15.82 g). Yield 82%; MS: 317.2 (M–H)⁻

Ethyl {[4-(2-butynyloxy)phenyl]sulfanyl}(4-methoxyphenyl)acetate was prepared according to the general method as outlined in example 1 (step 1), starting from ethyl [(4-hydroxyphenyl)sulfanyl](4-methoxyphenyl) acetate (15.82 g, 49.7 mmol) and 4-bromo-2-butyne (4.79 ml, 54.7 mmol); 17.66 g yellow oil. Yield 96%; MS(EI): 370.1 (M+H)⁺ {[4-(2-butynyloxy)phenyl]sulfanyl}(4-methoxyphenyl) acetic acid was prepared according to the general method as outlined in example 1 (step 5), (the hydrolysis was carried out at room temperature for 24 hrs) starting from ethyl {[4-(2-butynyloxy)phenyl]sulfanyl}(4-methoxyphenyl)acetate (10 g, 27 mmol); 5.78 g yellow oil. Yield 63%; MS: 341.2 (M–H)⁻

Starting from {[4-(2-butynyloxy)phenyl]sulfanyl}(4-methoxyphenyl) acetic acid (5.59 g, 16.3 mmol), and following the procedure as outlined in Example 1 (step 6), 450 mg of 2-{[4-(2-butynyloxy)phenyl]sulfanyl}-N-hydroxy-2-(4-methoxyphenyl) acetamide was isolated as a white solid. mp: 156° C.; Yield: 8%; MS: 358.3 (M+H)⁺; ¹H NMR (300 MHz, DMSO-d₆): δ1.82 (t, J=2.25 Hz, 3H), 3.72 (s, 3H), 4.65 (s, 1H), 4.71 (q, J=2.3 Hz, 2H), 6.89 (m, 4H), 7.26 (d, 21), 7.53 (d, 2H), 9.0 (s, 1H), 10.8 (s, 1H).

EXAMPLE 77

(2R)-2-{[4-(2-butynyloxy)phenyl]sulfinyl}-N-hydroxy-2-(4-methoxyphenyl) ethanamide &

EXAMPLE 78

(2S)-2-{[4-(2-butynyloxy)phenyl]sulfinyl}-N-hydroxy-2-(4-methoxyphenyl) ethanamide Starting from 2-{[4-(2-butynyloxy)phenyl]sulfanyl}-N-hydroxy-2-(4-methoxyphenyl) acetamide (prepared in Example 76) (340 mg, 0.95 mmol), and following the procedure as outlined in Example 7. The two diastereo isomers were separated by silica-gel column chromatography by eluting it with 50% ethyl acetate; hexane. The faster moving isomer, namely (2R)-2-{[4-(2-butynyloxy)phenyl]sulfinyl}-N-hydroxy-2-(4-methoxyphenyl) ethanamide was isolated as a white powder. mp: 157° C.; Yield: 49.0 mg (14%); MS: 374.3 (M+H)⁺; ¹H NMR (300 MHz, DMSO-d₆): δ1.83 (t, J=2.25 Hz, 3H), 3.70 (s, 3H), 4.32 (s, 1H), 4.76 (d, J=2.37 Hz, 2H), 6.8 (d, 2H), 6.99 (m, 4H), 7.13 (d, 2H), 9.2 (s, 1H), 11 (s, 1H).

The slower moving isomer namely(2S)-2-{[4-(2-butynyloxy)phenyl]sulfinyl}-N-hydroxy-2-(4-methoxyphenyl) ethanamide was isolated as a white powder. mp: 134 ° C.; Yield: 39 mg (10%); MS: 374.2 (M+H)⁺; ¹H NMR (300 MHz, DMSO-d₆): δ1.85 (t, J=2.25 Hz, 3H), 3.77 (s, 3H), 4.29 (s, 1H), 4.81 (d, J=2.4 Hz, 2H), 6.93 (d, J=8.76 Hz, 2H), 7.12 (d, J=8.85 Hz, 2H), 7.32 (d, J=8.76 Hz, 2H), 7.48 (d, J=8.79 Hz, 2H), 8.95 (s, 1H), 10.6 (s, 1H).

EXAMPLE 79

2-{14-(2-butynyloxy)phenyl]sulfonyl}-N-hydroxy-2-(4-methoxyphenyl) acetamide

Starting from 2-{[4-(2-butynyloxy)phenyl]sulfanyl}-N-hydroxy-2-(4-methoxyphenyl) acetamide (290 mg, 0.8 mmol), and following the procedure as outlined in Example 75, 120 mg of 2-{[4-(2-butynyloxy)phenyl]sulfonyl}-N-hydroxy-2-(4-methoxyphenyl) acetamide was isolated as a white powder. mp: 190° C.; Yield: 39%; MS: 390.2 (M+H)⁺; ¹H NMR (300 MHz, DMSO-d₆): δ1.85 (t, J=2.22 Hz, 3H), 3.74 (s, 3H), 4.85 (d, J=2.31 Hz, 2H), 4.94 (s, 1H), 6.86 (d, J=9 Hz, 2H), 7.08 (d, J=7.2 Hz, 2H), 7.26 (d, J=9 Hz, 2H), 7.45 (d, J=9 Hz, 2H), 9.24 (d, J=1.5 Hz), 1H), 10.9 (s, 1H).

EXAMPLE 80

2-{[4-(2-butynyloxy)phenyl]sulfanyl}-2-(4-chlorophenyl)-N-hydroxyacetamide

Ethyl (4-chlorophenyl)[(4-hydroxyphenyl)sulfanyl] acetate was prepared according to the general method as outlined in example 1 (step 1), starting from ethyl bromo (4-chlorophenyl) acetate (16.5 g, 59.6 mmol) and 4-mercaptophenol (7.5 g, 59.6 mmol); 18.8 g white solid. mp: 63° C.; Yield 97%; MS: 321.3 (M–H)⁻

Ethyl {[4-(2-butynyloxy)phenyl]sulfanyl}(4-chlorophenyl) acetate was prepared according to the general method as outlined in example 1 (step 2), starting from ethyl (4-chlorophenyl)[(4-hydroxyphenyl)sulfanyl]acetate (15.37 g, 47.7 mmol) and 4-bromo-2-butyne (4.26 ml, 48.7 mmol); 12.57 g yellow oil. Yield 69%; MS(EI): 374 (M+H)⁺

{[4-(2-butynyloxy)phenyl]sulfanyl}(4-chlorophenyl) acetic acid was prepared according to the general method as outlined in example 1 (step 5), starting from ethyl{[4-(2-butynyloxy)phenyl]sulfanyl}(4-chlorophenyl) acetate (3.91 g, 10.5 mmol); 2.63 g yellow oil. Yield 72%; MS: 345.2 (M–H)⁻

Starting from {[4-(2-butynyloxy)phenyl]sulfanyl}(4-chlorophenyl) acetic acid (2.43 g, 7.02 mmol), and following the procedure as outlined in Example 1 (step 6), 65 mg of 2-{[4-(2-butynyloxy)phenyl]sulfanyl}-2-(4-chlorophenyl)-N-hydroxyacetamide was isolated as a white powder. mp: 152° C.; Yield: 3%; MS: 362.2 (M+H)⁺; ¹H NMR (300 M[z, DMSO-d₆): δ1.82 (t, J=2.31 Hz, 3H), 4.72 (m, 3H), 6.89 (d, 2H), 7.26 (d, 2H), 7.4 (m, 4H), 9.1 (s, 1H), 10.9 (s, 1H).

EXAMPLE 81

2-{[1(2-butynyloxy)phenyl]sulfinyl}-2-(4-chlorophenyl) N-hydroxyacetamide

Starting from 2-{[4-(2-butynyloxy)phenyl]sulfanyl}-2-(4-chlorophenyl)-N-hydroxyacetamide (prepared from example 80) (1.35 g, 3.74 mmol), and following the procedure as outlined in Example 7, 70 mg of 2-{[4-(2-butynyloxy)phenyl]sulfinyl}-2-(4-chlorophenyl) N-hydroxyacetamide was isolated as a white powder. This compound was tested as the mixture of diastereo isomers. Mp: 92° C.; Yield: 5%; MS: 378 (M+H)⁺; ¹H NMR (300 MHz, DMSO-d₆): δ1.83 (t, J=2.25 Hz, 3H), 4.43 (s, 1H), 4.77 (d, J=2.37 Hz, 2H), 6.98 (d, 2H), 7.09 (d, 2H), 7.19 (d, 2H), 7.34 (d, 2H), 9.32 (s, 1H), 11 (s, 1H).

EXAMPLE 82

2-{14-(2-butynyloxy)phenyl]sulfonyl}-2-(4-chlorophenyl)-N-hydroxyacetamide

Starting from a mixture of 2-{[4-(2-butynyloxy)phenyl]sulfanyl}-2-(4-chlorophenyl)-N-hydroxyacetamide (from example 80) and 2-{[4-(2-butynyloxy)phenyl]sulfinyl}-2-(4-chlorophenyl) N-hydroxyacetamide (750 mg, 1.99 mmol), and following the procedure as outlined in Example 75, 228 mg of 2-{[4-(2-butynyloxy)phenyl]sulfonyl}-2-(4-chlorophenyl)-N-hydroxyacetamide was isolated as a white solid. mp: 140° C.; Yield: 29%; MS: 394.2 (M+H)⁺; ¹H NMR (300 MHz, DMSO-$d_6$): δ1.85 (t, J=2.19 Hz, 3H), 4.86 (d, J=2.28 Hz, 2H), 5.05 (s, 1H), 7.1 (d, 2H), 7.4 (m, 4H), 7.5 (d, 2H), 9.33 (s, 1H), 10.8 (s, 1H).

EXAMPLE 83

2-{[4-(2-butynyloxy)phenyl]sulfanyl}-2-(3-chlorophenyl)-N-hydroxyacetamide

Step 1

Ethyl (3-chlorophenyl)[(4-hydroxyphenyl)sulfanyl] acetate was prepared according to the general method as outlined in example 1 (step 1), starting from ethyl bromo (3-chlorophenyl) acetate (6.16 g, 16.5 mmol) and 4-mercaptophenol (2.08 g, 16.5 mmol); 4.36 g clear oil. Yield 82%; MS: 321 (M−H)⁻

Step 2

Ethyl {[4-(2-butynyloxy)phenyl]sulfanyl}(3-chlorophenyl)acetate The ethyl (3-chlorophenyl)[(4-hydroxyphenyl)sulfanyl]acetate (4.2 g, 13 mmol) was stirred with THF (100 ml) in a dried two-necked flask under inert conditions. The 2-butyn-1-ol (0.97 ml, 13 mmol) and 1,1'(azodicarbonyl) dipiperidine (3.94 g, 15.6 mmol). Tributylphosphine (3.90 ml, 15.6 mmol) was added dropwise at 0° C. The reaction mixture was allowed to stir at room temperature under nitrogen for 2 hours before it was concentrated. The residue was triturated with ether and the filtrate was concentrated, Ethyl {[4-(2-butynyloxy)phenyl] sulfanyl}(3-chlorophenyl)acetate was isolated as a yellow oil (4.08 g) after silica-gel column chromatography, using methylene chloride as the mobile phase. Yield 84%; MS(EI): 375 (M+H)⁺

{[4-(2-butynyloxy)phenyl]sulfanyl}(3-chlorophenyl) acetic acid was prepared according to the general method as outlined in example 1 (step 5), starting from ethyl{[4-(2-butynyloxy)phenyl]sulfanyl}(3-chlorophenyl)acetate (4.08 g, 10.9 mmol); 2.04 g off white powder. mp: 64° C. Yield 54%; MS: 691.4 (2M−H)⁻

Starting from {[4-(2-butynyloxy)phenyl]sulfanyl}(3-chlorophenyl) acetic acid (1.86 g, 5.37 mmol), and following the procedure as outlined in Example 1 (step 6), 130 mg of 2-{[4-(2-butynyloxy)phenyl]sulfanyl}-2-(3-chlorophenyl)-N-hydroxyacetamide was isolated as a white powder. mp: 127° C.; Yield: 7%; MS: 362.1 (M+H)⁺; ¹H NMR (300 MHz, DMSO-$d_6$): δ1.82 (t, J=2.31 Hz, 3H), 4.72 (m, 3H), 6.91 (d, 2H), 7.26 (d, 2H), 7.34 (m, 3H), 7.48 (s, 1H), 9.1 (s, 1H), 10.9 (s, 1H).

EXAMPLE 84

2-{[4-(2-butynyloxy)phenyl]sulfonyl}-2-(3-chlorophenyl)-N-hydroxyacetamide

Starting from a mixture of 2-{[4-(2-butynyloxy)phenyl] sulfanyl}-2-(3-chlorophenyl)-N-hydroxyacetamide and 2{[4-(2-butynyloxy)phenyl]sulfinyl}-2-(3-chlorophenyl) N-hydroxyacetamide (210 mg, 0.56 mmol), and following the procedure as outlined in Example 75, 60 mg of 2-{[4-(2-butynyloxy)phenyl]sulfonyl-2-(3-chlorophenyl)-N-hydroxyacetamide was isolated as a white powder. mp: 50° C.; Yield: 27%; MS: 394.1 (M+H)⁺; ¹H NMR (300 MHz, DMSO-$d_6$): δ1.84 (t, J=2.22 Hz, 3H), 4.86 (d, J=2.31 Hz, 2H), 5.06 (s, 1H), 7.12 (d, J=8.97 Hz, 2H), 7.19–7.39 (band, 2H), 7.48 (m, 4H), 9.33 (d, J=1.2 Hz, 1H), 10.9 (s, 1H).

EXAMPLE 85

2-(4-bromophenyl)-2-{[4(2-butynyloxy)phenyl] sulfanyl}-N-hydroxyacetamide

Ethyl (4-bromophenyl)[(4-hydroxyphenyl)sulfanyl] acetate was prepared according to the general method as outlined in example 1 (step 1), starting from ethyl bromo (4-bromophenyl) acetate (15 g, 45.6 mmol) and 4-mercaptophenol (5.75 g, 45.6 mmol); 15.39 g white solid. mp: 55.6° C.; Yield 92%; MS: 365.1 (M−H)⁻

Ethyl (4-bromophenyl) {[4-(2-butynyloxy)phenyl] sulfanyl}acetate was prepared according to the general method as outlined in example 83 (step 2), starting from ethyl (4-bromophenyl)[(4-hydroxyphenyl)sulfanyl]acetate (13.57 g, 36.9 mmol) and 2-butyn-1-ol (2.77 ml, 36.9 mmol); 9.05 g clear oil. Yield 59%; MS(EI): 420.8 (M+H)⁺

(4-bromophenyl){([4-(2-butynyloxy)phenyl] sulfanyl}acetic acid was prepared according to the general method as outlined in example 1 (step 5), starting from ethyl (4-bromophenyl){[4-(2-butynyloxy)phenyl] sulfanyl}acetate (1.2 g, 2.86 mmol); 860 mg brown oil. Yield 77%; MS: 389.2 (M−H)⁻

Starting from (4-bromophenyl){[4-(2-butynyloxy) phenyl]sulfanyl}acetic acid (790 mg, 2.02 mmol), and following the procedure as outlined in Example 1 (step 6), 61 mg of 2-(4-bromophenyl)-2-{[4-(2-butynyloxy)phenyl] sulfanyl}-N-hydroxyacetamide was isolated as a white solid. mp: 153° C.; Yield: 24%; MS: 408 (M+H)⁺; ¹H NMR (300 MHz, DMSO-$d_6$): δ1.82 (t, J=2.28 Hz, 3H), 4.68 (s, 1H), 4.71 (q, 2H), 6.89 (d, 2H), 7.25 (d, 2H), 7.36 (d, 2H), 7.51 (d, 2H), 9.07 (s, 1H), 10.8 (s, 1H).

EXAMPLE 86

(2S)-2-(4-bromophenyl)-2-{14-(2-butynyloxy) phenyl]sulfinyl)-N-hydroxyacetamide &

EXAMPLE 87

(2R)-2-(4bromophenyl)-2-{14-(2-butynyloxy) phenyl]sulfinyl}-N-hydroxyacetamide

Starting from 2-(4-bromophenyl)-2-{[4-(2-butynyloxy) phenyl]sulfanyl}-N-hydroxyacetamide (from example 85) (1.54 g, 3.7 mmol), and following the procedure as outlined in Example 7 the two diastereo isomers were isolated. The two diastereo isomers were separated by silica-gel column chromatography by eluting it with 50% ethyl acetate; hexane. The faster moving isomer, namely (2S)-2-(4-bromophenyl)-2-{[4-(2-butynyloxy) phenyl]sulfinyl}-2-N-hydroxyacetamide was isolated as a white solid. mp: 167° C.; Yield: 170 mg (11%); MS: 424 (M+H)⁺; ¹H NMR (300 MHz, DMSO-$d_6$): δ1.85 (t, J=2.22 Hz, 3H), 4.39 (s, 1H), 4.82 (d, J=2.34 Hz, 2H), 7.1 (d, 2H), 7.3 (d, 2H), 7.5 (d, 2H), 7.56 (d, 2H), 9.07 (s, 1H), 10.7 (s, 1H).

The slow moving isomer namely, (2R)-2-(4-bromophenyl)-2-{[4-(2-butynyloxy) phenyl]sulfinyl}-2-N-hydroxyacetamide was isolated as an off white solid. mp: 93° C.; Yield: 20 mg, (1.3%); MS: 423.9 (M+H)⁺; ¹H NMR (300 MHz, DMSO-$d_6$): δ1.83 (t, J=2.13 Hz, 3H), 4.42 (s, 1H), 4.77 (d, J=2.28 Hz, 2H), 7.0 (m, 4H), 7.2 (d, 21), 7.5 (d, 2H), 9.33 (s, 1H), 10.9 (s, 1H).

EXAMPLE 88

2-(4-bromophenyl)-2-{14-(2-butynyloxy)phenyl] sulfonyl}-N-hydroxyacetamide

Starting from a mixture of 2-(4-bromophenyl)-2-{[4-(2-butynyloxy)phenyl]sulfanyl}-N-hydroxyacetamide and 2-(4-bromophenyl)-2-{[4-(2-butynyloxy)phenyl]sulfinyl}-2-N-hydroxyacetamide (1.42 g, 3.4 mmol), and following the procedure as outlined in Example 75, 610 mg of 2-(4-bromophenyl)-2-{[4-(2-butynyloxy) phenyl]sulfonyl}-N- hydroxyacetamide was isolated as a white solid. mp: 187° C.; Yield: 41%; MS: 440 (M+H)+; $^1$H NMR (300 MHz, DMSO-d$_6$): δ1.85 (t, J=2.22 Hz, 3H), 4.86 (d, J=2.31 Hz, 2H), 5.03 (s, 1H), 7.11 (d, 2H), 7.31 (d, 2H), 7.47 (d, 2H), 7.55 (d, 2H), 9.32 (s, 1H), 10.9 (s, 1H).

EXAMPLE 89

2{[4-(2-butynyloxy)phenyl]sulfanyl}-N-hydroxy-2-[4-(2-thienyl)phenyl]acetamide

Step 1

Ethyl [4-(2-thienyl)phenyl]acetate

Nitrogen was bubbled through a mixture of 2-tributylstannyl thiophene (15.68 ml, 49.4 mmol) and ethyl (4-bromophenyl)acetate (6 g, 24.7 mmol) in toluene (250 ml) before 0.5 g of tetrakis (triphenylphosphine) palladium (0) was added. The mixture was heated at reflux under nitrogen for 4 hours before it was filtered through magnesol and concentrated. The residue was purified using silica-gel column chromatography by eluting it with 20% ethyl acetate: hexane solution. Ethyl [4-(2-thienyl)phenyl]acetate was isolated as a yellow oil (4.15 g). Yield 68%; MS: 247.5 (M+H)+

Step 2

Ethyl bromo [4-(2-thienyl)phenyl]acetate

To a solution of ethyl [4-(2-thienyl)phenyl]acetate (4.1, 16.6 mmol) in carbon tetrachloride (150 ml) benzoyl peroxide (0.5 g) and N-bromosuccimide (3.26 g, 18.3 mmol) was added. The mixture was heated at reflux under nitrogen for 3 hours before it was filtered and concentrated. The residue was extracted in chloroform and washed with water. The organic layer was dried over Na$_2$SO$_4$, filtered and concentrated. The residue was purified using silica-gel column chromatography by eluting it with 15% ethyl acetate: hexane solution. Ethyl bromo [4-(2-thienyl)phenyl]acetate was isolated as a low melting white solid (2.19 g). Yield 40%; MS(EI): 325.2 (M+H)+

Ethyl [(4-hydroxyphenyl)sulfanyl][4-(2-thienyl)phenyl] acetate was prepared according to the general method as outlined in example 1 (step 1), starting from ethyl bromo [4-(2-thienyl)phenyl]acetate (2 g, 6.15 mmol) and 4-mercaptophenol (0.82 g, 6.5 mmol); 1.68 g white solid. mp: 103° C.; Yield 73%; MS: 369.1 (M−H)−

Ethyl {[4-(2-butynyloxy)phenyl]sulfanyl}[4-(2-thienyl) phenyl]acetate was prepared according to the general method as outlined in example 83 (step 2), starting from ethyl [(4-hydroxyphenyl)sulfanyl][4-(2-thienyl)phenyl] acetate (1.6 g, 4.3 mmol) and 2-butyn-1-ol (0.33 ml, 4.32 mmol); 1.34 g yellow oil. Yield 74%; MS(EI): 421.71 (M+H)+

{[4-(2-butynyloxy)phenyl]sulfanyl}[4-(2-thienyl)phenyl] acetic acid was prepared according to the general method as outlined in example 1 (step 5), starting from ethyl {[4-(2-butynyloxy)phenyl]sulfanyl}[4-(2-thienyl)phenyl] acetate (1.34 g, 3.17 mmol); 1.07 g white solid. mp: 137° C. Yield 85%; MS: 439.1 (M+FA−H)−

Starting from {[4-(2-butynyloxy)phenyl]sulfanyl}[4-(2-thienyl)phenyl]acetic acid (840 mg, 2.13 mmol), and following the procedure as outlined in Example 1 (step 6), 1.052 g of 2{[4-(2-butynyloxy)phenyl]sulfanyl}-N-hydroxy-2-[4-(2-thienyl)phenyl]acetamide was isolated as a white solid. mp: 182° C.; Yield: 99%; MS: 410 (M+H)+; $^1$H NMR (300 MHz, DMSO-d$_6$): δ1.81 (t, J=2.31 Hz, 31), 4.71 (m, 3H), 6.9 (d, 2H), 7.13 (m, 1H), 7.28 (d, 2H), 7.44–7.62 (band, 6H), 9.07 (s, 1H), 10.8 (s, 1H).

EXAMPLE 90

(2R)-2-{11(2-butynyloxy)phenyl]sulfinyl}-N-hydroxy-2-14-(2-thienyl)phenyl]ethanamide Starting from 2{[4-(2-butynyloxy)phenyl]sulfanyl}-N-hydroxy-2-[4-(2-thienyl)phenyl]acetamide (1 g, 2.13 mmol), and following the procedure as outlined in Example 7, 160 mg of (2R)-2-{[4-(2-butynyloxy) phenyl]sulfinyl}-N-hydroxy-2-[4-(2-thienyl)phenyl]ethanamide was isolated as an off white solid. mp: 158° C.; Yield: 18%; MS: 425.9 (M+H)+; $^1$H NMR (300 MHz, DMSO-d$_6$): δ1.79 (t, J=2.1 Hz, 3H), 4.43 (s, 1H), 4.75 (d, J=2.31 Hz, 2H), 6.98 (d, J=8.85 Hz, 2H), 7.12 (m, 3H), 7.22 J=8.79 Hz, 2H), 7.54 (m, 4H), 9.31 (d, 1H), 11 (s, 1H).

EXAMPLE 91

2-{[4-(2-butynyloxy)phenyl]sulfonyl}-N-hydroxy-2-[4-(2-thienyl)phenyl]acetamide

Starting from a mixture of 2{[4-(2-butynyloxy)phenyl] sulfanyl}-N-hydroxy-2-[4-(2-thienyl)phenyl]acetamide and 2-{[4-(2-butynyloxy) phenyl]sulfinyl}-N-hydroxy-2-[4-(2-thienyl)phenyl]ethanamide (410 mg, 0.96 mmol), and following the procedure as outlined in Example 75, 110 mg of 2-{([4-(2-butynyloxy) phenyl]sulfonyl}-N-hydroxy-2-[4-(2-thienyl)phenyl]acetamide was isolated as a gray solid. mp: 175° C.; Yield: 26%; MS: 442.2 (M+H)+; $^1$H NMR (300 MHz, DMSO-d$_6$): δ1.83 (t, 3H), 4.85 (d, J=2.01 Hz, 2H), 5.04 (s, 1H), 7.11 (m, 4H), 7.39 (d, 2H), 7.49–7.63 (band, 5H), 9.30 (s, 1H), 10.9 (s, 1H).

EXAMPLE 92

2-{1[(2-Butynyloxy)phenyl]sulfanyl}-N-hydroxy-2-(1-napthyl)acetamide

Ethyl[(4-hydroxyphenyl)sulfanyl](1-napthyl)acetate was prepared according to the general method as outlined in Example 1 (Step 1). Starting from ethyl bromo(1-napthyl) acetate (11.0 g, 38 mmol) and 4-mercaptophenol (4.8 g, 38 mmol), 8.14 g of ethyl[(4-hydroxyphenyl)sulfanyl](1-napthyl)acetate was isolated. Yield (64%); amber oil; MS 337.1 (M−H)−

{[4-(2-Butynloxy)phenyl]sulfanyl}(1-napthyl)acetate was prepared according to the general method as outlined in Example 1 (Step 2). Starting from ethyl(4-hydroxyphenyl) sulfanyl](1-napthyl)acetate (7.74 g, 23 mmol) and 1-bromo-2-butyne (3.4 g, 25 mmol) 7.64 g of product was isolated. Yield (85%); amber oil; MS 390.5 (M+H)+

{([4-(2-Butynloxy)phenyl]sulfanyl}(1-napthyl)acetic acid was prepared according to the general method as outlined in Example 1 (Step 5). Starting from {[4-(2-Butynloxy)phenyl]sulfanyl}(1-napthyl)acetate (7.64 g, 19.6 mmol) 4.92 g of product was isolated. Yield (69%); white solid, mp 98.7° C.; MS 722.8 (2M−H)−

Starting from {[4-(2-Butynloxy)phenyl]sulfanyl}(1-napthyl)acetic acid (4.69 g, 12.95 mmol) and following the procedure as outlined in Example 1 (Step 6), 2.95 g of 2-{[4-(2-Butynyloxy)phenyl]sulfanyl}-N-hydroxy-2-(1-napthyl)acetamide was isolated as a white solid, mp 139.6° C.; MS 378.1 (M+H)+; $^1$H NMR (300 MHz, DMSO-d$_6$): δ1.87 (t, 3H), 4.62 (m, 2H), (s, 1H), 6.87 (d, J=10 Hz, 2H), 7.37 (d, J=8 Hz, 2H), 7.46 (bm, 4H), 7.80 (d, J=3 Hz, 1H), (d, J=4 Hz), 8.03 (d, J=8 Hz, 2H), 9.2 (s, 1H),

EXAMPLE 93

2-{[4-(2-Butynyloxy)phenyl]sulfinyl}-N-hydroxy-2-(1-napthyl)acetamide

Starting from 2-{[4-(2-butynyloxy)phenyl]sulfanyl}-N-hydroxy-2-(1-napthyl)acetamide (1.95 g, 5.2 mmol) and following the procedure as outlined in Example 7, 0.19 g of 2-{[4-(2-butynyloxy)phenyl]sulfinyl}-N-hydroxy-2-(1- napthyl)acetamide) was isolated as a white solid, mp 159.4° C.; MS 394.1 (M+H)+; 1H NMR (300 MHz, DMSO-d6): δ1.55 (t, 31), 4.60 (m, 2H), 5.51 (s, 1H), 6.72 (d, J=11.7 Hz, 2H), 7.24 (2H), 7.37 (m, 3H), 7.77 (m, 3H), 8.19 (s, 1H), 10.68

EXAMPLE 94

2-{[4-(2-Butynyloxy)phenyl]sulfonyl}-N-hydroxy-2-(l-napthyl)acetamide

Starting from 2-{[4-(2-butynyloxy)phenyl]sulfanyl}-N-hydroxy-2-(1-napthyl)acetamide (0.6 g, 15.9 mmol) and following the procedure as outlined in Example 75, 0.162 g of 2-{[4-(2-butynyloxy)phenyl]sulfonyl}-N-hydroxy-2-(1-napthyl)acetamide) was isolated as a white solid, mp 213.3° C.; MS 410.0 (M+H)+; 1H NMR (300 MHz, DMSO-d6): δ1.84 (t, 3H), 4.81 (d, J=2.3 Hz, 1H), 6.00 (s, 1H), 7.0 (d, J=9 Hz, 2H), 7.45 (d, J=11 Hz, 2H), 7.51 (m, 2H), 7.95 (m, 2H), 8.01 (d, J=17 Hz, 2H), 9.28 (s, 1H), 11.0 (s, 1H)

EXAMPLE 95

2-{4-[(2-Butynyloxy)phenyl]sulfanyl}-2-(4-fluorophenyl)-N-hydroxy-2-(1-napthyl)acetamide Ethyl[(4-fluorophenyl)[(4-hydroxyphenyl)sulfanyl] acetate was prepared according to the general method as outlined in Example 1 (Step 1). Starting from ethyl bromo (4-fluorophenyl)acetate (7.2 g, 28 mmol) and 4-mercaptophenol (3.8 g,30 mmol), 7.08 g of product was isolated. Yield (82.6%); amber oil; MS 305.3 (M-H)-

Ethyl{[4-(2-butynyloxy)phenyl]sulfanyl}(4-fluorophenyl)acetate was prepared according to the general method as outlined in Example 1 (Step 2). Starting from ethyl[(4-fluorophenyl)[(4-hydroxyphenyl)sulfanyl]acetate (7.05 g, 23 mmol) and 1-bromo-2-butyne (4.02 g, 30 mmol), 6.82 g of product was isolated. Yield (83%); amber oil; MS 358.0 (M-H)-

Ethyl{[4-(2-butynyloxy)phenyl]sulfanyl}(4-fluorophenyl) acetic acid was prepared according to the general method as outlined in Example 1 (Step 5). Starting from ethyl[(4-fluorophenyl)[(4-hydroxyphenyl)sulfanyl] acetate (4.73 g, 13 mmol)3.26 g of product was isolated. Yield (75%); amber gum; MS 329.3 (M-H)-

Starting from ethyl{[4-(2-butynyloxy)phenyl]sulfanyl}(4-fluorophenyl)acetic acid (3.0 g, 9.1 mmol) and following the procedure as outlined in Example 1 (Step 6), 0.295 g of 2-{[4-(2-butynyloxy)phenyl]sulfanyl}-2-(4-fluorophenyl)-N-hydroxyacetamide was isolated from the reaction mixture as a white solid, mp 105.7° C.; MS 346.1 (M+H)+; 1H NMR (300 MHz, DMSO-d6): δ1.82 (t, 3H), 4.70–4.72 (m, 3H), 6.00 (s, 1H), 6.19–6.91 (d, J=6.9 Hz, 2H), 7.15–7.21 (d, J=17 Hz, 2H), 7.24–7.27 (d, J=8.7 Hz, 2H), 7.4 (m, 2H), 9.08 (s, 1H), 10.78 (s, 1H)

Starting from of 2-{[4-(2-butynyloxy)phenyl]sulfanyl}-2-(4-fluorophenyl)-N-hydroxyacetamide (1.29 g, 3.3 mmol) and following the procedure as outlined in Example 7 0.086 g was isolated as a white solid, mp 91.1° C.; The major diastereo isomer was isolated. MS 362.3 (M+H)+; 1H NMR (300 MHz, DMSO-d6): δ1.83 (t, 3H), 4.41 (s, 1H), 4.76–4.77 (d, J=3 Hz, 2H), 6.97–7.01 (d, J=9.9 Hz, 2H), 7.07–7.10 (dd, J=8.9 Hz, 4H), 7.16–7.19 (d, J=8.8 HZ, 2H) 9.3 (s, 1H) 10.98 (s, 1H),

EXAMPLE 97

Preparation of 2-{14-(2-butynyloxy)phenyl] sulfonyl}-2-(4-fluorophenyl)-N-hydroxyacetamide Starting from of 2-{[4-(2-butynyloxy)phenyl]sulfanyl}-2-(4-fluorophenyl)-N-hydroxyacetamide (1.29 g, 3.3 mmol) and following the procedure as outlined in Example 75, 0.106 g was isolated as a white solid, mp 160. 1° C.; MS 378.2 (M+H)+; 1H NMR (300 MHz, DMSO-d6): δ1.84 (t, 3H), 4.85–4.86 (d, J=2.4 Hz, 2H), 5.04, (s, 1H), 7.08–7.11 (d, J=9.0 Hz, 2H), 7.16–7.19 (t, J=9.0 Hz, 2H) 7.38–7.40 (d,J=5.4 Hz, 2H) 7.45–7.47 (d, J=6.9 Hz, 2H), 9.3 (s, 1H), 10.90 (s, 1H).

EXAMPLE 98

2-(2-methoxyphenyl)-2-{14[(2-butynyloxy)phenyl] sulfanyl}-N-hydroxyacetamide

Ethyl (2-methoxyphenyl)[(4-hydroxyphenyl)sulfanyl] acetate was prepared according to the general method as outlined in example 1 (step 1), starting from ethyl bromo (2-methoxyphenyl) acetate (24 g, 87.5 mmol) and 4-mercaptophenol (11.0 g, 87.5 mmol); 24.9 g amber colored oil. Yield 89%; MS: 320 (M+H)+

Ethyl (2-methoxyphenyl) {[4-(2-butynyloxy)phenyl] sulfanyl}acetate was prepared according to the general method as outlined in example 1 (step 2), starting from ethyl (2-methoxyphenyl)[(4-hydroxyphenyl)sulfanyl]acetate (3.2 g, 10 mmol) and 1-bromo-2-butyne (1.5 g, 11.2 mmol); 3.2 g clear oil. Yield 87%; MS(EI): 371 (M+H)+

(2-methoxyphenyl) {[4-(2-butynyloxy)phenyl]sulfanyl) acetic acid was prepared according to the general method as outlined in example 1 (step 5), starting from ethyl (2-methoxyphenyl){[4-(2-butynyloxy)phenyl] sulfanyl}acetate (3.1 g, 8.3 mmol); 2.7 g of white solid was isolated. Yield 93%; MS: 341.4 (M-H)-

Starting from (2-methoxyphenyl){[4-(2-butynyloxy) phenyl]sulfanyl}acetic acid (2.6 g, 7.6 mmol), and following the procedure as outlined in Example 1 (step 6), 2.6 g of 2-(2-methoxyphenyl)-2-{[4-(2-butynyloxy)phenyl] sulfanyl}-N-hydroxyacetamide was isolated as a white solid. mp: 172–173° C.; Yield: 97%; MS: 358.4 (M+H)+; 1H NMR (300 MHz, DMSO-d6): δ1.85 (s,3H), 3.80 (s,3H), 4.72 (s, 2H), 5.12 (s, 1H), 6.62 (m, 4H), 7.3–7.5 (m, 4H), 9.3 (bs, 1H).

EXAMPLE 99

2-(2-methoxyphenyl)2-{11(2-butynyloxy)phenyl] sulfinyl}-N-hydroxyacetamide

Starting from of 2-{[4-(2-butynyloxy)phenyl]sulfanyl}-2-(2-methoxyphenyl)-N-hydroxyacetamide (3.0 g, 8.37 mmol) and following the procedure as outlined in Example 7 2.75 g of 2-(2-methoxyphenyl)-2-{[4-(2-butynyloxy) phenyl]sulfinyl}-N-hydroxyacetamide was isolated as a white solid, mp 167.8° C.; (Only the major diastereo isomer was isolated. MS 374 (M+H)+; 1H NMR (300 MHz, DMSO-d6): δ1.83 (s, 3H), 3.32 (s, 3H), 4.41 (s, 2H), 5.2 (s, 1H), 6.31 (d, 1H), 6.44 (m, 3H), 7.22–7.40 (m, 3H), 7.81 (d, 1), 8.62 (s, 1M 10.41 (s, 1H).

EXAMPLE 100

2-{[4-(2-butynyloxy)phenyl]sulfanyl}-N-hydroxy-2-(4-ethoxyphenyl) acetamide

Methyl [(4-hydroxyphenyl)sulfanyl](4-ethoxyphenyl) acetate Methyl bromo (4-ethoxyphenyl) acetate (7.6 g, 27.8 mmol) was added to a stirring solution of triethyl amine (30 ml), sodium sulfite(3.0 g, 23.8 mmol), and 4-mercaptophenol (3.5 g, 27.8 mmol) in methanol (200 ml). The mixture was stirred overnight before it was concentrated and the residue was extracted in ethyl acetate and washed with water. The organic layer was dried over $Na_2SO_4$, filtered and concentrated. The compound was isolated using silica-gel column chromatography by eluting it with 20% ethyl acetate:hexane solution. Methyl [(4-hydroxyphenyl)sulfanyl](4-ethoxyphenyl) acetate was isolated as a crude product (7.76 g, 24.4 mmol). Yield 88%. MS: 317.1 (M–H)⁻

Methyl {[4-(2-butynyloxy)phenyl]sulfanyl}(4-ethoxyphenyl) acetate was prepared according to the general method as outlined in example 1 (step 2). Starting from ethyl [(4-hydroxyphenyl)sulfanyl](4-methoxyphenyl) acetate (7.76 g, 24.4 mmol) and 1-bromo-2-butyne (3.26 & 24.4 mmol), 8.65 g of methyl {[4-(2-butynyloxy) phenyl]sulfanyl}(4-ethoxyphenyl) acetate. Yellow oil. Yield 95%; MS(EI): 369.72 (M)⁺

{[4-(2-butynyloxy)phenyl]sulfanyl}(4-ethoxyphenyl) acetic acid was prepared according to the general method as outlined in example 1 (step 5), starting from ethyl {[4-(2-butynyloxy)phenyl]sulfanyl}(4-ethoxyphenyl) acetate (8.55 g, 23 mmol); 7.86 g. Yield 96%; MS: 355.1(M–H)⁻

Starting from {[4-(2-butynyloxy)phenyl]sulfanyl}(4-ethoxyphenyl) acetic acid (7.61 g, 20.6 mmol), and following the procedure as outlined in Example 1 (step 6), 2.904 g of 2-{[4-(2-butynyloxy)phenyl]sulfanyl}-N-hydroxy-2-(4-ethoxyphenyl)acetamide was isolated. Yield: 38%; MS: 372.2 (M+H)⁺ ¹H NMR (300 MHz, DMSO-d₆): δ1.25 (t, J=2.22 Hz, 3H), 1.80 (s, 3H), 4.00 (q, J=2.22 Hz, 3H), 4.60 (s, 1H), 4.65 (s, 2H), 6.80 (d, J=9 Hz, 2H), 6.90 (d, J=9 Hz, 2H), 7.20 (d, J=9 Hz, 2H), 7.35 (d, J=9 Hz, 2H), 9.00 (s, 1H), 10.8 (s, 1H).

EXAMPLE 101

2-{14-(2-Butynyloxy)phenyl]sulfinyl}-N-hydroxy-2-(4-ethoxyphenyl) acetamide

Starting from 2-{[4-(2-butynyloxy)phenyl]sulfanyl}-N-hydroxy-2-(4-ethoxyphenyl) acetamide (808 mg, 2.27 mmol) and following the procedure as outlined in Example 7, 640 mg of 2-{[4-(2-Butynyloxy)phenyl]sulfinyl}-N-hydroxy-2-(4-ethoxyphenyl) acetamide was isolated as a brown powder. Yield: 73%; MS: 388.2 (M+H)⁺. Mp: 192–193.

EXAMPLE 102

2-{[4-(2-butynyloxy)phenyl]sulfonyl}-2-(4-chlorophenyl)-N-hydroxyacetamide

2-{[4-(2-butynyloxy)phenyl]sulfonyl}-2-(4-chlorophenyl)-N-hydroxyacetamide was prepared by Starting from 2-{[4-(2-butynyloxy)phenyl]sulfanyl}-N-hydroxy-2-(4-ethoxyphenyl) acetamide (808 mg, 2.27 mmol), and following the procedure as outlined in Example 75, 1.1 g of 2-{[4-(2-butynyloxy)phenyl]sulfonyl)-2-(4-chlorophenyl)-N-hydroxyacetamide was isolated as a white solid. MS: 404.2 (M+H)⁺, Mp: 138–140

EXAMPLE 103

2-{[4-(2-Butynyloxy)phenyl]sulfanyl}-N-hydroxy-2-(3-bromophenyl)acetamide

Methyl [(4-hydroxyphenyl)sulfanyl](3-bromophenyl) acetate Methyl bromo (3-bromophenyl) acetate (7.2 g, 23.3 mmol) was added to a stirring solution of triethyl amine (30 ml), sodium sulfite(3.0 g, 23.8 mmol), and 4-mercaptophenol (2.94 g, 23.3 mmol) in methanol (200 ml). The mixture was stirred overnight before it was concentrated and the residue was extracted in ethyl acetate and washed with water. The organic layer was dried over $Na_2SO_4$, filtered and concentrated. The compound was isolated using silica-gel column chromatography by eluting it with 20% ethyl acetate: hexane solution. Methyl [(4-hydroxyphenyl)sulfanyl](3-bromophenyl) acetate was isolated as a crude product (8.64 g). MS: 353.0 (M–H)⁻

Starting from ethyl [(4-hydroxyphenyl)sulfanyl](4-methoxyphenyl) acetate (8.0 g crude, 22.7 mmol) and 1-bromo-2-butyne (3.04 g, 22.7 mmol) and following the procedure as outlined in example 1 (step 2), 4.91 g of methyl {[4-(2-butynyloxy)phenyl]sulfanyl}(3-bromophenyl) acetate was isolated as yellow oil. Yield 52%; MS: 405.6 (M+H)⁺

Starting from ethyl {[4-(2-butynyloxy)phenyl]sulfanyl}(3-bromophenyl) acetate (4.04 g, 10 mmol) and following the procedure as outlined in example 1 (step 5), 3.83 g of {[4-(2-butynyloxy)phenyl]sulfanyl}(3-bromophenyl) acetic acid was isolated as a semi-solid. Yield 98%; MS: 389.0 M–H)⁻

Starting from {[4-(2-butynyloxy)phenyl]sulfanyl}(3-bromophenyl) acetic acid (3.83 g, 9.8 mmol), and following the procedure as outlined in Example 1 (step 6),1.675 g of 2-{[4-(2-butynyloxy)phenyl]sulfanyl}-N-hydroxy-2-(3-bromophenyl) acetamide was isolated. Yield: 42%; MS: 408.0 (M+H)⁺ ¹H NMR (300 MHz, DMSO-d₆): δ1.60 (m, 3H), 2.26 (s, 3H), 4.45 (s, 1H), 4.47 (m, 2H), 6.66 (d, J=9 Hz, 2H), 7.03 (d, J=9 Hz, 2H), 7.06–7.38(m, 5H), 8.87 (s, 1H), 10.41 (s, 1H).

EXAMPLE 104

(2R)-2-{[4-(2-butynyloxy)phenyl]sulfinyl}-N-hydroxy-2-(3-bromophenyl)acetamide

EXAMPLE 105

(2S)-2-{[4-(2-butynyloxy)phenyl]sulfinyl}-N-hydroxy-2-(3-bromophenyl)acetamide

Starting from 2-{[4-(2-butynyloxy)phenyl]sulfanyl}-N-hydroxy-2-(3-bromophenyl) acetamide (470 mg, 1.2 mmol), and following the procedure as outlined in Example 7, the sulfide was oxidised to sulfoxide. The mixture of two diastereoisomers were separated by silica-gel column chromatography by eluting it with 50% ethyl acetate; hexane. The faster moving isomer, namely (2R)-2-{[4-(2-butynyloxy)phenyl]sulfinyl}-N-hydroxy-2-(3-bromophenyl) acetamide was isolated as a brown powder. Yield: 230 mg, (47%); MS: 423.9 (M+H)⁺

The slower moving isomer namely, (2S)-2-{[4-(2-butynyloxy) phenyl]sulfinyl}-N-hydroxy-2-(3-bromophenyl) acetamide was isolated as a brown powder. Yield: 100 mg (20%); MS: 423.9 (M+H)⁺

EXAMPLE 106

2-{[4-(2-Butynyloxy)phenyl]sulfonyl}-2-(3-bromophenyl)-N-hydroxyacetamide

Starting from 2-{[4-(2-butynyloxy)phenyl]sulfanyl)-N-hydroxy-2-(3-bromophenyl) acetamide (480 mg, 1.2 mmol), and following the procedure as outlined in Example 75, 270mg of 2-{[4-(2-butynyloxy)phenyl]sulfonyl}-2-(4-chlorophenyl)-N-hydroxyacetamide was isolated as a brown powder. Yield: 52% MS: 440.1 (M+H)⁺ ¹H NMR (300 MHz DMSO-d₆): δ1.60 (m, 3H), 2.26 (s, 3H), 4.45 (s, 1H), 4.47 (m, 2H), 6.66 (d, J=9 Hz, 2H), 7.03 (d, J=9 Hz, 2H), 7.06–7.38 (m, 5H), 8.87 (s, 1H), 10.41 (s, 1H).

EXAMPLE 107

2{[4-(2-Butynyloxy)phenyl]sulfanyl}-2-isopropyl-N-hydroxyacetamide

Step 1

Ethyl isopropyl [4-(hydroxyphenyl)sulfanyl]-acetate was prepared according to the general method as outlined in example 1 (step 1), starting from ethyl 2-bromoisovalerate (2.09 g, 10 mmol) and 4-mercaptophenol (1.26 g, 10.0 mmol); 2.5 g yellow oil. The product was pure enough and taken for further transformations. Yield 99%; MS: 255 (M+H)$^+$.

Step 2

Ethyl-{[4-(2-butynyloxy)phenyl]sulfanyl}(isopropyl) acetate was prepared according to the general method as outlined in example 1 (step 2), starting from ethyl isoprpyl [4-(hydroxyphenyl)sulfanyl]-acetate (2.54 g, 10 mmol) and 4-bromo-2-butyne (1.34, 10 mmol); 3.0 g yellow oil. Yield 99%; MS(EI): 307 (M+H)$^+$ Step 3

{[4-(2-butynyloxy)phenyl]sulfanyl}(isopropyl) acetic acid was prepared according to the general method as outlined in example 1 (step 5), starting from ethyl-{[4-(2-butynyloxy)phenyl]sulfanyl}(isopropyl) acetate (3.06 g, 10 mmol); 2.7 g yellow oil. Yield 99%; MS: 277 (M–H)$^-$ Starting from {[4-(2-butynyloxy)phenyl]sulfanyl}(isopropyl) acetic acid (1.39 g, 5 mmol) and following the procedure as outlined in Example 1 (step 6), 800 mg of 2-{[4-(2-butynyloxy)phenyl]sulfanyl}-2-isopropyl-N-hydroxyacetamide was isolated as a white powder. mp: 128° C.; Yield: 54%; MS: 294.1 (M+H)$^+$; $^1$H NMR (300 MHz, DMSO-d$_6$): δ0.9 (d, 3H), 1.02 (d, 3H), 1.89 (s, 3H), 1.98 (m, 1H), 3.0 (d, 1H), 3.2 (s, 1H), 4.8 (s, 2H), 6.8 (d, J=9 Hz, 2H), 7.4 (d, J=9 Hz, 2H), 9.0 (s, 1H), 1H).

EXAMPLE 108

R-2-{[4-(2-butynyloxy)phenyl]sulfinyl}-2-isopropyl-N-hydroxyacetamide

Example 109

S2-{[4-(2-butynyloxy)phenyl]sulfinyl}-2-isopropyl-N-hydroxyacetamide

Starting from 2-{[4-(2-butynyloxy)phenyl]sulfanyl}-2-isoprpyl-N-hydroxyacetamide (1.45 g, 5 mmol), and following the procedure as outlined in Example 7, 123 mg of R-2-{[4-(2-butynyloxy)phenyl]sulfinyl}-2-isopropyl-N-hydroxyacetamide was isolated as a white solid. The two diastereo isomers were separated by silica-gel column chromatography by eluting it with 50% ethyl acetate: hexane. mp: 68° C.; Yield: 15%; MS: 310 (M+H)$^+$.

The slow moving isomer namely S-2-{[4-(2-butynyloxy)phenyl]sulfinyl}-2-isopropyl-N-hydroxyacetamide was isolated as white solid. Mp: 148° C.; Yield: 135 mg (17%; MS: 310 (M+H)$^+$.

EXAMPLE 110

2-{[4-(2-butynyloxy)phenyl]sulfonyl}-2-isoprpyl-N-hydroxyacetamide

Starting from 2-{[4-(2-butynyloxy)phenyl]sulfanyl}-N-hydroxy-2-isopropyl acetamide (1.4 g, 5 mmol), and following the procedure as outlined in Example 75, 800mg of 2-{[4-(2-butynyloxy)phenyl]sulfonyl}-2-isopropyl-N-hydroxyacetamide was isolated as a white powder. Yield: 49% MS: 326.1 (M+H)$^+$; $^1$H NMR (300 MHz, DMSO-d$_6$): δ0.8 (d, 3H), 1.0 (d, 3H), 2.0 (s, 3H), 2.1 (m, 1H), 3.51 (d, 1H), 3.2 (s, 1H), 5.01 (s, 2H), 7.0 (d, J=9 Hz, 2H), 756 (d, J=9 Hz, 2H), 9.5 (s, 1H), 11.41 (s, 1).

EXAMPLE 111

2-{[4-(2-Butynyloxy)phenyl]sulfanyl}-2-phenyl-N-hydroxyacetamide

Step 1

Ethyl phenyl [4-(hydroxyphenyl)sulfanyl]-acetate was prepared according to the general method as outlined in example 1 (step 1), starting from ethyl 2-bromophenylacetate (2.42 g, 10 mmol) and 4-mercaptophenol (1.26 g, 10.0 mmol); 2.7 g yellow oil. The product was pure enough and taken for further transformations. Yield 93%; MS: 289 (M+H)$^+$.

Step 2

Ethyl-{[4-(2-butynyloxy)phenyl]sulfanyl}(phenyl) acetate was prepared according to the general method as outlined in example 1 (step 2), starting from ethyl phenyl [4-(hydroxyphenyl)sulfanyl]-acetate (2.88 g, 10 mmol) and 4-bromo-2-butyne (1.34, 10 mmol); 3.2 g yellow oil. Yield 94%; MS(EI): 341 (M+H)$^+$ Step 3

{[4-(2-butynyloxy)phenyl]sulfanyl}(phenyl) acetic acid was prepared according to the general method as outlined in example 1 (step 5), starting from ethyl-{[4-(2-butynyloxy)phenyl]sulfanyl}(phenyl) acetate (3.4 g, 10 mmol); 3.0 g yellow oil. Yield 88%; MS: 311 (M–H)$^-$ Starting from {[4-(2-butynyloxy)phenyl]sulfanyl}(phenyl) acetic acid (3.12 g, 10 mmol) and following the procedure as outlined in Example 1 (step 6), 3.0 g of 2-{[4-(2-butynyloxy)phenyl]sulfanyl}-2-phenyl-N-hydroxyacetamide was isolated as a white powder. mp: 151° C.; Yield: 91%; MS: 328 (M+H)$^+$; $^1$H NMR (300 MHz, DMSO-d$_6$): δ1.8 (s, 3H), 4.8 (s, 2H), 4.9 (s,1H), 6.8–7.6 (m, 9H), 9.2 (bs, 1H), 11 (bs, 1H),

EXAMPLE 112

R-2-{[4-(2-butynyloxy)phenyl]sulfinyl}-2-phenyl-N-hydroxyacetamide

Example 113

S-2-{[4-(2-butynyloxy)phenyl]sulfinyl}-2-phenyl-N-hydroxyacetamide

Starting from 2-{[4-(2-butynyloxy)phenyl]sulfanyl}-2-phenyl-N-hydroxyacetamide (1.5 g, 4.5 mmol), and following the procedure as outlined in Example 7, 400 mg of R-2-{[4-(2-butynyloxy)phenyl]sulfinyl}-2-phenyl-N-hydroxyacetamide was isolated as a white solid. The two diastereo isomers were separated by silica-gel column chromatography by eluting it with 50% ethyl acetate: hexane. mp: 153° C.; Yield: 51%; MS: 344 (M+H)$^+$; $^1$H NMR (300 MHz, DMSO-d$_6$): δ1.8 (s, 3H), 4.5 (s, 1H), 4.9 (s, 2H), 6.9–7.6 (m, 9H), 9.0 (bs, 1H), 10.8 (bs, 1H).

The slow moving isomer namely S-2-{([4-(2-butynyloxy)phenyl]sulfinyl}-2-phenyl-N-hydroxyacetamide was isolated as white solid. Mp: 55° C.; Yield: 300 mg (38%; MS: 344 (M+H)$^+$; $^1$H NMR (300 MHz, DMSO-d$_6$): δ1.7 (s,3H), 4.4 (s, 1H), 4.7 (s, 2H), 7.0–7.6 (m, 9H), 9.3 (s, 1H), 11.0 (s, 1H).

EXAMPLE 114

2-{[4-(2-Butynyloxy)phenyl]sulfanyl}-2-(2-naphthyl)-N-hydroxyacetamide

Step 1

Ethyl (2-naphthyl)-2-[4-(hydroxyphenyl)sulfanyl]-acetate was prepared according to the general method as outlined in example 1 (step 1), starting from α-bromo-2-naphthyl acetic acid ethyl ester 2.93 g, 10 mmol) and 4-mercaptophenol (1.26 g, 10.0 mmol); 3.3 g yellow oil. The product was pure enough and taken for further transformations. Yield 99%; MS: 339 (M+H)$^+$.

Step 2

Ethyl-{[4-(2-butynyloxy)phenyl]sulfanyl}-2-(2-naphthyl) acetate was prepared according to the general method as outlined in example 1 (step 2), starting from ethyl (2-naphthyl)-2-[4-(hydroxyphenyl)sulfanyl]-acetate (2.54 g, 10 mmol) and 4-bromo-2-butyne (1.34, 10 mmol); 3.7 g yellow oil. Yield 99%; MS(EI): 377 (M+H)$^+$ Step 3

{[4-(2-butynyloxy)phenyl]sulfanyl}-2-(2-naphthyl) acetic acid was prepared according to the general method as outlined in example 1 (step 5), starting from ethyl-{[4-(2-butynyloxy)phenyl]sulfanyl}-2-(2-naphthyl) acetate (3.76 g, 10 mmol); 3.5 g yellow oil. Yield 96%; MS: 361 (M−H)$^-$ Starting from {[4-(2-butynyloxy)phenyl]sulfanyl}-2-(2-naphthyl) acetic acid (3.6 g, 10 mmol) and following the procedure as outlined in Example 1 (step 6), 3.2 g of 2-{[4-(2-butynyloxy)phenyl]sulfanyl}-2-(2-naphthyl)N-hydroxyacetamide was isolated as a white powder. mp: 148° C.; Yield: 84%; MS: 378 (M+H)$^+$; $^1$H NMR (300 MHz, DMSO-d$_6$): 1.8 (s, 3H), 4.7 (s, 2H), 4.95 (s, 1H), 6.8–8.0 (s, 1H), 9.0 (bs, 1H), 11 (bs, 1H).

EXAMPLE 115

2-{[4-(2-butynyloxy)phenyl]sulfinyl}-2-(2-naphthyl)-N-hydroxyacetamide

Starting from 2-{[4-(2-butynyloxy)phenyl]sulfanyl}-2-(2-naphthyl)-N-hydroxyacetamide (1.88 g, 5 mmol), and following the procedure as outlined in Example 7, 900 mg of 2-{[4-(2-butynyloxy)phenyl]sulfinyl}-2-(2-naphthyl)-N-hydroxyacetamide was isolated as a white solid. The two diastereo isomers were not separated. Mp: 157° C.; Yield: 46%; MS: 394 (M+H)$^+$.

EXAMPLE 116

2-{[4-(2-butynyloxy)phenyl]sulfonyl}-2-(2-naphthyl)N-hydroxyacetamide

Starting from 2-{[4-(2-butynyloxy)phenyl]sulfanyl}-N-hydroxy-2-(2-naphthyl) acetamide (1.81 g, 5 mmol), and following the procedure as outlined in Example 75, 1.2 g of 2-{[4-(2-butynyloxy)phenyl]sulfonyl}-2-(2-naphthyl)-N-hydroxyacetamide was isolated as a white powder. Yield: 61% MS: 410 (M+H)$^+$; $^1$H NMR (300 MHz, DMSO-d$_6$): δ2.5 (s, 3H), 4.9 (s, 2H), 5.2 (s, 1H), 7.0–7.9 (m, 1H), 9.3 (bs, 1H), 11 (s, 1H).

EXAMPLE 117

Tert-butyl-4-[1-{[4-(2-butynyloxy)phenyl]sulfonyl}-2-(hydroxyamino)-2-oxoethyl]-1-piperidine carboxylate tert-butyl 4-(2-ethoxy-2-oxoethyl)-1-piperidine carboxylate was made according to the literature procedure from Ashwood, Michael S.; Gibson, Andrew W.; Houghton, Peter G.; Humphrey, Guy R.; Roberts, D. Craig; Wright, Stanley H. B.; J. Chem. Soc. Perkin Trans. 1;6;1995; 641–643 in two steps starting from N-tert-butoxycarbonyl-4-piperidone; 4.69 g clear oil. Yield 95% (over two steps); MS: 272.2 (M+H)$^+$ Step 1 tert-butyl4-(1-{[4-(2-butynyloxy) phenyl]sulfonyl}-2-ethoxy-2-oxoethyl)-1-piperidine carboxylate, sodium bis (trimethylsilyl) amide (7.05 g, 38 mmol) was added to a dried flask under nitrogen. THF (100 ml) was added slowly and the temperature was lowered to -15° C. Tert-butyl 4-(2-ethoxy-2-oxoethyl)-1-piperidine carboxylate (4.6 g, 16.97 mmol) and 4-but-2-ynyl oxy-benzenesulfonyl fluoride (4.08 g, 17.9 mmol) were combined in THF (50 ml) and added dropwise to the mixture, maintaining the temperature of the reaction below −15° C. The mixture stirred at −10° C. for 1.5 hours before it was quenched with water and extracted in ethyl acetate. The organic layer was washed with water then dried over Na$_2$SO$_4$, filtered and concentrated. Tert-butyl-4-(1-{[4-(2-butynyloxy)phenyl]sulfonyl}-2-ethoxy-2-oxoethyl)-1-piperidine carboxylate was isolated using silica-gel column chromatography by eluting with 20% ethyl acetate: hexane solution; 3.74 g clear gel. Yield 46%; MS: 480.2 (M+H)$^+$ Step 2

[1-(tert-butoxycarbonyl)-4-piperidinyl]{[4-(2-butynyloxy) phenyl]sulfonyl}-acetic acid was prepared according to the general method as outlined in example 1 (step 5), starting from tert-butyl-4-(1-{[4-(2-butynyloxy) phenyl]sulfonyl}-2-ethoxy-2-oxoethyl)-1-piperidine carboxylate (2.5 g, 5.2 mmol); 1.85 g yellow low melting solid. Yield 79%; MS: 450.3 (M−H)$^-$ Step 3

Starting from [1-(tert-butoxycarbonyl)4-piperidinyl]{[4-(2-butynyloxy) phenyl]sulfonyl}-acetic acid (1.75 g, 3.88 mmol), and following the procedure as outlined in Example 1 (step 6), 283 mg of tert-butyl-4-[1-{[4-(2-butynyloxy) phenyl]sulfonyl}-2-(hydroxyamino)-2-oxoethyl]-1-piperidine carboxylate was isolated as a white solid. mp: 80° C.; Yield: 16%; MS: 467.1 (M+H)$^+$; $^1$H NMR (300 MHz, DMSO-d$_6$): δ1.08–1.25 (band, 3H), 1.37 (s, 9H), 1.53 (m, 1 H), 1.85 (t, J=2.22 Hz, 3H), 1.99–2.12 (band, 2H), 2.70 (m, 1H), 3.67 (d, J=19.8 Hz, 1H), 3.83 (m, 2H), 4.88 (d, J=2.31 Hz, 2H), 7.17 (d, J=9 Hz, 2H), 7.76 (d, J=9 Hz, 2H), 9.1 (s, 1H), 10.65 (s, 1H).

EXAMPLE 118

2-{[4-(2-butynyloxy)phenyl]sulfonyl}-N-hydroxy-2-(4-piperidinyl)acetamide

Step 1

2-{[4-(2-butynyloxy) phenyl]sulfonyl}-N-hydroxy-2-(4-piperidinyl)acetamide Tert-butyl-4-[1-{[4-(2-butynyloxy) phenyl]sulfonyl}-2-(hydroxy amino)-2-oxoethyl]-1-piperidine carboxylate (160 mg, 0.34 mmol) was dissolved in methanolic HCl (50 ml) and allowed to stir at room temperature for 1 hour. The mixture was concentrated. After overnight drying, 80 mg of 2-{[4-(2-butynyloxy) phenyl] sulfonyl}-N-hydroxy-2-(4-piperidinyl) acetamide was isolated as a pink powder. mp: 140° C.; Yield: 59%; MS: 367.2 (M+H)$^+$; $^1$H NMR (300 MHz, DMSO-d$_6$): δ1.46–1.70 (band, 3H), 1.85 (t, 3H), 2.16–2.30 (band, 2H), 2.87 (m, 2H), 3.21 (m, 2H), 3.79 (d, J=8.79 Hz, 1H), 4.88 (d, J=2.28 Hz, 2H), 7.17 (d, J=9 Hz, 2H), 7.77 (d, J=9 Hz, 2H), 8.52 (m, 1H), 8.73 (m, 1H), 9.18 (s, 1H), 10.9 (s, 1H).

EXAMPLE 119

2-{[4-(2-butynyloxy)phenyl]sulfonyl}-N-hydroxy-2-[1-(4-methoxybenzyl)-4piperidinyl]acetamide Ethyl {[4-(2-butynyloxy)phenyl]sulfonyl}-(4-piperidinyl)acetate was prepared according to the general method as outlined in example 113 (step 1), starting from tert-butyl-4-(1-{[4-(2-butynyloxy) phenyl]sulfonyl}-2-ethoxy-2-oxoethyl)-1-piperidine carboxylate (2.5 g, 5.2 mmol); 1.88 g yellow solid. Yield 87%; MS: 380.2 (M+H)$^+$
Step 2
Ethyl {[4-(2-butynyloxy)phenyl]sulfonyl}[1-(4-methoxybenzyl)-4-piperidinyl]acetate To a solution of ethyl {[4-(2-butynyloxy)phenyl]sulfonyl}(4-piperidinyl) acetate (1.08, 2.86 mmol) in chloroform (150 ml), triethylamine (2 ml) and p-methoxy benzyl chloride (0.39 ml, 2.86 mmol) was added. The mixture was heated at reflux overnight.

The mixture was extracted in chloroform and washed twice with water. The organic layer was dried over Na$_2$SO$_4$, filtered and concentrated. The residue was purified using silica-gel column chromatography by eluting it with 50% ethyl acetate: hexane solution. Ethyl {[4-(2-butynyloxy)phenyl]sulfonyl}[1-(4-methoxybenzyl)-4-piperidinyl]acetate was isolated as a yellow oil (650 mg). Yield 46%; MS: 500.1 (M+H)$^+$ {[4-(2-butynyloxy)phenyl]sulfonyl}[-(4-methoxybenzyl)-4-piperidinyl]acetic acid was prepared according to the general method as outlined in example 1 (step 5), starting from ethyl {[4-(2-butynyloxy)phenyl]sulfonyl}[1-(4-methoxybenzyl)-4-piperidinyl]acetate (650 mg, 1.3 mmol); 540 mg white solid. Yield 88%; MS: 472.1 (M+H)$^+$ Starting from {[4-(2-butynyloxy)phenyl]sulfonyl}[1-(4-methoxybenzyl)-4-piperidinyl]acetic acid (430 mg, 0.913 mmol), and following the procedure as outlined in Example 1 (step 6), 220 mg of 2-{[4-(2-butynyl oxy) phenyl]sulfonyl}-N-hydroxy-2-[1-(4-methoxybenzyl)-4-piperidinyl]acetamide was isolated as a white solid. mp: 138° C.; Yield: 50%; MS: 487.1 (M+H)$^+$; $^1$H NMR (300 MHz, DMSO-d$_6$): δ1.67 (m, 3H), 1.85 (t, J=2.04 Hz, 3H), 2.12–2.26 (band, 2H), 2.86 (m, 2H), 3.17 (s, 1H), 3.27 (m, 2H), 3.77 (s, 3H), 4.12 (m, 2H), 4.88 (d, J=2.22 Hz, 2H), 6.99 (d, J=8.4 Hz, 2H), 7.16 (d, J=9 Hz, 2H), 7.46 (d, J=8.7 Hz, 2H), 7.77 (d, J=8.7 Hz, 2H), 10.32 (s, 10.87 (s, 1H).

EXAMPLE 120

2-(1-benzoyl-4piperidinyl)-2-{[4-(2-butynyloxy) phenyl]sulfonyl}-N-hydroxyacetamide
Step 1

Ethyl (1-benzoyl-4-piperidinyl){[4-(2-butynyloxy)phenyl]sulfonyl}acetate To a solution of ethyl {[4-(2-butynyloxy)phenyl]sulfonyl}(4-piperidinyl) acetate (2 g, 4.8 mmol) in methylene chloride (100 ml) in an ice water bath, triethylamine (1.34 ml, 9.6 mmol) was added. Benzoyl chloride (0.56 ml, 4.8 mmol) was added dropwise keeping the temperature at 0° C. The mixture was warmed to room temperature and stirred overnight before it was concentrated. The residue was extracted in chloroform and washed twice with water. The organic layer was dried over Na$_2$SO$_4$, filtered and concentrated. Ethyl (1-benzoyl-4-piperidinyl){[4-(2-butynyloxy) phenyl]sulfonyl}acetate was isolated using silica-gel column chromatography by eluting it with 50% ethyl acetate: hexane solution; yellow solid (1.8 g). mp: 120° C.; Yield 72%; MS: 484.1 (M+H)$^+$ (1-benzoyl-4-piperidinyl){[4-(2-butynyloxy) phenyl]sulfonyl}acetic acid was prepared according to the general method as outlined in example 1 (step 5) starting from ethyl (1-benzoyl-4-piperidinyl)([4-(2-butynyloxy) phenyl]sulfonyl) acetate (1.39 g, 2.88 mmol); 1.3 g white solid. mp:90° C.; Yield 99%; MS: 456.1 (M+H)$^+$ Starting from (1-benzoyl-4-piperidinyl){[4-(2-butynyloxy) phenyl]sulfonyl}acetic acid (1.22 g, 2.68 mmol), and following the procedure as outlined in Example 1 (step 6), 860 mg of 2-(1-benzoyl-4-piperidinyl)-2-{[4-(2-butynyloxy) phenyl]sulfonyl}-N-hydroxyacetamide was isolated as a white powder. mp: 224° C.; Yield: 68%; MS: 470.9 (M+H)$^+$; $^1$H NMR (300 MHz, DMSO-d$_6$): δ1.16–1.62 (band, 3H), 1.84 (t, J=2.1 Hz, 3H), 2.06–2.24 (band, 2H), 2.73–2.99 (band, 2H), 3.52 (m, 1H), 3.71 (d, J=8.61, 1H), 4.37 (m, 1H), 4.88 (d, J=2.28 Hz, 2H), 7.17 (d, J=8.7 Hz, 2H), 7.34 (m, 2H), 3H), 7.77 (d, J=8.7 Hz, 2H), 9.14 (s, 1H), 10.7 (s, 1H).

EXAMPLE 121

2-(1-acetyl-4piperidinyl)-{[4-(2-butynyloxy)phenyl] sulfonyl}-N-hydroxyacetamide Ethyl (1-acetyl-4-piperidinyl){[4-(2-butynyloxy) phenyl]sulfonyl}acetate was prepared according to the general method as outlined in example 116 (step 1), starting from ethyl {[4-(2-butynyloxy)phenyl]sulfonyl}(4-piperidinyl) acetate (1.5 g, 3.61 mmol) and acetyl chloride (0.26 ml, 3.61 mmol); yellow oil (1.35 g). Yield 89%; MS: 422 (M+H)$^+$ (1-acetyl-4-piperidinyl){[4-(2-butynyloxy) phenyl]sulfonyl) acetic acid was prepared according to the general method as outlined in example 1 (step 5), starting from ethyl (1-acetyl-4-piperidinyl){[4(2-butynyloxy) phenyl]sulfonyl}acetate (1.23 g, 2.92 mmol); 400 mg white gel. Yield 35%; MS: 391.9 (M−H)$^-$ Starting from (1-acetyl-4-piperidinyl){[4-(2-butynyloxy) phenyl]sulfonyl}acetic acid (290 mg, 0.74 mmol), and following the procedure as outlined in Example 1 (step 6), 60 mg of 2-(1-acetyl4-piperidinyl)-2-{[4-(2-butynyloxy) phenyl]sulfonyl}-N-hydroxyacetamide was isolated as an off white powder. mp: 103° C.; Yield: 20%; MS: 408.9 (M+H)$^+$; $^1$H NMR (300 MHz, DMSO-d$_6$): δ1.07–1.55 (m, 3H), 1.85 (s, 3H), 1.95 (m, 3H), 2.18 (m, 2H), 3.02 (m, 2H), 3.67–3.76 (band, 1H), 4.29 (m, 1H) (d, 2H), 7.16 (t, 2H), 7.78 (t, 2H), 9.15 (d, 1H), 10.7 (s, 1H).

EXAMPLE 122

2-{[4-(2-Butynyloxy)phenyl]sulfonyl}-N-hydroxy-2-tetrahydro-2H-pyran-4yl-acetamide
Step 1

Ethyltetrahydro-4Hpyran4-ylideneacetate was prepared from tetrahydro pyran-4-one (9.0 g 90 mmol) and diethylphosphonoethylacetate (20.16 g, 90 mmol) in DMF/K$_2$CO$_3$ at 80° C. Colorless oil, Yield. 16.3 g, (96%), MS: 171 (M+H)$^+$
Step 2

Ethyltetrahydro-4Hpyran-4-ylacetate was prepared from ethyltetra hydro-4Hpyran-4-ylideneacetate (16.0 g, 94 mmol) and Pd/NH$_4$COOH at 800° C. Colorless oil Yield: 16.3 g, quantitaive), MS: 173.2 M+H)$^+$
Step 3

2-{[4-(2-Butynyloxy)phenyl]sulfonyl}(tetrahydro-2H-pyran-4yl)-ethylacetate was prepared according to the general method as outlined in Example 113 (step 1). Starting from ethyltetrahydro4Hpyran4-ylacetate (4.0 g, 23.3 mmol) and 4-but-2-ynyl oxy-benzenesulfonyl fluoride(7.1 g, 26.0 mmol), 7 0 g of product was isolated as yellow oil. Product was purified by silica-gel column chromatography by eluting it with 50% ethyl acetate: hexane. Yield: 89%, MS: 381 (M+H)$^+$
Step 4

2-{[4-(2-Butynyloxy)phenyl]sulfonyl}(tetrahydro-2H-pyran-4yl)-acetic acid was prepared according to the general method as outlined in Example 1 (step 5). Starting from 2-{[4-(2-Butynyloxy)phenyl]sulfonyl}(tetrahydro-2H-pyran-4yl}ethylacetate (7.0 g, 18.4 mmol), 6.1 g of product was isolated. Yield: quantitative; MS: 351.4 (M–H)$^+$ Step 5

2-{[4-(2-Butynyloxy)phenyl]sulfonyl}-N-hydroxy-2-tetrahydro-2H-pyran-4yl-acetamide was prepared according to the general method as outlined in example 1 (step 6). Starting from 2-{[4-(2-butynyloxy)phenyl]sulfonyl}(tetrahydro-2H-pyran- 4yl)-acetic acid (4.0 g, 11.4 mmol), 3.4 g of the product was isolated. The product was purified by silica-gel column chromatography by eluting it with 75% ethyl acetate: hexane. White solid, Mp. 208–211, Yield: 84%; MS: 368.4 (M–H)$^+$; $^1$H NMR (300 MHz, DMSO-d$_6$): δ1.25 (m, 2H), 1.42–1.66 (m, 414), 2.45 (m, 2H), 4.66 (s, 2H), 4.68 (d, 1H), 5.15 (m, 1H), 6.82 (d, 2H),7.41 (d, 2H),9.15 (bs, 1H).

EXAMPLE 123

2-{[4-(2-Butynyloxy)phenyl]sulfonyl}-N-hydroxy-2-tetrahydro-2H-thiopyran-4yl-acetamide Step 1

Ethyltetrahydro-4Hthiopyran-4-ylideneacetate was prepared from tetrahydro thiopyran-4-one (10.0 g 86 mmol) and diethylphosphonoethylacetate (21.2 g, 95 mmol) in DMF/K$_2$CO$_3$ at 80° C. Colorless oil, Yield. 15.4 g, (96%), MS: 187 (M+H)$^+$ Step 2

Ethyltetrahydro-4Hthiopyran-4-ylacetate was prepared from ethyltetra hydro-4Hthiopyran-4-ylideneacetate (8.0 g, 43 mmol), NaBH$_4$ (8.2 g, 5equivalents) and NiCl$_2$ (5.0 g) at 0° C. for 1 hr. Colorless oil, Yield: 8.1 g, quantitaive), MS: 189 (M+H)$^+$ Step 3

2-{[4-(2-Butynyloxy)phenyl]sulfonyl}(tetrahydro-2H-thiopyran-4yl)-ethylacetate was prepared according to the general method as outlined in Example 113 (step 1). Starting from ethyltetrahydro-4Hthiopyran-4-ylacetate (5.0 g, 26.6 mmol) and 4-but-2-ynyl oxy-benzenesulfonyl fluoride(5.5 g, 26.0 mmol), 9.3 g of product was isolated as yellow oil. Product was purified by silica-gel column chromatography by eluting it with 50% ethyl acetate: hexane Yield: 88%, MS: 398 (M+H)$^+$ Step 4

2-{[4-(2-Butynyloxy)phenyl]sulfonyl}(tetrahydro-2H-thiopyran-4yl)-acetic acid was prepared according to the general method as outlined in Example 1 (step 5). Starting from 2-{[4-(2-Butynyloxy)phenyl]sulfonyl}(tetrahydro-2H-thiopyran-4yl)-ethylacetate (7.0 g, 17.7 mmol), 6.8 g of product was isolated as white solid. Mp: 141–3Yield: quantitative; MS: 370 (M–H)$^+$ Step 5

2-{[4-(2-Butynyloxy)phenyl]sulfonyl}-N-hydroxy-2-tetrahydro-2H-thiopyran-4yl-acetamide was prepared according to the general method as outlined in example 1 (step 6). Starting from 2-{[4-(2-butynyloxy) phenyl]sulfonyl}(tetrahydro-2H-thiopyran-4yl)-acetic acid (4.5 g, 12.2 mmol), 4.6 g of product was isolated. The product was purified by silica-gel column chromatography by eluting it with 1:1 ethyl acetate: hexane. White solid, Mp. 175–177, Yield: 98%; MS: 385 (M–H)$^+$; $^1$H NMR (300 MHz, DMSO-d$_6$): δ1.52 (m, 2H), 1.81 (s, 3H), 2.1 (m, 1H), 2.22 (m, 1H), 2.38 (m, 1H), 2.69 (m, 4H), 3.73 (d, 1H), 4.71 (s, 2H), 7.05 (d, 2H),7.79 (d, 2H),9.18 (bs, 1H), 10.62 (s, 1H).

EXAMPLE 124

2-{[4-(2-Butynyloxy)phenyl]sulfonyl}-N-hydroxy-2-(1-oxidotetrahydro-2H-thiopyran-4yl) acetamide 2-{[4-(2-Butynyloxy)phenyl]sulfonyl}-N-hydroxy-2-(1-oxidotetrahydro-2H-thiopyran-4yl) acetamide was prepared, starting from 2-{[4-(2-Butynyloxy)phenyl]sulfonyl}-N-hydroxy-2-tetrahydro-2H-thiopyran-4yl-acetamide (0.6 g, 1.6 mmol), and following the procedure as outlined in Example 7, 600 mg of the product was isolated as a white solid. Mp: 219–220° C.; Yield: Quantitative; MS: 401 (M+H)$^+$. $^1$H NMR (300 MHz, DMSO-d$_6$): δ1.82 (s, 3H), 1.83–1.85 (m, 1H), 2.02–2.08 (m, 1H), 2.18–2.33 (m, 1H), 2.61–2.68 (m, 2H), 2.72–2.76 (m, 1H), 3.15–3.22 (m, 1H), 3.31 (s, 2H), 3.72 (d, 1H), 4.91 (s, 2H), 7.18 (d, 2H),7.75 (d, 2H),9.21 (bs, 1H), 10.78 (s, 1H).

EXAMPLE 125

2-{[4-(2-Butynyloxy)phenyl]sulfonyl}-N-hydroxy-2-(1,1-dioxidotetrahydro-2H-thiopyran-4yl) acetamide Starting from 2-{[4-(2-Butynyloxy)phenyl]sulfonyl}-N-hydroxy-2-tetrahydro-2H-thiopyran-4yl-acetamide (0.5 g, 1.3 mmol), and following the procedure as outlined in Example 75, 0.45 g of 2-{[4-(2-Butynyloxy)phenyl]sulfonyl}-N-hydroxy-2-(1,1-dioxidotetrahydro-2H-thiopyran-4yl) acetamide was isolated as a white powder. Yield: 93% MS: 417 (M+H)$^+$; $^1$H NMR (300 MHz, DMSO-d$_6$): δ1.88 (s, 3H), 2.12 (m, 1H), 2.15–2.23 (m, 2H), 2.55 (m, 2H), 2.92–3.15 (m, 4H), 3.87 (d, 1H), 4.72 (s, 2H), 7.02 (d, 2H), 7.82 (d, 2H), 9.2 (bs, 1H).

Pharmacology

Representative compounds of this invention were evaluated as inhibitors of the enzymes MMP-1, MMP-9, MMP-13 and TNF-a converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM CaCl$_2$) before use. The stock of enzyme is diluted with buffer (50 mM HEPES, pH 7.5, 5 mM CaCl$_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM Ca$^{+2}$, 0.02% 3Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2 > 0.85$). The mean (x±sem) of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2 > 0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay For Soluble Proteins (THP Soluble Protein Assay)

Mitogenic stimulation of THP-1 cells cause differentiation into macrophage like cells with concomitant secretion of tumor necrosis factor (TNF-α) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-α converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at 5×106/ml/vial. One vial is seeded into a T25-flask with 16 mls of RPMI-1640 with glutamax (Gibco) media containing 10% fetal bovine serum, 100 units/ml penicillin, 100 μg/ml streptomycin, and $5 \times 10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml.

To perform an assay, the THP-1 cells are co-incubated in a 24 well plate with 50 ml/well of a 24 mg/ml stock of Lipopolysacharide (LPS) (Calbiochem Lot# B13189) at 37,C in 5% $CO_2$ at a concentration of 1.091×106 cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-α ELISA. Following 24 hours of incubation, 700 ml/well of TCS is removed and used for analysis in TNF-R p75/80, TNF-R p55160 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. #1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-α, TNF-R p75180 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml (compound)} - \text{pg/ml (veh pos control)}}{\text{pg/ml (veh pos control)} - \text{pg/ml (veh neg control)}} \times 100$$

For the soluble protein (TNF-α, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml (compound neg control)} - \text{pg/ml (veh pos control)}}{\text{pg/ml (veh neg control)}} \times 100$$

IC50 values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

REFERENCE

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-I cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in vitro matrix metalloproteinase inhibition, TACE inhibition and THP standard pharmacological test procedures are given in Table 1 below.

TABLE 1

| Example # | TACE IC$_{50}$ (nM) | THP (% inhibition) | MMP1 IC$_{50}$ (μM) | MMP9 IC$_{50}$ (nM) | MMP13 IC$_{50}$ (nM) |
|---|---|---|---|---|---|
| 1 | 191 | 25% | 2 | 180 | 200 |
| 2 | 207 | 5% | 2.2 | 207 | 597 |
| 3 | 15.7 | 14% | 1.4 | 142 | 69 |
| 4 | 47.2 | 2% | IA | IA | IA |
| 5 | 74.8 | 6% | 10 | 2500 | 500 |
| 6 | 105 | 5% | 15 | 3000 | 2000 |
| 7 | 4.3 | 67% | 3 | 1500 | 900 |
| 8 | 12.4 | 35% | 3.2 | 1000 | 150 |
| 9 | 30 | 16% | 10 | 10,000 | 10,000 |
| 10 | 610 | NT | 10 | 10,000 | 10,000 |
| 11 | 20% | NT | 10 | 10,000 | 10,000 |
| 12 | 14% | NT | 10 | 10,000 | 10,000 |
| 13 | 42.5 | | | | |
| 14 | 62.9 | | | | |
| 15 | 137.9 | | | | |
| 16 | 24.9 | | | | |
| 17 | 43.7 | | | | |
| 18 | 36.9 | | | | |
| 19 | 43.3 | | | | |
| 20 | 88.6 | | | | |
| 21 | 20.1 | | | | |
| 22 | 32.8 | | | | |
| 23 | 20.5 | | 3.3 | | |
| 24 | 30.0 | | | | |
| 25 | 43.5 | | | | |
| 26 | 29.9 | | | | |
| 27 | 46.3 | | | | |
| 28 | 26.6 | | | | |
| 29 | 18.9 | | 2.0 | | |
| 30 | 20.1 | | 3.3 | | |
| 31 | 28.3 | | | | |
| 32 | 46.8 | | | | |
| 33 | 35.6 | | | | |
| 34 | 146.8 | | | | |
| 35 | 68.3 | | | | |
| 36 | 16.8 | | | | |
| 37 | 43.7 | | | | |
| 38 | 39.9 | | | | |
| 39 | 65.1 | | | | |
| 40 | 59.1 | | | | |
| 41 | 37.3 | | | | |
| 42 | 24.9 | | | | |
| 43 | 32.5 | | | | |
| 44 | 32.1 | | | | |
| 45 | 16.1 | | | | |
| 46 | 84.2 | | | | |
| 47 | 18.9 | | | | |
| 48 | 82.1 | | | | |
| 49 | 53.8 | | | | |
| 50 | 35.9 | | | | |
| 51 | 22.4 | | | | |
| 52 | 70.2 | | | | |
| 53 | 15.2 | | 4.0 | | |
| 54 | 27.2 | | | | |
| 55 | 38.5 | | | | |
| 56 | 21.9 | | 3.9 | | |
| 57 | 24.4 | | 4.6 | | |
| 58 | 20.1 | | 4.6 | | |
| 59 | 22.6 | | 3.4 | | |
| 60 | 40.9 | | | | |
| 61 | 22.5 | | 5.6 | | |
| 62 | 31.9 | | | | |
| 63 | 16.1 | | | | |
| 64 | 42.0 | | | | |
| 65 | 52.1 | | | | |
| 66 | 145.3 | | | | |
| 67 | 34.8 | | | | |
| 68 | 21.2 | | | | |
| 69 | 29.2 | | | | |
| 70 | 88.1 | | | | |

| Compound | TACE IC$_{50}$[a] | MMP9[a] | MMP13[a] | MMP1[a] | TNFalpha at 3 uM[b] |
|---|---|---|---|---|---|
| Example 71 | | 2514 nm | 894 nm | 10 um | −11% |
| Example 72 | 14.2 | 1363 nm | 341 nm | 46.20% | −54% |

TABLE 1-continued

| Example | | | | | |
|---|---|---|---|---|---|
| Example 73 | 119 | 55.90% | 55.90% | 4.80% | 0 |
| Example 74 | 52 | 336 nm | 93.5 nm | 1502 nm | -31% |
| Example 75 | 26.7 | 68.20% | 708 nm | 34.60% | -39% |
| Example 76 | 50.7 | 21.60% | 26.80% | 3% | -15% |
| Example 77 | 201 | 45.40% | 3687 nm | 17.50% | -12% |
| Example 78 | 17.6 | 32.70% | 54.50% | 5.90% | -13% |
| Example 79 | 48.1 | 27.30% | 56.80% | 23.30% | -14% |
| Example 80 | 102 | 10.90% | 48.80% | 0.00% | -4% |
| Example 81 | 223 | NT | 21.6% (1 um) | 30.50% | -6% |
| Example 82 | 108 | 38% | 5057 nm | 27.10% | -14% |
| Example 83 | 133 | NT | 36.40% | 9.40% | 0 |
| Example 84 | 145 | NT | 23% (1 um) | 10% | 70% |
| Example 85 | 391 | NT | 30.50% | 6.80% | 10% |
| Example 86 | 60 | NT | 51% | 24% | 2% |
| Example 87 | 336 | NT | 33% (1 um) | 17% | 5% |
| Example 88 | 226 | NT | 21% (1 um) | 20% | -4% |
| Example 89 | 617 | NT | 5% | 0 | -2% |
| Example 90 | 682 | NT | 16% (1 um) | 7% | -1% |
| Example 91 | 48% | NT | 35% | 10% | -2% |
| Example 92 | 931 | NT | 25% | 8% | 7% |
| Example 93 | 15.63% | NT | 17% | 7% | 1% |
| Example 94 | 423 | NT | 34% | 8% | 11% |
| Example 95 | 108 nm | 5.70% | 26% | 9% | 7% |
| Example 96 | 148 | 0 | 53.40% | 18.40% | -12% |
| Example 97 | 109 | 0.50% | 47.40% | 0.50% | -10% |
| Example 98 | 464 | NT | 59% | 23% | -1% |
| Example 99 | 1.1 um | NT | 33.60% | 0 | -1% |
| Example 100 | 100 | NT | 15% | 2% | 0% |
| Example 101 | 76 | NT | 51% | 8% | 1% |
| Example 102 | 82 | NT | 71% | 26% | -10% |
| Example 103 | 113 | NT | 12% | 4% | 15% |
| Example 104 | 63 | NT | 54% | 6% | -4% |
| Example 105 | 106 | NT | 32% | 9% | 4% |
| Example 106 | 65 | NT | 56% | 0 | 5% |
| Example 107 | 157 | 56.80% | 59.40% | 2.80% | 13% |
| Example 108 | 48 | 399 nm | 216 nm | 6477 nm | -29% |
| Example 109 | 49 | 893 nm | 107 nm | 2992 nm | -20% |
| Example 110 | 17 | 5141 nm | 1262 nm | 39.60% | -25% |
| Example 111 | 50 | 13.50% | 0.80% | 6.60% | 10% |
| Example 112 | 28 | 8.20% | 23.60% | 9.90% | -15% |
| Example 113 | 162 | 25.70% | 59% | 6.20% | -4% |
| Example 114 | 40.90% | NT | 30.50% | 3.50% | -12% |
| Example 115 | 141 | NT | 45.1% (1 um) | 4.11% | -11% |
| Example 116 | 495 | NT | 33.6% (1 um) | 5.60% | -7% |
| Example 117 | 190 | NT | 52% | 22% | -50% |
| Example 118 | 299 | NT | 69.50% | 23.80% | -24% |
| Example 119 | 263 | NT | 50% | 9% | -30% |
| Example 120 | 88.5 | NT | 51% (1 um) | 24% | -63% |
| Example 121 | | | | | |
| Example 122 | 51.4 | NT | 57% | 9% | -36% |
| Example 123 | | | | | |
| Example 124 | | | | | |
| Example 125 | | | | | | a is % @ 10 μM or IC50 (nM), unless otherwise specified
b is THP (percent change)

Based on the results obtained in the standard pharmacological test procedures described above, the compounds of this invention were shown to be inhibitors of the enzymes MMP-1, MMP-9, MMP-13 and TNF-α converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerosis plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound of formula

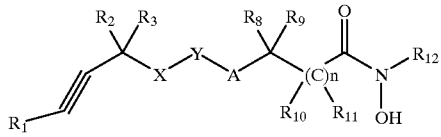

wherein:

R$_1$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, or C$_5$–C8-cycloheteroalkyl having from 1–2 heteroatoms selected from N, NR$_7$, S and O;

R$_2$ and R$_3$ are each independently, hydrogen, alkyl of 1–6 carbon atoms, —CN, or —CCH;

R$_5$ is hydrogen, alkyl of 1–8 carbon atoms, cycloalkyl of 3–6 carbon atoms, aryl, heteroaryl, or C4–C8-cycloheteralkyl;

R$_7$ is hydrogen, aryl, aralkyl, alkyl of 1–6 carbon atoms, or cycloalkyl of 3–6 carbon atoms, oxy, C1–C8 alkanoyl, COOR$_5$, COR$_5$, —SO$_2$—C1–C8 alkyl, —SO$_2$-aryl, —SO$_2$-heteroaryl, —CO—NHR$_1$;

R$_8$, R$_9$, R$_{10}$, and R$_{11}$ are each, independently, hydrogen, aryl, aralkyl, 5–10 membered heteroaryl having from 1–3 heteroatoms selected from N, NR$_7$, O and S, heteroaralkyl having from 1–3 heteroatoms selected from N, NR$_7$, O and S, cycloalkyl of 3–6 carbon atoms, —C$_4$–C$_8$-cycloheteroalkyl having from 1–3 heteroatoms selected from N, NR$_7$, O and S, alkyl of 1–18 carbon atoms, alkenyl of 2–18 carbon atoms, alkynyl of 2–18 carbon atoms;

R$_{12}$ is hydrogen, aryl or 5–10 membered heteroaryl having from 1–3 heteroatoms selected from N, NR$_7$, S and O, cycloalkyl of 3–6 carbon atoms, —C$_5$–C8-cycloheteroalkyl having from 1 to 2 heteroatoms selected from N, NR$_7$, S and O, or alkyl of 1–6 carbon atoms;

A is O, S, SO, SO$_2$, NR$_7$, or CH$_2$;

X is O, S, SO, SO$_2$, NR$_7$, or CH$_2$;

Y is phenyl, with the proviso that A and X are not bonded to adjacent atoms of Y; and n is 0–2; or a pharmaceutically acceptable salt thereof.

2. A compound of claim 1 wherein R$_2$ and R$_3$ are each, independently, hydrogen or alkyl of 1–6 carbon atoms; and R$_{12}$ is hydrogen.

3. A method of inhibiting pathological changes mediated by TNF-α converting enzyme (TACE) in a mammal in need thereof which comprises administering to said mammal a therapeutically effective amount of a compound having the formula:

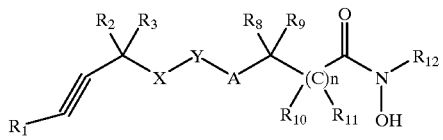

wherein:

R$_1$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, or C$_5$–C8-cycloheteroalkyl having from 1–2 heteroatoms selected from N, NR$_7$, S and O;

R$_2$ and R$_3$ are each independently, hydrogen, alkyl of 1–6 carbon atoms, —CN, or —CCH;

R$_5$ is hydrogen, alkyl of 1–8 carbon atoms, cycloalkyl of 3–6 carbon atoms, aryl, heteroaryl, or C4–C8-cycloheteralkyl;

R$_7$ is hydrogen, aryl, aralkyl, alkyl of 1–6 carbon atoms, or cycloalkyl of 3–6 carbon atoms, oxy, C1–C8 alkanoyl, COOR$_5$, COR$_5$, —SO$_2$—C1–C8 alkyl, —SO$_2$-aryl, —SO$_2$-heteroaryl, —CO—NHR$_1$;

R$_8$, R$_9$, R$_{10}$, and R$_{11}$ are each, independently, hydrogen, aryl, aralkyl, 5–10 membered heteroaryl having from 1–3 heteroatoms selected from N, NR7, O and S, heteroaralkyl having from 1–3 heteroatoms selected from N, NR$_7$, O and S, cycloalkyl of 3–6 carbon atoms, —C$_4$–C$_8$-cycloheteroalkyl having from 1–3 heteroatoms selected from N, NR$_7$, O and S, alkyl of 1–18 carbon atoms, alkenyl of 2–18 carbon atoms, alkynyl of 2–18 carbon atoms;

R$_{12}$ is hydrogen, aryl or 5–10 membered heteroaryl having from 1–3 heteroatoms selected from N, NR$_7$, S and O, cycloalkyl of 3–6 carbon atoms, —C$_5$–C8-cycloheteroalkyl having from 1 to 2 heteroatoms selected from N, NR$_7$, S and O, or alkyl of 1–6 carbon atoms;

A is O, S, SO, SO$_2$, NR$_7$, or CH$_2$;
X is O, S, SO, SO$_2$, NR$_7$, or CH$_2$;
Y is phenyl, with the proviso that A and X are not bonded to adjacent atoms of Y; and
n is 0–2; or a pharmaceutically acceptable salt thereof.

4. A pharmaceutical composition comprising a compound having the formula:

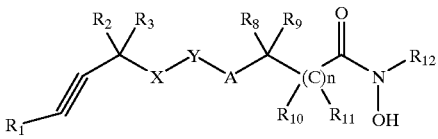

wherein:
R$_1$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms, or C$_5$–C8-cycloheteroalkyl having from 1–2 heteroatoms selected from N, NR$_7$, S and O;

R$_2$ and R$_3$ are each independently, hydrogen, alkyl of 1–6 carbon atoms, —CN, or —CCH;

R$_5$ is hydrogen, alkyl of 1–8 carbon atoms, cycloalkyl of 3–6 carbon atoms, aryl, heteroaryl, or C4–C8-cycloheteralkyl;

R$_7$ is hydrogen, aryl, aralkyl, alkyl of 1–6 carbon atoms, or cycloalkyl of 3–6 carbon atoms, oxy, C1–C8 alkanoyl, COOR$_5$, COR5, —SO$_2$—C1–C8 alkyl, —SO$_2$-aryl, —SO$_2$-heteroaryl, —CO—NHR$_1$;

R$_8$, R$_9$, R$_{10}$, and R$_{11}$ are each, independently, hydrogen, aryl, aralkyl, 5–10 membered heteroaryl having from 1–3 heteroatoms selected from N, NR7, O and S, heteroaralkyl having from 1–3 heteroatoms selected from N, NR$_7$, O and S, cycloalkyl of 3–6 carbon atoms, —C$_4$–C$_8$-cycloheteroalkyl having from 1–3 heteroatoms selected from N, NR$_7$, O and S, alkyl of 1–18 carbon atoms, alkenyl of 2–18 carbon atoms, alkynyl of 2–18 carbon atoms;

R$_{12}$ is hydrogen, aryl or 5–10 membered heteroaryl having from 1–3 heteroatoms selected from N, NR7, S and O, cycloalkyl of 3–6 carbon atoms, —C$_5$–C8-cycloheteroalkyl having from 1 to 2 heteroatoms selected from N, NR7, S and O, or alkyl of 1–6 carbon atoms;

A is O, S, SO, SO$_2$, NR$_7$, or CH$_2$;
X is O, S, SO, SO$_2$, NR$_7$, or CH$_2$;
Y is phenyl, with the proviso that A and X are not bonded to adjacent atoms of Y; and
n is 0–2; or a pharmaceutically acceptable salt thereof.

5. The compound according to claim 1 selected from the group consisting of:

2-(4-But-2-ynyloxy-benzenesulfonyl)-N-hydroxy-2-methyl-3-[4-(2-piperidin-1-yl-ethoxy)phenyl]-propionamide;

3- Biphenyl-4-yl-2-(4-Buty-2-ynyloxy-phenylsulfonyl)-N-hydroxy-2-methyl-propionamide;

2-(4-Buty-2-ynyloxy-phenylsulfonyl)-N-hydroxy-2-methyl-3-pyridin-3-ylpropionamide;

2-(4-Buty-2-ynyloxy-phenylsulfanyl)-N-hydroxy-propionamide;

2-(4-But-2-ynyloxy-benzenelsulfonyl)-octanoic acid hydroxamide;

2-(4-But-2-ynyloxy-phenylsulfanyl)-octanoic acid hydroxamide;

(S)-2-{(R)-[4--(2-Butynyloxy)phenylsulfinyl]}-N-hydroxyoctanamide;

(S)-2-{(S)-[4--(2-Butynyloxy)phenylsulfinyl]}-N-hydroxyoctanamide;

3-(4-But-2-ynyloxy-phenoxy)-N-hydroxy-propionamide;

4-(4-But-2-ynyloxy-phenoxy)-N-hydroxy-butyramide;

2-(4-But-2-ynyloxy-phenoxy)-N-hydroxy-acetamide;

4-(4-But-2-ynyloxy-phenyl)-N-hydroxy-butyramide;

2-(4-But-2-ynyloxy-phenylsulfanyl)-6-[2-(1,3-dioxo-1,3-dihydroiso-indol-2-yl)-acetylamino]-hexanoic acid hydroxyamide;

Quinoline-2-carboxylic acid [5-(4-but-2-ynyloxy-phenylsulfanyl)-5-hydroxycarbamoyl-pentyl]-amide;

N-[5-(4-But-2-ynyloxy-phenylsulfanyl)-5-hydroxycarbamoyl-pentyl]-2-phenethyl-benzamide;

2-(4-But-2-ynyloxy-phenylsulfanyl)-6-[2-(3,4-dichloro-phenyl)-acetylamino]-hexanoic acid hydroxyamide;

Quinoline-3-carboxylic acid [5-(4-but-2-ynyloxy-phenylsulfanyl)-5-hydroxycarbamoyl-pentyl]-amide;

2-(4-But-2-ynyloxy-phenylsulfanyl)-6-(4-thiophen-2-yl-butyrylamino)-hexanoic acid hydroxyamide;

9H-Xanthene-9-carboxylic acid [5-(4-but-2-ynyloxy-phenylsulfanyl)-5-hydroxycarbamoyl-pentyl]-amide;

2-(4-But-2-ynyloxy-phenylsulfanyl)-6-diphenylacetylamino-hexanoic acid hydroxyamide;

Isoquinoline-1-carboxylic acid [5-(4-but-2-ynyloxy-phenylsulfanyl)-5-hydroxycarbamoyl-pentyl]-amide;

6-(2-Benzo[b]thiophen-3-yl-acetylamino)-2-(4-but-2-ynyloxy-phenylsulfanyl)-hexanoic acid hydroxyamide;

Quinoline-2-carboxylic acid [5-(4-but-2-ynyloxy-benzenesulfinyl)-5-hydroxycarbamoyl-pentyl]-amide;

2-(4-But-2-ynyloxy-benzenesulfinyl)-6-[2-(1,3-dioxo-1,3-dihydro-isoindol-2-yl)-acetylamino]-hexanoic acid hydroxyamide;

N-[5-(4-But-2-ynyloxy-benzenesulfinyl)-5-hydroxycarbamoyl-pentyl]-2-phenethyl-benzamide;

2-(4-But-2-ynyloxy-benzenesulfinyl)-6-[2-(3,4-dichloro-phenyl)-acetylamino]-hexanoic acid hydroxyamide;

Quinoline-3-carboxylic acid [5-(4-but-2-ynyloxy-benzenesulfinyl)-5-hydroxycarbamoyl-pentyl]-amide;

2-(4-But-2-ynyloxy-benzenesulfinyl)-6-(4-thiophen-2-yl-butyrylamino)-hexanoic acid hydroxyamide;

9H-Xanthene-9-carboxylic acid [5-(4-but-2-ynyloxy-benzenesulfinyl)-5-hydroxycarbamoyl-pentyl]-amide;

2-(4-But-2-ynyloxy-benzenesulfinyl)-6-diphenylacetylamino-hexanoic acid hydroxyamide;

Isoquinoline-1-carboxylic acid [5-(4-but-2-ynyloxy-benzenesulfinyl)-5-hydroxycarbamoyl-pentyl]-amide;

6-(2-Benzo[b]thiophen-3-yl-acetylamino)-2-(4-but-2-ynyloxy-benzenesulfinyl)-hexanoic acid hydroxyamide;

2-(4But-2-ynyloxy-benzenesulfinyl)-6-(2-1H-indol-3-yl-acetylamino)-hexanoic acid hydroxyamide;

Quinoline-2-carboxylic acid [5-(4-but-2-ynyloxy-benzenesulfonyl)-5-hydroxycarbamoyl-pentyl]-amide;

2-(4-But-2-ynyloxy-benzenesulfonyl)-6-[2-(1,3-dioxo-1,3-dihydro-isoindol-2-yl)-acetylamino]-hexanoic acid hydroxyamide;

N-[5-(4-But-2-ynyloxy-benzenesulfonyl)-5-hydroxycarbamoyl-pentyl]-2-phenethyl-benzamide;

2-(4-But-2-ynyloxy-benzenesulfonyl)6-[2-(3,4-dichloro-phenyl)-acetylamino]-hexanoic acid hydroxyamide;

Quinoline-3-carboxylic acid [5-(4-but-2-ynyloxy-benzenesulfonyl)-5-hydroxycarbamoyl-pentyl]-amide;

9H-Xanthene-9-carboxylic acid [5-(4-but-2-ynyloxy-benzenesulfonyl)-5-hydroxycarbamoyl-pentyl]-amide;

2-(4-But-2-ynyloxy-benzenesulfonyl)-6-diphenylacetylamino hexanoic acid hydroxyamide;

Isoquinoline-1-carboxylic acid [5-(4-but-2-ynyloxy-benzenesulfonyl)-5-hydroxycarbamoyl-pentyl]-amide;

6-(2-Benzo[b]thiophen-3-yl-acetylamino)-2-(4-but-2-ynyloxy-benzenesulfonyl)-hexanoic acid hydroxyamide;

Quinoline-2-carboxylic acid {[5-(4-but-2-ynyloxy-phenylsulfanyl)-5-hydroxycarbamoyl-pentylcarbamoyl]-methyl}-amide;

2-(4-But-2-ynyloxy-phenylsulfanyl)-6-{2-[2-(1,3-dioxo-1,3-dihydro-isoindol-2-yl)-acetylamino]-acetylamino}-hexanoic acid hydroxyamide;

N-{[5-(4-But-2-ynyloxy-phenylsulfanyl)-5-hydroxycarbamoyl-pentylcarbamoyl]-methyl)-2-phenethyl-benzamide;

2-(4-But-2-ynyloxy-phenylsulfanyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-phenylsulfanyl)-5-hydroxycarbamoyl-pentylcarbamoyl]-methyl}-amide;

9H-Xanthene-9-carboxylic acid {[5-(4-but-2-ynyloxy-phenylsulfanyl)-5-hydroxycarbamoyl-pentylcarbamoyl]-methyl)-amide;

2-(4-But-2-ynyloxy-phenylsulfanyl)-6-(2-diphenylacetylamino-acetylamino)-hexanoic acid hydroxyamide;

Isoquinoline-1-carboxylic acid {[5-(4-but-2-ynyloxy-phenylsulfanyl)-5-hydroxycarbamoyl-pentylcarbamoyl]-methyl}-amide;

1-Methyl-1H-pyrrole-2-carboxylic acid {[5-(4-but-2-ynyloxy-phenylsulfanyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy-phenylsulfanyl hexanoic acid hydroxyamide;

Quinoline-2-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-{2-[2-(1,3-dioxo-1,3-dihydro-isoindol-2-yl)-acetylamino]-acetylamino}-hexanoic acid hydroxyamide;

N-{[5-(4-But-2-ynyloxy-benzenesulfinyl)-5-hydroxycarbamoyl-pentylcarbamoyl]-methyl}-2-phenethyl-benzamide;

2-(4-But-2-ynyloxy-benzenesulfinyl)-6-{2-[2-(3,4-dichloro-phenyl)-acetylamino-acetylamino}-hexanoic acid hydroxyamide;

Quinoline-3-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-[2-(4-thiophen-2-yl-butyrylamino)-acetylamino]-hexanoic acid hydroxyamide;

9H-Xanthene-9-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-(2-diphenylacetylamino-acetylamino)-hexanoic acid hydroxyamide;

1-Methyl-1H-pyrrole-2-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfonyl)-6-{2-[2-(1,3-dioxo-1,3-dihydro-isoindol-2-yl)-acetylamino]-acetylamino}-hexanoic acid hydroxyamide;

N-{[5-(4-But-2-ynyloxy-benzenesulfonyl)-5-hydroxycarbamoyl-pentylcarbamoyl]-methyl}-2-phenethyl-benzamide;

2-(4-But-2-ynyloxy-benzenesulfonyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-benzenesulfinyl)-5-hydroxycarbamoyl-pentylcarbamoyl]-methyl}-amide;

9H-Xanthene-9-carboxylic acid {[5-(4-but-2-ynyloxy-benzenesulfonyl)-5-hydroxycarbamoyl-pentylcarbamoyl]-methyl}-amide;

2-(4-But-2-ynyloxy-benzenesulfonyl)-6-(2-diphenylacetylamino-acetylamino)-hexanoic acid hydroxyamide;

Isoquinoline-1-carboxylic acid {[5-(4-but-2-ynyloxy-benzenesulfonyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy benzenesulfonyl hexanoic acid hydroxyamide;

2-(4-But-2-ynyloxy-benzenesulfonyl)-6-[$^2$-($^2$-1H-indol-3-yl-acetylamino)-acetylamino]-hexanoic acid hydroxyamide;

2-{[4-(2-butynyloxy)phenyl]sulfonyl}-N-hydroxy-4-{[2-(1-piperidinylethoxy phenyl}butanamide;

2-{[4-(2-butynyloxy)phenyl]sulfonyl}-7-cyano-N-hydroxy heptanamide;

2-{[4-(2-butynyloxy)phenyl]sulfanyl}-2-cyclohexyl-N-hydroxyacetamide;

2-{[4-(2-butynyloxy)phenyl]sulfinyl}-2-cyclohexyl-N-hydroxyacetamide;

2-{[4-(2-butynyloxy)phenyl]sulfonyl}-2-cyclohexyl-N-hydroxyacetamide;

2-{[4-(2-butynyloxy)phenyl]sulfanyl}-N-hydroxy-2-(4-methoxyphenyl)acetamide;

(2R)-2-{[4-(2-butynyloxy)phenyl]sulfinyl}-N-hydroxy-2-(4-methoxyphenyl)ethanamide;

(2S)-2-{[4-(2-butynyloxy)phenyl]sulfinyl}-N-hydroxy-2-(4-methoxyphenyl)ethanamide;

2-{[4-(2-butynyloxy)phenyl]sulfonyl}-N-hydroxy-2-(4-methoxyphenyl)acetamide;

2-{[4-(2-butynyloxy)phenyl]sulfanyl}-2-(4-chlorophenyl)-N-hydroxyacetamide;

2-{[4-(2-butynyloxy)phenyl]sulfinyl}-2-(4-chlorophenyl)N-hydroxyacetamide;

2-{[4-(2-butynyloxy)phenyl]sulfonyl}-2-(4-chlorophenyl)-N-hydroxyacetamide;

2-{[4-(2-butynyloxy)phenyl]sulfanyl}-2-(3-chlorophenyl)-N-hydroxyacetamide;

2-{[4-(2-butynyloxy)phenyl]sulfonyl}-2-(3-chlorophenyl)-N-hydroxyacetamide;

2-(4-bromophenyl)-2-{[4-(2-butynyloxy)phenyl]sulfanyl}-N-hydroxyacetamide;
(2S)-2-(4-bromophenyl)-2-{[4-(2-butynyloxy)phenyl]sulfinyl}-N-hydroxyacetamide;
(2R)-2-(4-bromophenyl)-2-{[4-(2-butynyloxy)phenyl]sulfinyl}-N-hydroxyacetamide;
2-(4-bromophenyl)-2-{[4-(2-butynyloxy)phenyl]sulfonyl}-N-hydroxyacetamide;
2{[4-(2-butynyloxy)phenyl]sulfanyl}-N-hydroxy-2-[4-(2-thienyl)phenyl]acetamide;
(2R)-2-{[4-(2-butynyloxy)phenyl]sulfinyl)-N-hydroxy-2-[4-(2-thienyl)phenyl]ethanamide;
2-{[4-(2-butynyloxy)phenyl]sulfonyl}-N-hydroxy-2-[4-(2-thienyl)phenyl]acetamide;
2-{[4-(2-Butynyloxy)phenyl]sulfanyl}-N-hydroxy-2-(]-napthyl)acetamide;
2-{[4-(2-Butynyloxy)phenyl]sulfinyl}-N-hydroxy-2-(1-napthyl)acetamide;
2-{[4-(2-Butynyloxy)phenyl]sulfonyl}-N-hydroxy-2-(1-napthyl)acetamide;
2-{[4-(2-Butynyloxy)phenyl]sulfanyl}-2-(4-fluorophenyl)-N-hydroxy-2-(1-napthyl)acetamide;
2-{[4-(2-butynyloxy)phenyl]sulfinyl}-2-(4-fluorophenyl)-N-hydroxyacetamide;
2-{[4-(2-butynyloxy)phenyl]sulfonyl}-2-(4-fluorophenyl)-N-hydroxyacetamide;
2-(2-methoxyphenyl)-2-{[4-(2-butynyloxy)phenyl]sulfanyl}-N-hydroxyacetamide;
2-(2-methoxyphenyl)-2-{[4-(2-butynyloxy)phenyl]sulfinyl}-N-hydroxyacetamide;
2-{[4-(2-butynyloxy)phenyl]sulfanyl}-N-hydroxy-2-(4-ethoxyphenyl)acetamide;
2-{[4-(2-Butynyloxy)phenyl]sulfinyl}-N-hydroxy-2-(4-ethoxyphenyl)acetamide;
2-{[4-(2-butynyloxy)phenyl]sulfonyl}-2-(4-chlorophenyl)-N-hydroxyacetamide;
2-{[4-(2-Butynyloxy)phenyl]sulfanyl}-N-hydroxy-2-(3-bromophenyl)acetamide;
(2R)-2-{[4-(2-butynyloxy)phenyl]sulfinyl}-N-hydroxy-2-(3-bromophenyl)acetamide;
(2S)-2-{[4-(2-butynyloxy)phenyl]sulfinyl}-N-hydroxy-2-(3-bromophenyl)acetamide;
2-{[4-(2-Butynyloxy)phenyl]sulfonyl}-2-(3-bromophenyl)-N-hydroxyacetamide;
2-{[4-(2-Butynyloxy)phenyl]sulfanyl}-2-isopropyl-N-hydroxyacetamide;
(R)-2-{[4-(2-butynyloxy)phenyl]sulfinyl}-2-isopropyl-N-hydroxyacetamide;
(S)-2-{[4-(2-butynyloxy)phenyl]sulfinyl}-2-isopropyl-N-hydroxyacetamide;
2-{[4-(2-butynyloxy)phenyl]sulfonyl}-2-isoprpyl-N-hydroxyacetamide;
2-{[4-(2-Butynyloxy)phenyl]sulfanyl}-2-phenyl-N-hydroxyacetamide;
(R)-2-{[4-(2-butynyloxy)phenyl]sulfinyl}-2-phenyl-N-hydroxyacetamide;
(S)-2-{[4-(2-butynyloxy)phenyl]sulfinyl}-2-phenyl-N-hydroxyacetamide;
2-{[4-(2-Butynyloxy)phenyl]sulfanyl}-2-(2-naphthyl)-N-hydroxyacetamide;
2-{[4-(2-butynyloxy)phenyl]sulfinyl}-2-(2-naphthyl)-N-hydroxyacetamide;
2-{[4-(2-butynyloxy)phenyl]sulfonyl}-2-(2-naphthyl)-N-hydroxyacetamide;
Tert-butyl-4-[1-{[4-(2-butynyloxy)phenyl]sulfonyl}-2-(hydroxyamino)-2-oxoethyl]-1-piperidine carboxylate;
2-{[4-(2-butynyloxy)phenyl]sulfonyl}-N-hydroxy-2-(4-piperidinyl)acetamide;
2-{[4-(2-butynyloxy)phenyl]sulfonyl}-N-hydroxy-2-[1-(4-methoxybenzyl)-4-piperidinyl]acetamide;
2-(1-benzoyl-4-piperidinyl)-2-{[4-(2-butynyloxy)phenyl]sulfonyl}-Hydroxyacetamide;
2-(1-acetyl-4-piperidinyl)-2-{[4-(2-butynyloxy)phenyl]sulfonyl}-N-hydroxyacetamide;
2-{[4-(2-Butynyloxy)phenyl]sulfonyl}-N-hydroxy-2-tetrahydro-2H-pyran-4yl-acetamide;
2-{[4-(2-Butynyloxy)phenyl]sulfonyl}-N-hydroxy-2-tetrahydro-2H-thiopyran-4yl-acetamide;
2-{[4-(2-Butynyloxy)phenyl]sulfonyl}-N-hydroxy-2-(1-oxidotetrahydro-2H-thiopyran-4yl acetamide; and
2-{[4-(2-Butynyloxy)phenyl]sulfonyl}-N-hydroxy-2-(1,1-dioxidotetrahydro-2H-thiopyran-4yl)acetamide.

\* \* \* \* \*